US 6,981,660 B2

(12) United States Patent
Piper

(10) Patent No.: US 6,981,660 B2
(45) Date of Patent: Jan. 3, 2006

(54) SHOCK WAVE AEROSOLIZATION APPARATUS AND METHOD

(75) Inventor: Samuel David Piper, Sacramento, CA (US)

(73) Assignee: Evit Labs, Carmichael, CA (US)

( * ) Notice: Subject to any disclaimer, the term of this patent is extended or adjusted under 35 U.S.C. 154(b) by 89 days.

(21) Appl. No.: 10/462,007

(22) Filed: Jun. 13, 2003

(65) Prior Publication Data

US 2004/0050966 A1    Mar. 18, 2004

Related U.S. Application Data

(63) Continuation-in-part of application No. 09/963,886, filed on Sep. 25, 2001, now Pat. No. 6,742,721.

(60) Provisional application No. 60/389,049, filed on Jun. 13, 2002, provisional application No. 60/305,088, filed on Jul. 12, 2001, provisional application No. 60/235,597, filed on Sep. 25, 2000.

(51) Int. Cl.
*B05R 7/04*      (2006.01)
*B05R 7/12*      (2006.01)
*B05R 7/06*      (2006.01)
*A62C 5/02*      (2006.01)

(52) U.S. Cl. .......................... 239/433; 239/8; 239/10; 239/407; 239/409; 239/413; 239/425.5

(58) Field of Classification Search .............. 239/433, 239/398, 407, 409, 413, 424, 424.5, 425.5, 239/8, 10, 601

See application file for complete search history.

(56) References Cited

U.S. PATENT DOCUMENTS

| 4,284,418 | A | * | 8/1981 | Andres | ........................... 95/32 |
| 5,474,059 | A | * | 12/1995 | Cooper | .................. 128/200.22 |
| 5,483,953 | A | * | 1/1996 | Cooper | .................. 128/200.22 |
| 6,009,869 | A | * | 1/2000 | Corbeil | ................. 128/200.21 |
| 6,742,721 | B2 | * | 6/2004 | Piper | ..................... 239/265.11 |

FOREIGN PATENT DOCUMENTS

WO      WO 97/48496      12/1997

* cited by examiner

*Primary Examiner*—Davis Hwu
(74) *Attorney, Agent, or Firm*—John P. O'Banion

(57) ABSTRACT

A pneumatic inhaler that is able to deliver a controlled burst or dose of aerosol from a reservoir of liquid or powder medication. A supersonic jet of gas is emitted from a nozzle and shock waves are developed in the jet. In one embodiment the supersonic jet is directed into a shock chamber. Liquid or micronized powder material is introduced into the supersonic jet to form an aerosol. In one embodiment, smaller aerosol particles are separated from larger aerosol particles with a separator. In another embodiment, the produced aerosol is contained in an aerosol storage chamber prior to inhalation by the users.

69 Claims, 39 Drawing Sheets

SHOCK WAVE AEROSOLIZATION APPARATUS AND METHOD

CROSS-REFERENCE TO RELATED APPLICATIONS

This application is a continuation-in-part of U.S. application Ser. No. 09/963,886 filed on Sep. 25, 2001 U.S. Pat. No. 6,742,721, which claims priority to U.S. provisional application Ser. No. 60/305,088 filed on Jul. 12, 2001 and to U.S. provisional application Ser. No. 60/235,597 filed on Sep. 25, 2000. This application also claims priority to U.S. provisional application Ser. No. 60/389,049 filed on Jun. 13, 2002.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to aerosol generating devices, and more particularly to inhalers that may be used to dispense liquid or powder medication in short bursts of aerosol.

2. Description of the Background Art

Some medicines cannot withstand the environment of the digestive tract and must be delivered to the bloodstream of the patient intravenously or by some other method. One effective means for delivery of such medications to the blood stream is through the membranes and air passageways of the lung.

Inhalers of various types have been widely used for inhalation delivery of aerosols containing medication or other constituents to the conductive airways of the lung and the gas exchange regions of the deep lung. Aerosols are relatively stable suspensions of finely divided droplets or solid particles in a gaseous medium. When inhaled, aerosol particles may be deposited by contact upon the various surfaces of the respiratory tract leading to the absorption of the particles through the membranes of the lung into the blood stream to provide the desired therapeutic action, or planned diagnostic behavior depending on the particular properties of the particles.

Because of the high permeability of the membranes of the lung and the copious flow of blood through the lung, medications deposited in the lung can readily enter the blood stream for delivery throughout the body. This may also allow for the use of lower initial doses than would normally be required to be taken orally to achieve the desired concentration of medication in the blood. Other medications can directly influence the airway epithelium and effect responses via various airway receptors. Still other types of aerosol particles deposited in the lung can act as tracers of airflow or indicators of lung responses and can otherwise be a valuable diagnostic tool. Properly generated and formulated aerosols can therefore be helpful in medical treatment. Inhalable aerosol particles capable of deposition within the lung are typically those with an aerodynamic equivalent diameter of between 1 and 5 micrometers.

Early attempts at producing an inhalation medical treatment include the use of atomizers. Atomizers are typically equipped with reservoirs, nozzles, and bulbs. Upon squeezing the bulb, liquid medication, which is placed within the reservoir, is drawn from the reservoir and sprayed by the nozzle for inhalation by the patient. However, the particle size produced by atomizers is too large for effective deposition in the lungs, although variants of the technique are still used for deposition of topical medication into the nasal cavity and associated tissues. A further disadvantage of atomizers is that they are unable to deliver a consistent dose due to discrepancies in user technique and the duration of each burst. Accordingly, atomizers are appropriate for delivery of medication to the sinus cavity, where the larger aerosol particle size is more effective for deposition but inappropriate for deposition in the deep lung.

Inhalers known in the art employ several techniques to achieve effective aerosolization of medicines for deposition in the lung. An inhaler produces a burst of aerosol consisting of fine particles intended for inhalation by a patient with a single breath. Inhalers are popular aerosol delivery devices because they are generally portable and are convenient to use. The particle size of the aerosol emitted from a typical inhaler is required to be considerably smaller than a conventional spray atomizer to ensure the appropriate deposition within the lungs.

Commonly, inhalers are pre-packaged containers containing a mixture of medication to be aerosolized and a low saturation pressure vapor or gas, such as chlorofluorocarbons (CFCs), which are used as a propellant. The canister carrying the mixture of the medication and the propellant is equipped with a valve. When the valve is actuated, the inhaler dispenses a set amount of liquid and medication through a nozzle, creating a spray. Upon release into the atmosphere, the low saturation pressure propellant is able to evaporate quickly leaving small aerosol particles of medication that are suitable for immediate inhalation. One disadvantage to this approach is that the propellant and the medication must be mixed for a significant period of time prior to inhalation by the patient, making them unsuitable for many medications. Furthermore, the pre-mixing of the medication and the propellant requires a different approach to gain regulatory approval, necessitating significant development time and capital, thereby significantly increasing the ultimate cost to the patient over the cost of liquid formulations of same medication. Furthermore, to prevent agglomeration of the medication within the canister, surfactants are also added to the formulation, which often leave an undesirable taste in the mouth of the patient after inhalation. Lastly, this approach is generally unsuitable for medications requiring large quantities of medication to achieve efficacious results.

Another inhaler strategy that is being employed with greater frequency is the aerosolization of dry medicament powders. Medicinal powders are prepared in advance and placed in a reservoir within the inhaler, or within blister pouches. Blister pouches have the advantage of being able to better preserve the powder from contamination and moisture. When the patient is ready for a dose of medication, they either access the reservoir to dispense an appropriate amount of powdered medication, or puncture a blister pouch containing the powder medicament.

Aerosolization of powders is typically achieved by the gas flow produced by the inhalation of the patient. However, the aerosolization of medicinal powders is plagued by problems of moisture contamination and the inconsistencies in inhalation effort by the patient from dose to dose. Furthermore, powder formulations are often as expensive to develop as pre-mixed propellants and may require complex, sophisticated and expensive manufacturing processes in their production. In addition, many medications are not effective after reformulation as a powder. Finally, powder aerosolization may be ineffective due to the appearance of an electric charge build up on the individual powder particles causing particles to attach to other particles or to the delivery device. Recent studies using inhaled powder medications have indicated that problems of pulmonary fibrosis may exist when treating chronic conditions with inhaled powder medication.

A third inhaler strategy employs ultrasonic energy to aerosolize bursts of liquid medication. These devices require precise electronic valves and associated electronic circuitry, making them expensive to manufacture and prone to malfunction. Additionally, the particle size of the aerosol produced by these devices is often too large for optimal deposition in the lung. Large and inconsistent aerosol particle size production by the inhaler results in an inconsistent and inefficient delivery of the medication to the lung.

Additionally, ultrasonic inhalers using piezo-electric crystals to create aerosolization of the medicine are often not suitable for delivering proteins, peptides and antibodies and the like because of the damage and loss of biological activity that occurs with ultrasound. Other medicines have required expensive reformulizations in order to be delivered by the ultrasonic aerosolization method. Lastly, ultrasonic inhaler technologies have been shown to have difficulties in delivering concentrated medication, making them suitable for potent medications only, and unsuitable for the delivery of medication requiring large quantities of medication to be efficacious.

Therefore, a need exists for a technology which can deliver aerosol bursts of liquid medication at a particle size that is appropriate for lung deposition which is inexpensive for the patient, produces consistent output, uses a formulation which is inexpensive to develop and produce, that is reliable, that is easy to use, which does not require the mixing of medication and propellant until the moment of aerosolization, and which can deliver large quantities of medication when needed. The present invention satisfies this need, as well as others and has the further advantages of providing superior aerosol quality, and being lightweight and portable.

BRIEF SUMMARY OF THE INVENTION

The present invention generally pertains to a pneumatic metered dose inhaler that is able to deliver a controlled burst or dose of aerosol from a reservoir of liquid medication. The invention is appropriate for the aerosolization of liquid medication that is in solution or in suspension form. The invention is also ideal for the delivery of unique and specialty liquid medications in short aerosol bursts because no additional formulation development is needed. The apparatus has the further advantage of being able to deliver multiple medications, as mixed by the patient, doctor, or pharmacist, with a single burst of aerosol at a repeatable output. Because the medication and the propellant are not mixed until aerosolization occurs, the current invention is appropriate for more pharmaceutical agents than can be used by currently available inhalers at a substantial cost savings.

According to one aspect of the invention, an apparatus and method are provided for producing an aerosol suspension that comprises directing a flow of gas through a nozzle to form a supersonic jet of gas and then introducing material into the supersonic jet of gas to produce an aerosol suspension.

According to another aspect of the invention, an apparatus for producing shock wave aerosolization is provided that has a source of compressed gas and a nozzle configured to generating a supersonic jet of gas from the source of compressed gas.

Another aspect of the invention provides a sonic shock chamber that is configured to receive the supersonic jet of gas from the nozzle. Compression and expansion shock waves created by the supersonic jet are reflected within the confines of the expanding supersonic jet.

According to another aspect of the invention, an apparatus is provided that has an actuator handle with a compressed gas container and a user actuated valve configured to release the compressed gas in bursts. The apparatus also has a jet orifice configured to receive compressed gas from the gas container and produce a supersonic jet directed through a sonic shock chamber to produce shock waves. A source of material for aerosolization associated with the jet orifice and shock chamber is also provided and introduced into the burst of compressed gas creating aerosol particles.

According to yet another aspect of the invention, an aerosol separator is provided that separates large aerosol particles from small aerosol particles that have been produced.

According to another aspect of the invention, the aerosol separator is also configured to reflect acoustic energy from the supersonic jet of gas to the produced aerosol particles and reduce the size of the larger aerosol particles emitted from the jet.

According to still another aspect of the invention, a means for storing separated aerosol particles is provided.

By way of example and not of limitation, a first embodiment of the present invention employs a cartridge or cylinder for containing virtually any type of compressed gas. Typically, carbon dioxide gas is used at a preferred pressure of approximately 750 psi, because the gas has a low critical temperature and pressure, allowing a small canister to carry significantly more than if filled with many other gases. The compressed gas is released in small bursts by a valve actuated by the patient, which delivers the gas to the supersonic shock nozzle. The nozzle comprises a jet orifice from which the compressed gas discharges into a sonic shock chamber. Provided that substantial backpressure is supplied, a supersonic jet of gas exits from the jet orifice of the nozzle, which may be over expanded, under expanded or perfectly expanded. If the jet is over or under expanded, the supersonic jet, which remains at approximately the diameter of the jet orifice and which travels down the axis of the shock chamber and establishes a series of reflected compression and expansion shock waves. A perfectly expanded jet will have a cylindrical shock wave that envelops the entire jet. Although this would be preferable for the production of aerosol, it is often impractical as a result of variations in gas supply pressure and the desired dimensional scale of the preferred embodiment of the current invention. Therefore, the nozzle is designed to provide a jet that is over expanded in one embodiment, and this may be considered optimum.

Upon formation of the jet and the resulting reflected shock waves in the shock chamber, a vacuum is generated which causes liquid, for example, from the reservoir to be entrained through the liquid feed channels into the shock chamber. The preferred liquid feed channels direct the incoming fluid circumferentially around the nozzle and entrance to the shock chamber. Upon entrainment of the liquid to the shock chamber, the initially entrained liquid comes in contact with the shear forces created by the shock waves, producing abundant amounts of aerosol particles suitable for inhalation. Shock waves are uniquely able to produce tremendous quantities of aerosol with good particle size for inhalation because they have the property of having large pressure differences over very small distances, thus making them able to generate substantial shear forces. The result of liquid traveling across this shock boundary is to be violently and physically disturbed, thus disintegrating into a dense burst of aerosol with appropriate particle size for inhalation. This represents a significant advance over traditional atomizers, which lacked the ability to introduce medication to shock waves of any design or magnitude, resulting in lower output and larger particle size.

Once the liquid has been entrained into the shock chamber and jet, the integrity of the jet and resulting reflecting shock waves may be destroyed, resulting in a reduction in the subsequent production of aerosol particles than is produced in the initial burst. The volume and rate of liquid or other material that is entrained in the jet is therefore preferably regulated. The subsequent production of aerosol also has a generally larger particle size than the initial burst. The overall result is an initial burst of aerosol ideally suited for an inhaler, generally lasting less than a second, depending on the rate of medication introduction to the jet. The output and particle size of such an inhaler is substantially better than would be predicted from the steady state operation of an atomizer or nebulizer nozzle of similar design. It is not possible to employ the same technique in the design and manufacture of an atomizer or nebulizer, because these devices are intended to run continuously and the unique phenomena of the current invention only occurs with the controlled introduction of fluids to the reflected shock waves. Since the aerosolization process is so efficient, only a little volume of compressed gas is required for a burst of aerosol, making it possible, and efficient, to store enough carbon dioxide in a small canister for 200 bursts or more.

Although not optimum under many conditions, a similar result is obtained by providing a shock region instead of a shock chamber. In this embodiment, the supersonic jet of gas exits directly into a generally open region allowing for the formation of reflected shock waves within the exiting jet. Liquid is entrained through one or more feed tubes placed proximally to the jet at a sufficient distance to generate a vacuum. Again, once the entrained liquid comes into contact with the reflected shock waves, a tremendous amount of aerosol particles are produced, and the integrity of the sonic jet and the shock waves is destroyed. Based on experimentation, such an approach was not found to be optimum because it did not allow for the precise introduction of fluid to the shock waves, which affects the output and particle size of the resulting aerosol burst. It should be noted that such an open design does have distinct advantages for thick, viscous fluids, because of the potential of clogging involved with the closed design of the previous embodiment due to the difficulty of cleaning.

In addition, the aerosolization process can be further optimized through placement of a liquid feed choke between the fluid reservoir containing the medication, and the liquid feeds that lead into the shock chamber or shock region. By further choking the flow of liquid down, it is possible to better control the introduction of fluid into the supersonic jet produced in the shock chamber, thus allowing for better aerosolization and an increase in the duration of the aerosol burst, although it is still generally a momentary phenomena relative to normal jet nebulization technologies.

The preferred embodiment of the current invention draws liquid from a reservoir of medication that is preferably sufficient to hold approximately 200 doses, and has been shown to produce consistent doses of aerosolized liquid medication. In the event that extremely precise dosing is desired, or if a change in dosing is desired from burst to burst, one embodiment of the current invention may be modified to consist of a small reservoir, or multiple small reservoirs, that contain the exact amount of liquid desired for delivery, and which is less than the nozzle will entrain with a given burst, or predetermined series of bursts. Thus, the output of the inhaler is exactly equal to the contents of the reservoir, and may be easily changed from dose to dose.

Another embodiment of the invention includes the use of blister packs pre-filled with the exact amount of liquid intended for aerosolization rather than the use of a reservoir. Prior to the contents of a blister cell being delivered, a feed tube, which is in fluid communication with the supersonic shock nozzle, is caused to puncture and penetrate the blister cell. Upon actuation of the nozzle, the contents of the blister cell is completely entrained into the shock nozzle and aerosolized. Blister packs also have the added advantage of better preserving medication than multiple dose reservoirs due to the limited exposure of the medication to air prior to aerosolization.

Once the entrained liquid is aerosolized, the momentum of the jet carries the aerosol into a mouthpiece for immediate inhalation by the patient. Depending on the ability of the patient to coordinate actuation and inhalation, and the desired portion of the lung targeted for deposition, a spacer or valved holding chamber may be attached to the mouthpiece.

In another embodiment, spacers or chambers allow for easier coordination of patient's inhalation with device actuation and separate out comparatively smaller aerosol particles from larger aerosol particles that are inappropriate for deposition within the lung. Separation of smaller aerosol particles and a momentary delay in inhalation allows more time for the liquid aerosol particles to evaporate, producing superior sized aerosol particles (1–3 microns) for deposition in the alveolar portions of the lung.

In another embodiment, the aerosol particles that are produced are directed to a shock wave amplification chamber that reflects acoustic energy from the supersonic jet through the aerosol particles and reduces the size of the particles. The chamber also preferably separates the larger aerosol particles from the smaller aerosol particles.

Optionally, the exiting aerosol from the jet or the separated aerosol may be stored in an aerosol holding chamber. In one embodiment, the holding chamber stores aerosol upon actuation for subsequent inhalation. The chamber preferably has a valve that allows ambient air to be drawn into the holding chamber when the user inhales the aerosol through the mouthpiece. Additionally, as is well known in the industry, and recently reported during in-vitro investigations (Respiratory Care, June 2000, Volume 45, Number 6, "Consensus Conference on Aerosols and Delivery Devices", page 628), valved chambers often maintain a static electric charge due to rinsing with water that causes a significant loss of aerosol particles due to mutual static electric attraction. One embodiment preferably employs an anti-static plastic that prevents this phenomenon from occurring.

Additionally, the shock wave aerosolization process functions remarkably well with micronized powder in blister packs as well. Blister packs, containing one or more cells, are used to store a pre-determined amount of powder. Prior to aerosolization, a feed tube, which is in fluid communication with the shock wave aerosolization process nozzle, is inserted into the blister pack cell. Subsequent to the insertion of the feed tube, the carbon dioxide valve is actuated, creating a set burst of gas. As previously described, the carbon dioxide exits the throat of the jet, causing a vacuum, which entrains the micronized powder through the feed tube and into the shock chamber. As previously described with liquid medication, when medicinal powder is entrained it becomes efficiently aerosolized in the reflected shock waves and carried out to the mouthpiece or valve chamber, as intended.

An object of the invention is to provide an inhaler that can deliver a repeatable dose of aerosol containing particles appropriately sized for deposition within the patient's lung.

Another object of the invention is to provide an inhaler that can produce aerosol particles appropriate for deposition in the bronchial airways.

Another object of the invention is to provide an inhaler that can produce aerosol particles appropriate for deposition in the alveolar portions of the lung.

Another object of the invention is to provide an inhaler that can aerosolize an aqueous solution.

Another object of the invention is to provide an inhaler that can aerosolize a suspension of medication in liquid.

Another object of the invention is to provide an inhaler that can aerosolize liquid pharmaceutical formulations and peptides currently available only for nebulizers.

Another object of the invention is to provide an inhaler that does not mix medication and propellant prior to aerosolization.

Another object of the invention is to provide an inhaler that can deliver combinations of different medications with one burst.

Another object of the invention is to provide an inhaler with an acceptable aftertaste.

Another object of the invention is to provide an inhaler that is portable, convenient and easy to use.

Another object of the invention is to provide an inhaler that is inexpensive to produce.

Another object of the invention is to provide an inhaler that has a built in valved chamber for storage of aerosol.

Another object of the invention is to provide an invention that works in conjunction with blister packs that contain either liquid or powder.

Another object of the invention is to provide an invention that works in conjunction with concentrated and viscous medications.

Further objects and advantages of the invention will be brought out in the following portions of the specification, wherein, the detailed description is for the purpose of fully disclosing preferred embodiments of the invention without placing limitations thereon.

BRIEF DESCRIPTION OF THE DRAWINGS

The invention will be more fully understood by reference to the following drawings that are for illustrative purposes only.

DETAILED DESCRIPTION OF THE INVENTION

Referring more specifically to the drawings, for illustrative purposes the present invention is seen in the embodiments generally shown in FIG. 1 through FIG. 42.

Figure 1:
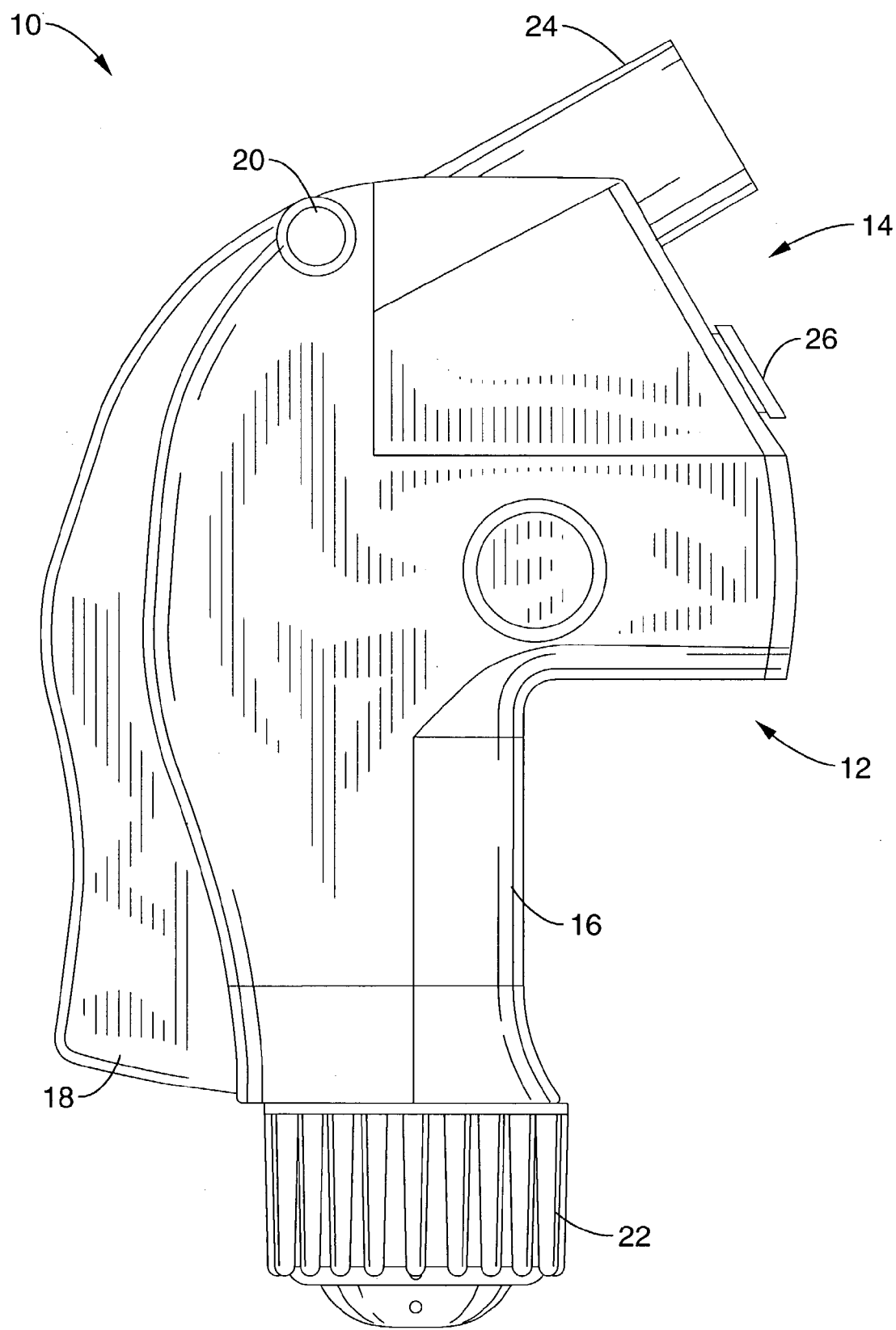
FIG. 1 is a side view of a first embodiment of a metered dose inhaler according to the present invention.
Figure 2:
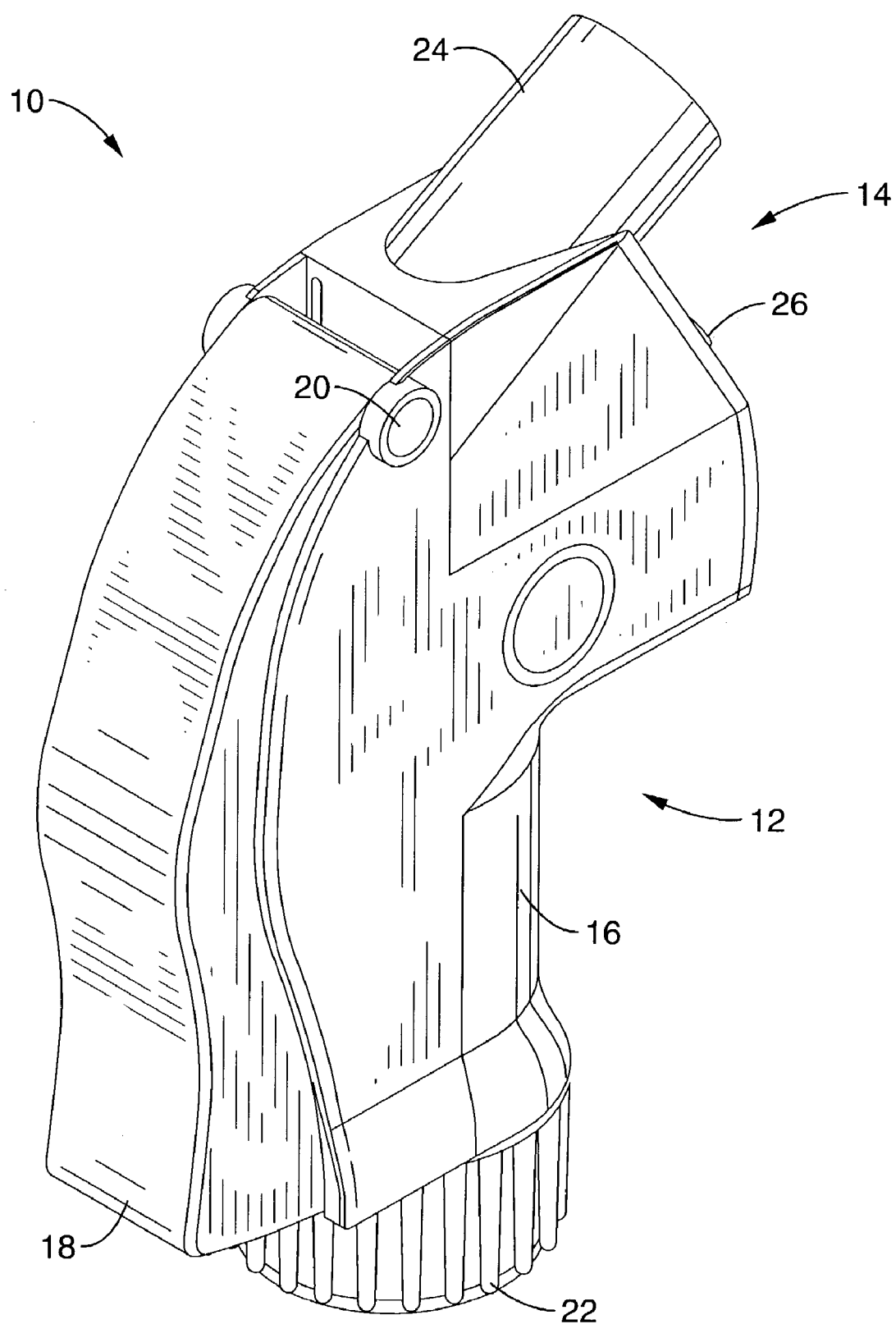
FIG. 2 is a perspective view of the inhaler of FIG. 1.
Figure 3:
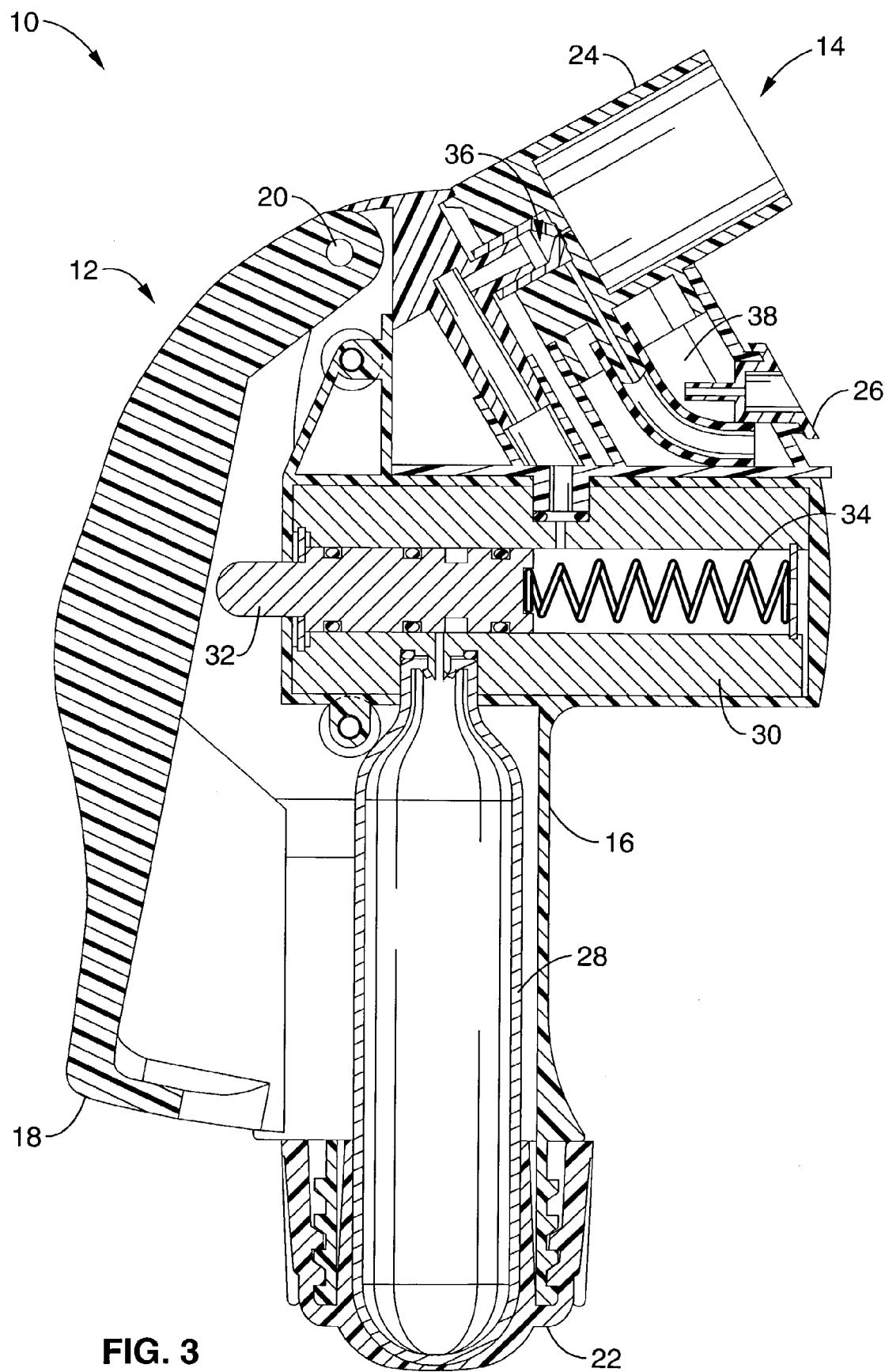
FIG. 3 is a side view in longitudinal cross-section of the inhaler of FIG. 1.
Figure 10:
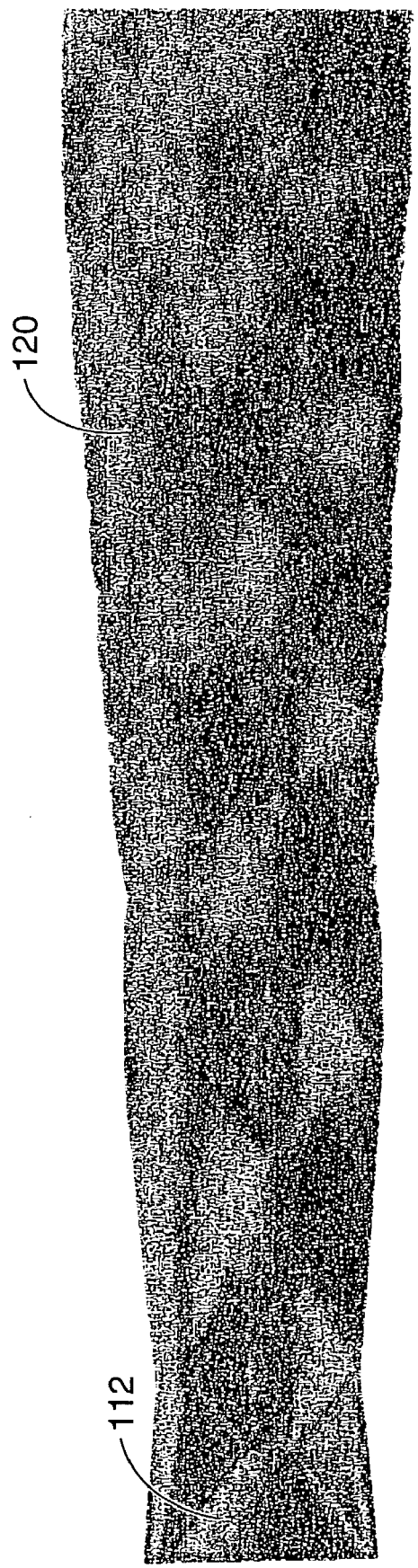
FIG. 10 is a rendering of an over expanded supersonic jet typically produced by the inhaler of FIG. 1.
Figure 11:
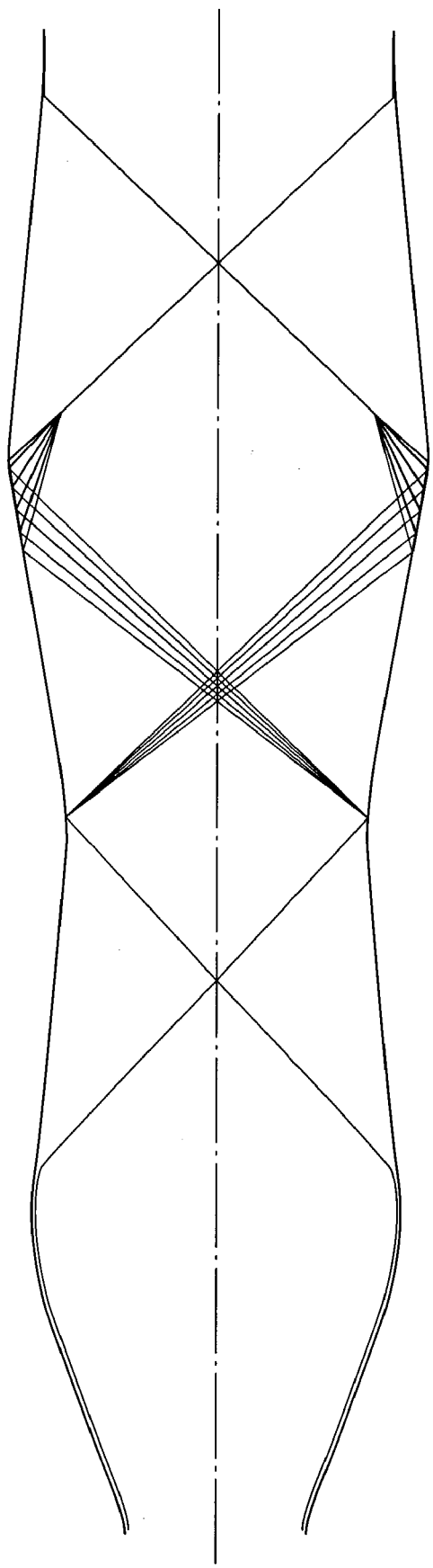
FIG. 11 is a schematic representation of the over expanded supersonic jet of FIG. 11.
Figure 13:
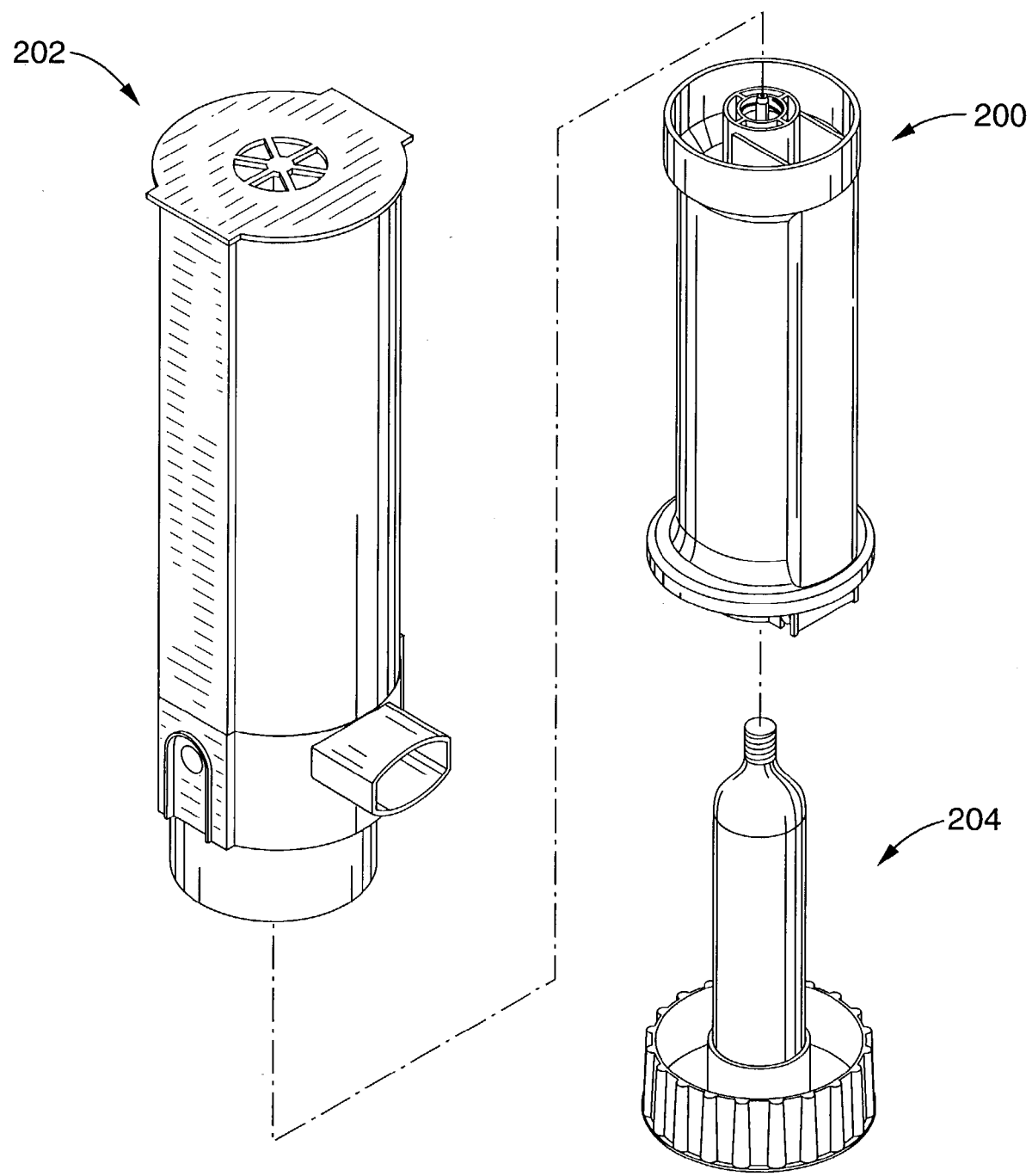
FIG. 13 is an exploded view of a second embodiment of an inhaler according to the present invention showing the reusable actuator handle, aerosol generator, and carbon dioxide cartridge.
Figure 14:
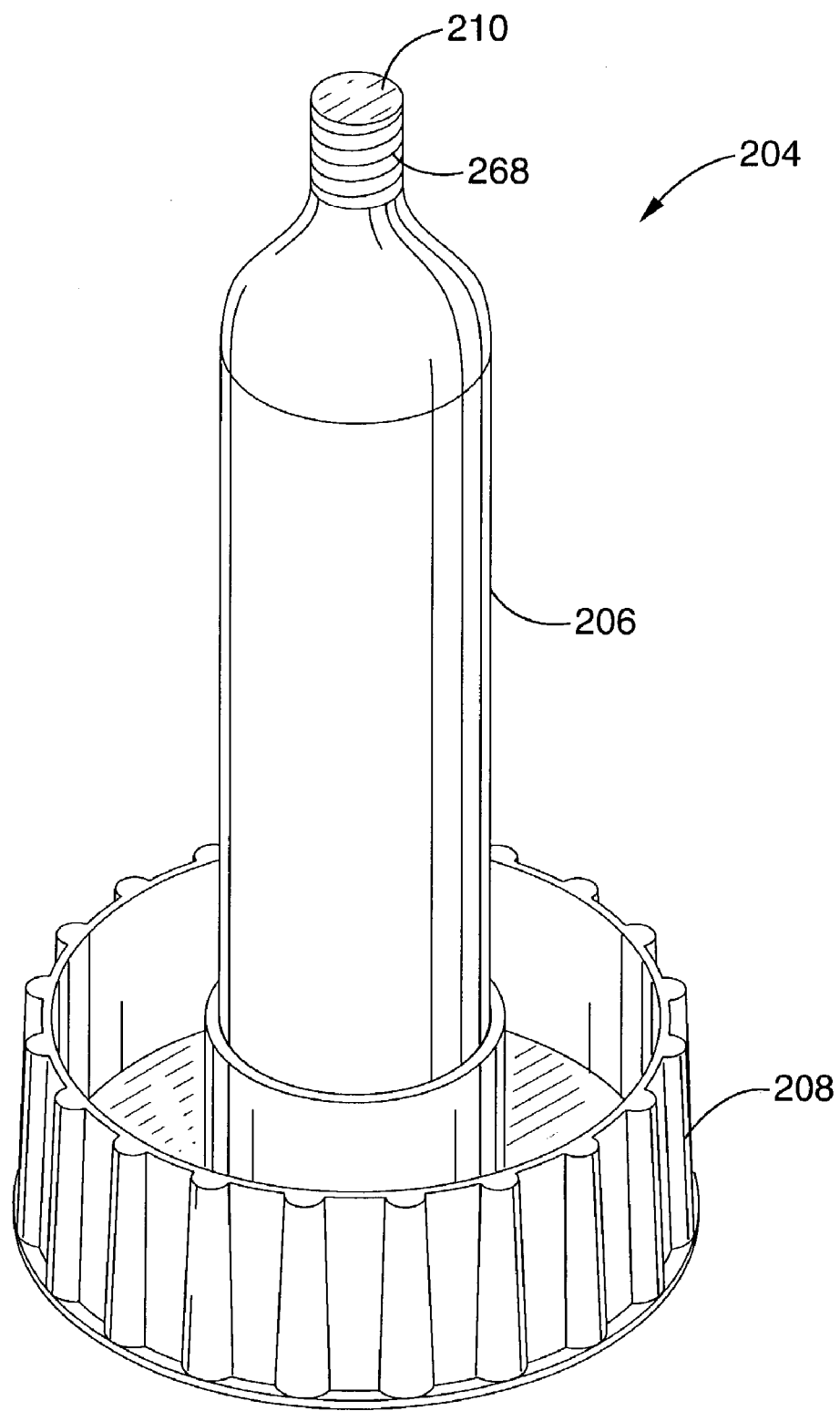
FIG. 14 is a perspective view of the disposable carbon dioxide refill cartridge portion of the inhaler of FIG. 13.
Figure 15:
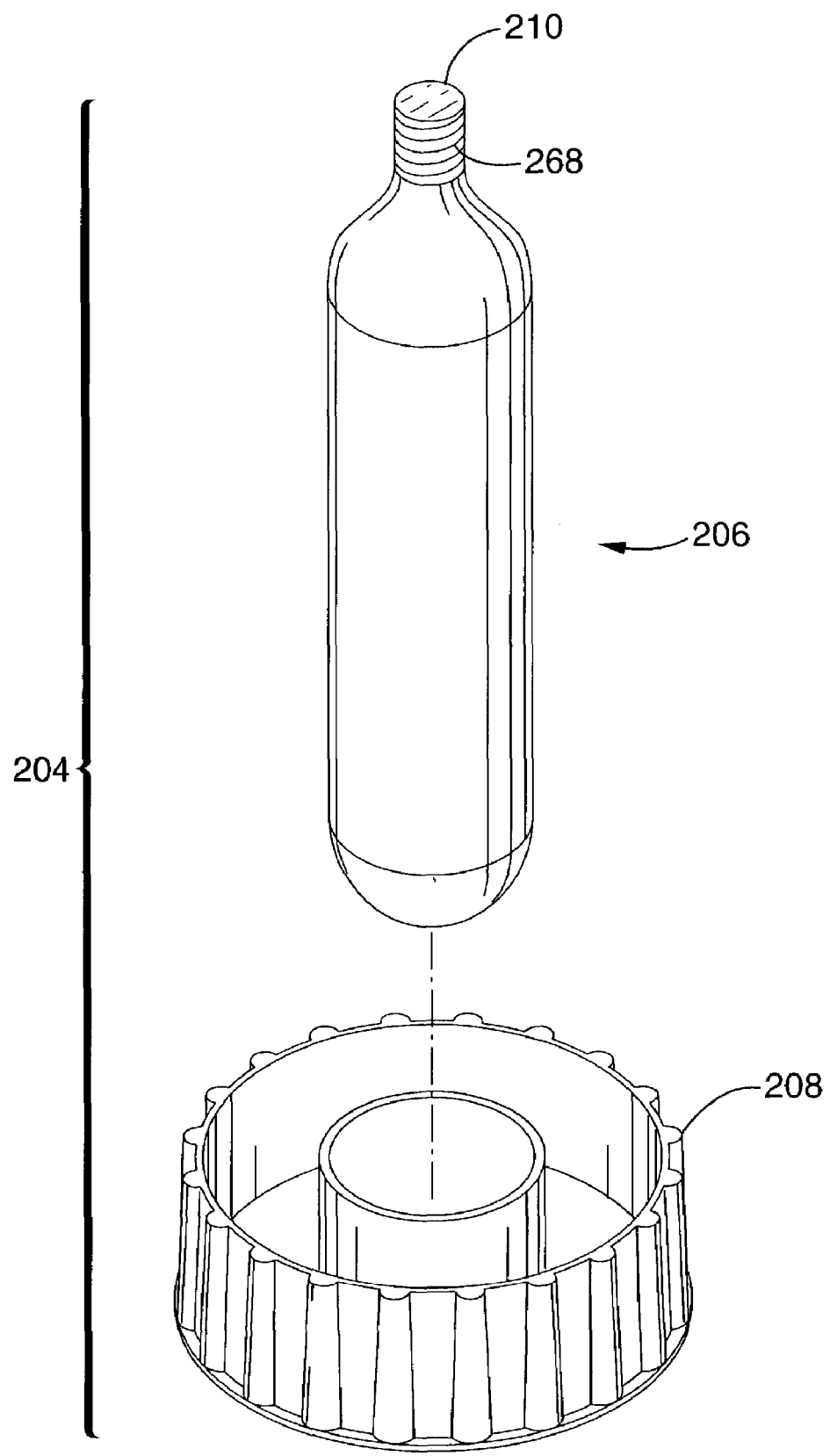
FIG. 15 is an exploded view of the carbon dioxide canister of FIG. 14.
Figure 29:
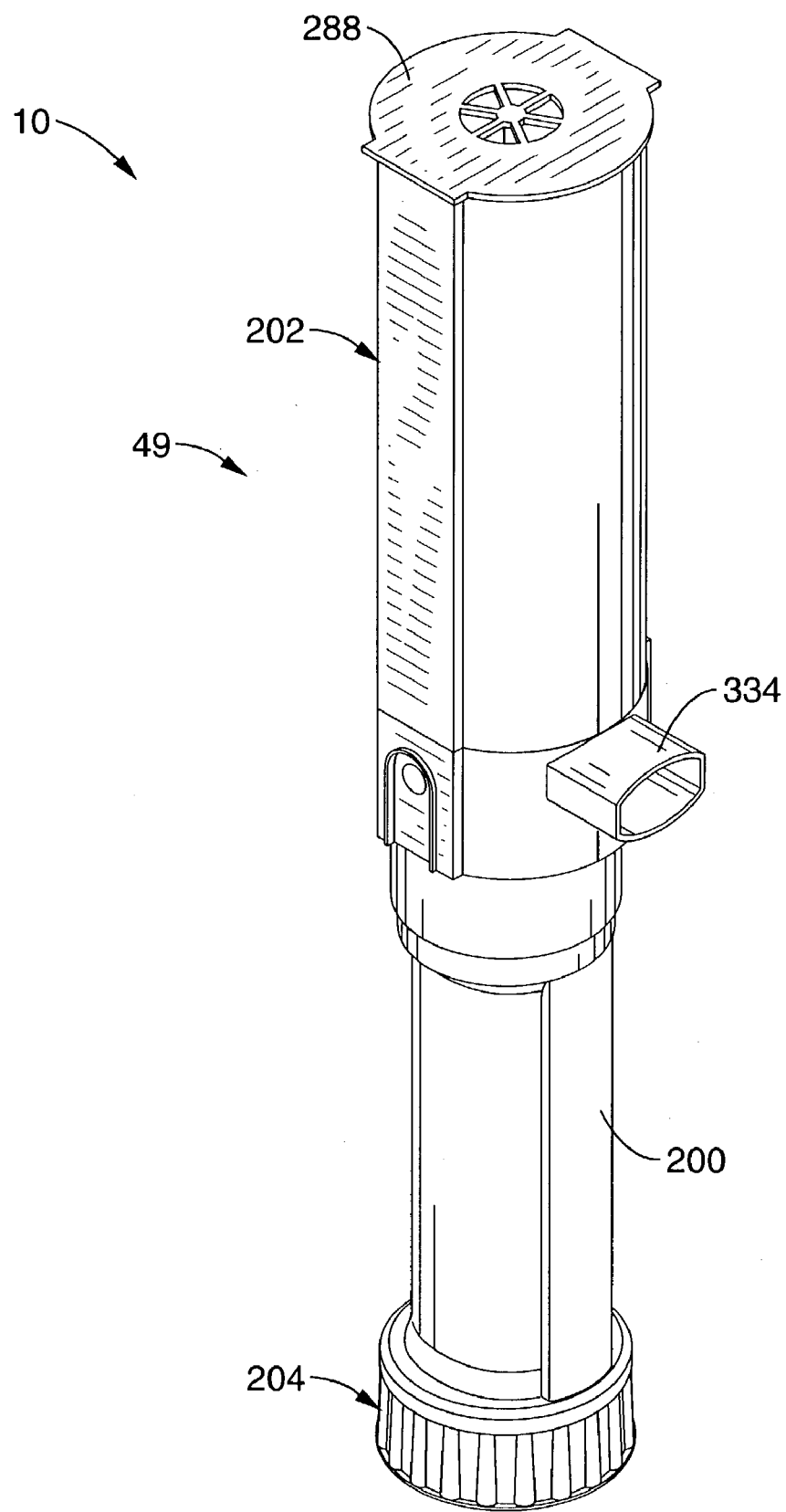
FIG. 29 is an assembled perspective view of the inhaler embodiment of FIG. 13.
Figure 30:
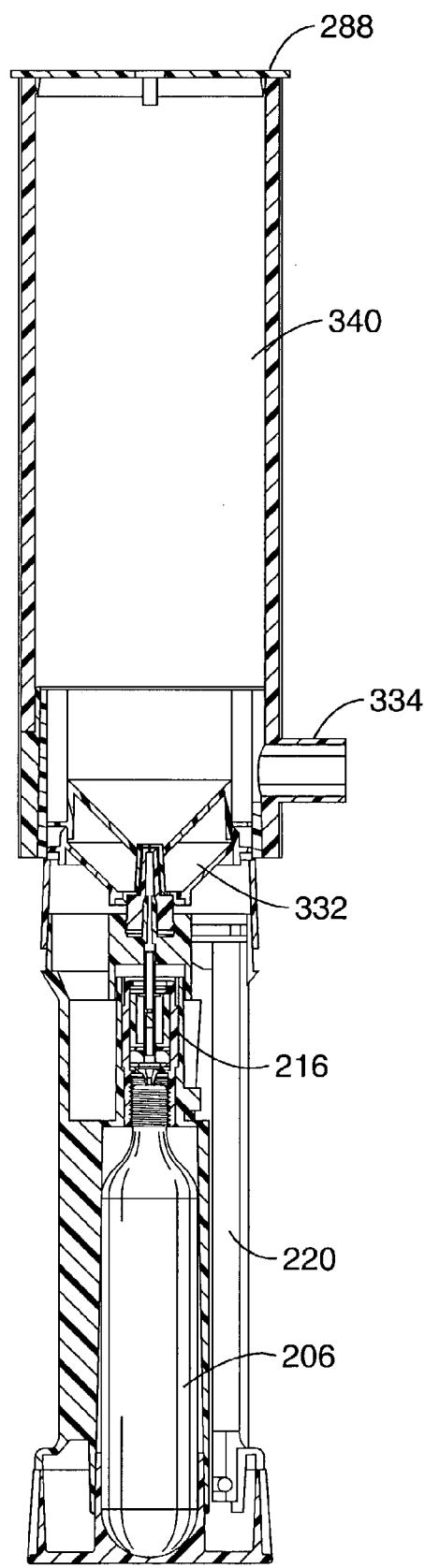
FIG. 30 is a side view in cross-section of the inhaler of FIG. 13 and FIG. 29.

FIG. 1 through FIG. 3 shows the overall configuration of a first embodiment of a shock wave aerosolization apparatus according to the present invention. The inhaler portion of the apparatus comprises two primary parts; an actuator 12 shown in FIG. 4, FIG. 5, and more specifically in FIG. 6, and an aerosol generator 14 shown in FIG. 7, FIG. 8 and more specifically in FIG. 9 and FIG. 12. FIG. 10 and FIG. 11 are for illustrative purposes regarding the nature of reflected shock waves in a supersonic jet. FIG. 13 and FIG. 29 show the overall configuration of a second embodiment of the invention. FIG. 14 and FIG. 15 show the gas canister assembly. FIG. 16 through FIG. 20 details the actuator handle assembly and metered gas valve. FIG. 21 through FIGS. 28, 31 and 32 shows the aerosol generator assembly of the second embodiment. FIGS. 29 and 30 shows the configuration of the apparatus during use.

Figure 33:
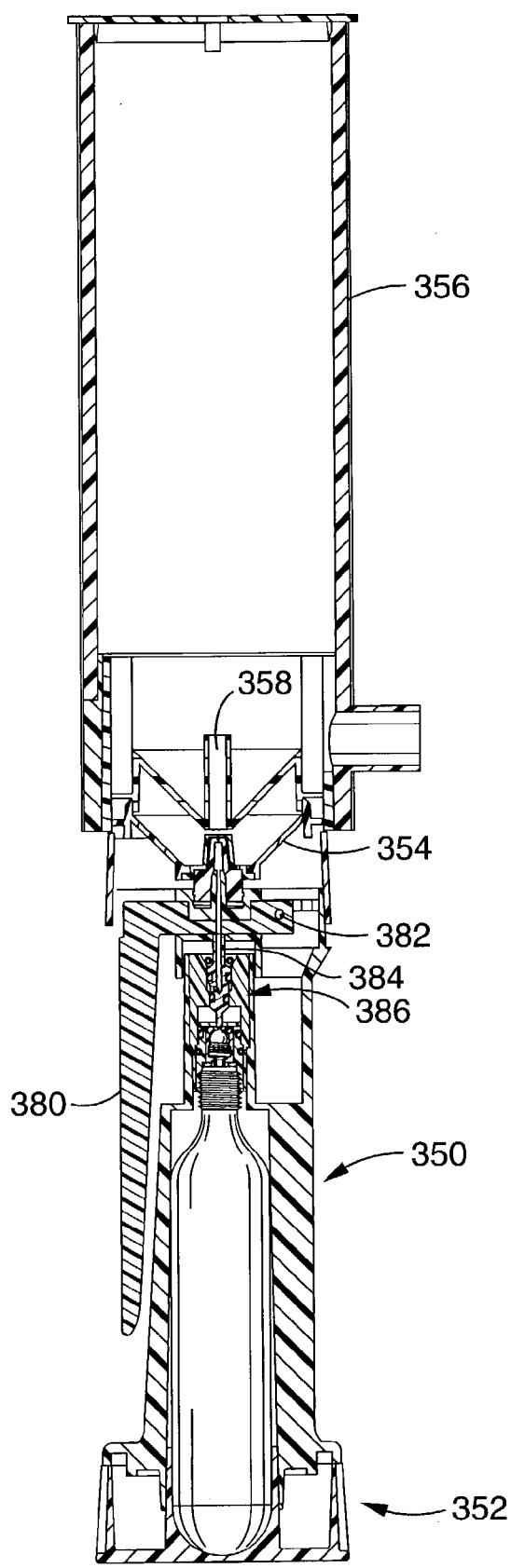
FIG. 33 is a side cross sectional view of an alternative and preferred embodiment of the entire invention.
Figure 34:
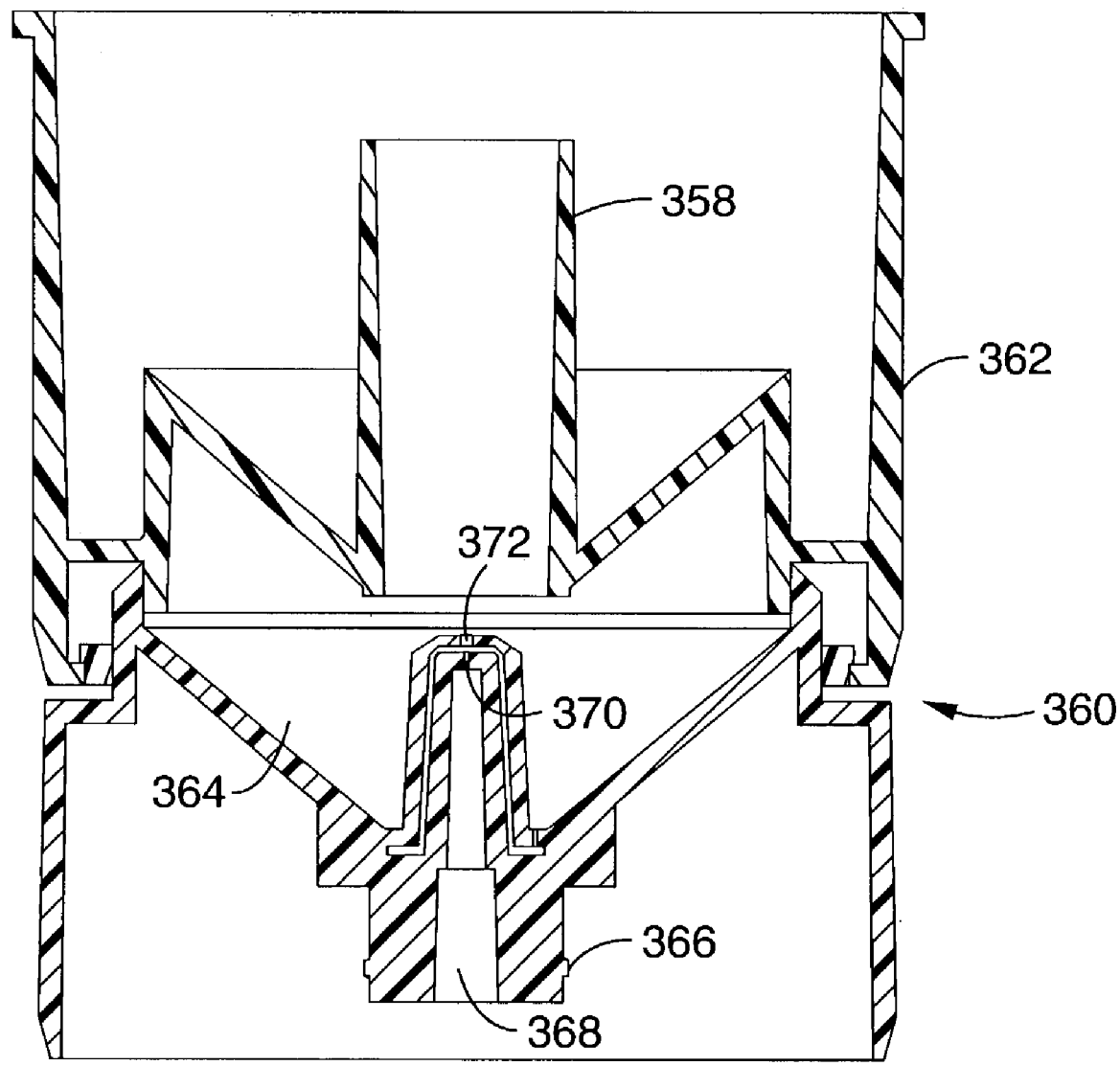
FIG. 34 is a sectional view of an alternative embodiment of an aerosol generator with a shock wave amplification chamber according to the present invention shown in FIG. 33.
Figure 35:
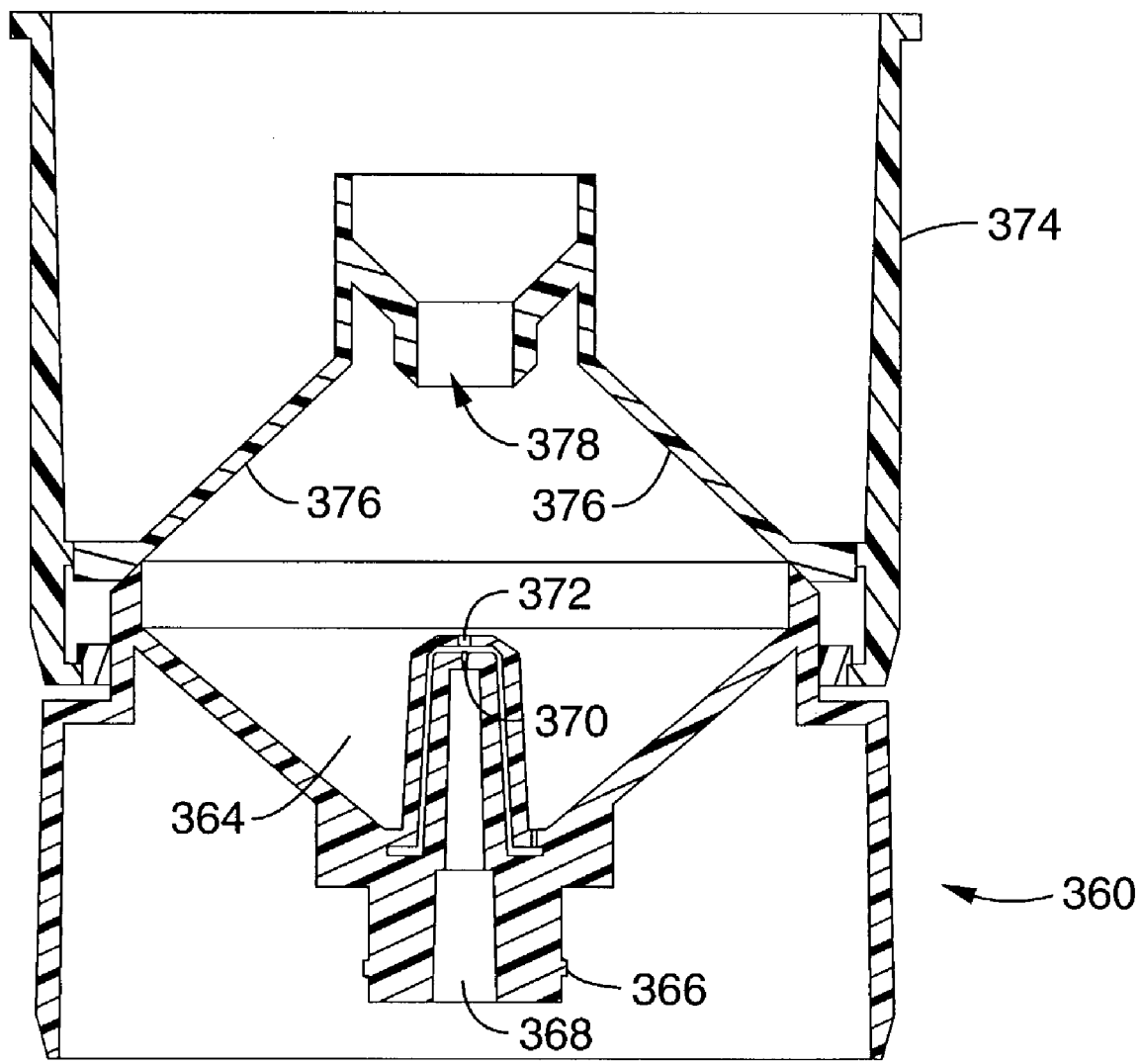
FIG. 35 is a side cross-sectional view of an aerosol generator with an alternative embodiment of a shock wave amplification chamber according to the present invention.

A third alternative embodiment of the invention with a shock wave amplification chamber aerosol separator and trigger is shown in FIGS. 33 through 34, and alternatively in FIG. 35.

A fourth embodiment of the invention with a blister pack medicine reservoir system is shown in FIG. 36 through FIG. 41. The alternative embodiment of the invention shown in FIG. 42 employs a supersonic shock nozzle assembly enclosed in a small disposable cartridge along with a single blister pack 484 containing sufficient medication for one aerosol treatment.

It will be appreciated that the several embodiments of the apparatus may vary as to configuration and as to details of the parts, and that the method may vary as to details of steps and their sequence, without departing from the basic concepts as disclosed herein.

Referring now to FIG. 1, the aerosolization apparatus 10 of the present invention generally includes an actuator 12 and an aerosol generator 14. The actuator 12 and the aerosol generator 14 are separable components in the embodiment shown, however, it will be understood that these components may be fully integrated and inseparable.

As seen in FIG. 2 and FIG. 3, the actuator 12 of apparatus 10 has a handle 16 that is preferably configured to fit in the notch between the thumb and first finger of the hand of the user and gripped. In the embodiment shown, the actuator 12 has a trigger 18 that pivots about trigger pin 20 and is brought toward the body of actuator 12 by the fingers of the user to actuate the device. The actuator 12 also has a cap 22 enclosing a gas canister that can be removed from the body of the actuator 12 as needed.

The aerosol generator 14 is operably coupled with actuator 12 and provides aerosolized medications to a user through a mouthpiece 24 when the trigger 18 is depressed. Medicine is disposed within a reservoir through a port that is sealed with a plug 26.

Turning now to FIG. 3, a cross section of the apparatus 10 with the actuator 12 coupled with the aerosol generator 14 is shown. The primary components of the actuator 12 are the handle 16, cap 22, gas canister 28, trigger 18, valve body 30, valve poppet 32, and valve spring 34. Carbon dioxide in a conventional gas canister 28 is used for illustration in the embodiment shown in FIG. 3. Gas canister 28 is disposed within handle 16 and is held in place by cap 22.

The primary components of the aerosol generator 14 are reservoir 38, mouthpiece 24, aerosolization nozzle 36 and plug 26. It can be seen that canister 28 provides a source of supply of gas to the aerosol generator 14 that is regulated by poppet 32. Gas from the canister 28 is directed through the aerosolization nozzle 36, mixed with medicine from reservoir 38 and out through the mouthpiece 24 to the user.

Figure 4:
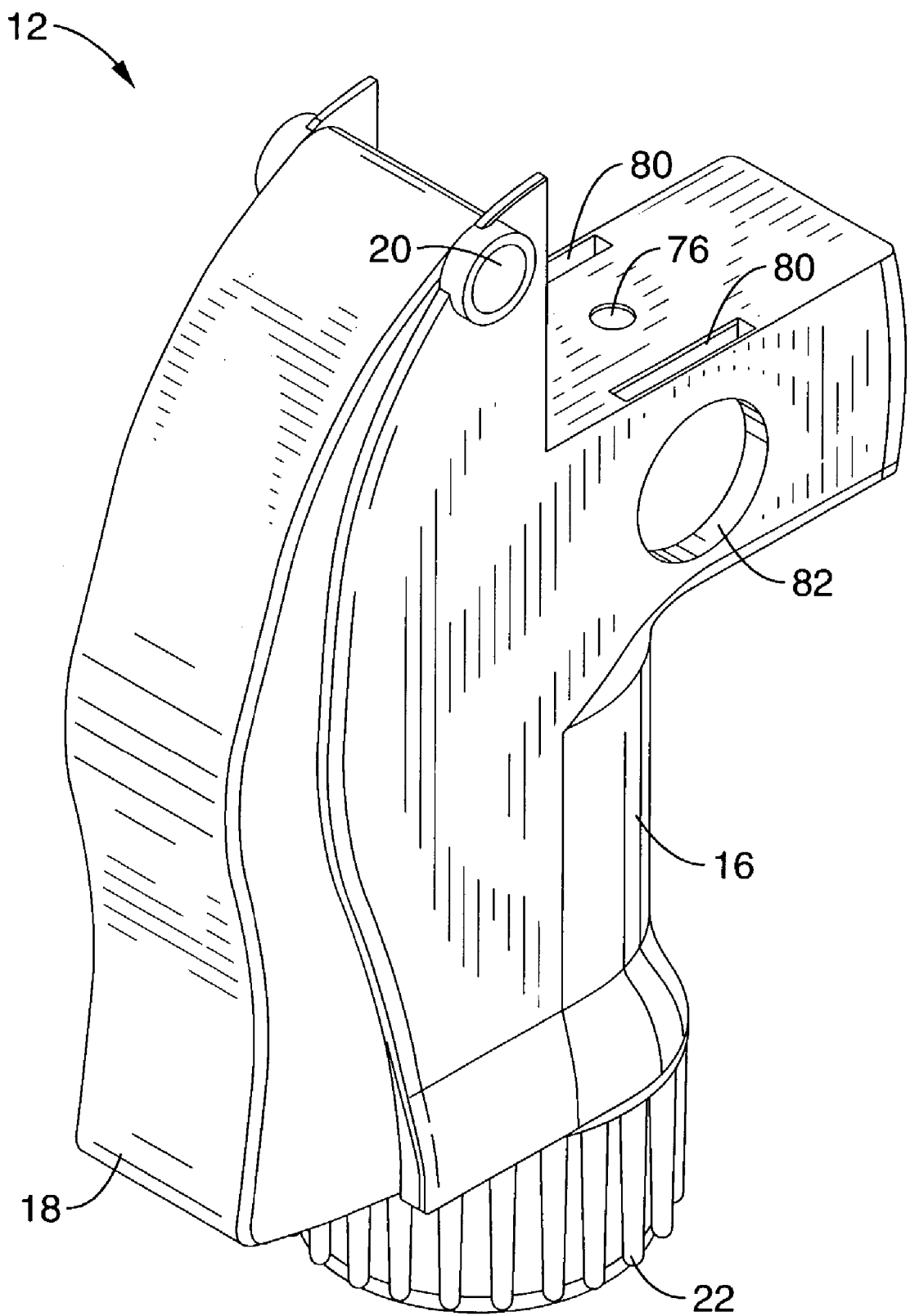
FIG. 4 is a perspective view of the actuator portion of the inhaler of FIG. 1.
Figure 5:
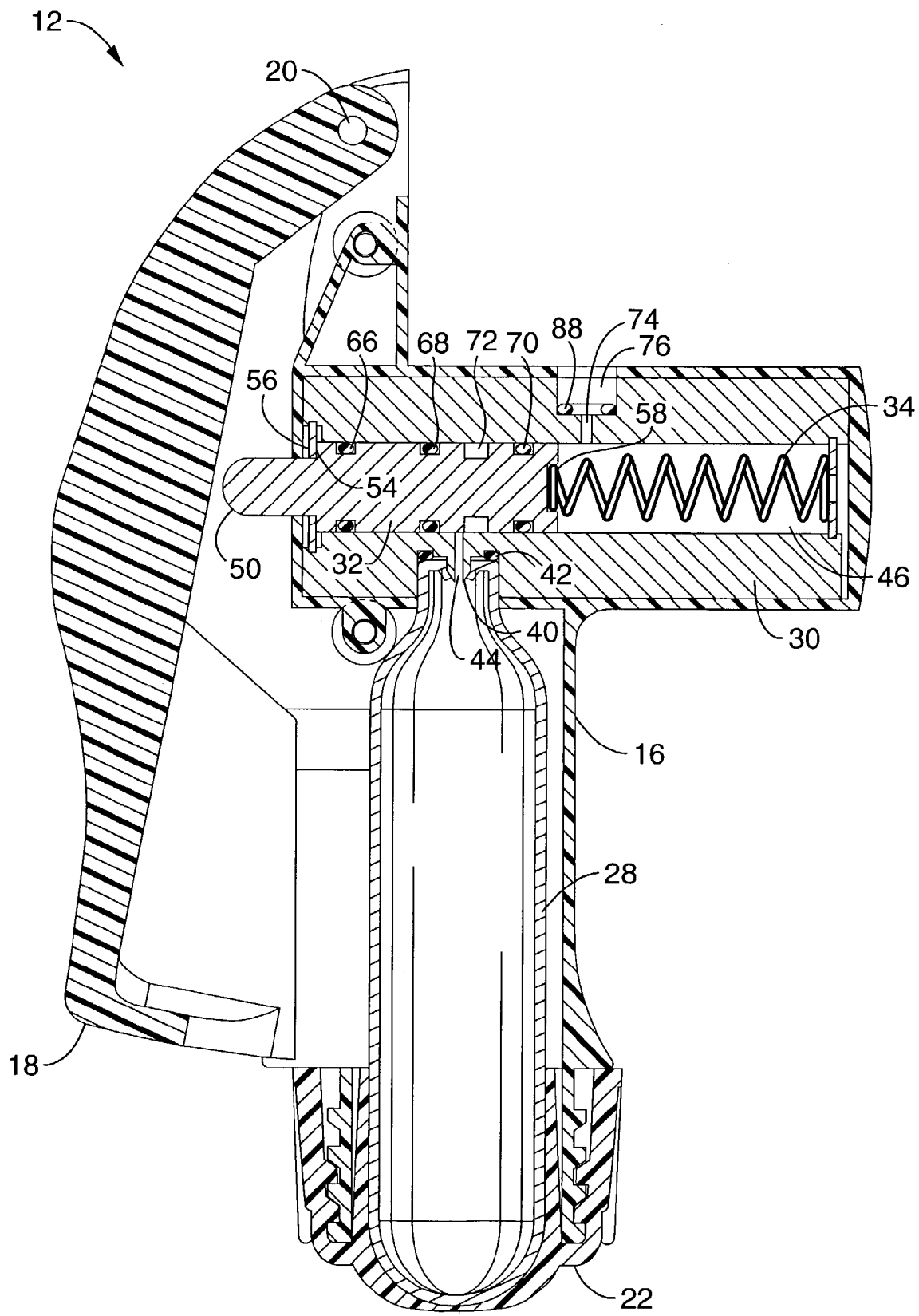
FIG. 5 is a side view in cross-section of the actuator of FIG. 4.

Referring also to FIG. 4 and FIG. 5, the aerosol generator 14 is releasibly coupled with the actuator 12. The aerosol generator 14 component can be quickly removed from the actuator 12 for refilling and cleaning. Likewise, different medications can be administered sequentially to a single patient by removing the first aerosol generator 14 after the first dosage is administered and replacing it with a second aerosol generator 14 that has a different medication. Thus, it can be seen that a practitioner can administer appropriate medications to any number of patients using one actuator 12 and a number of different aerosol generators 14 specially prepared for each patient.

Figure 6:
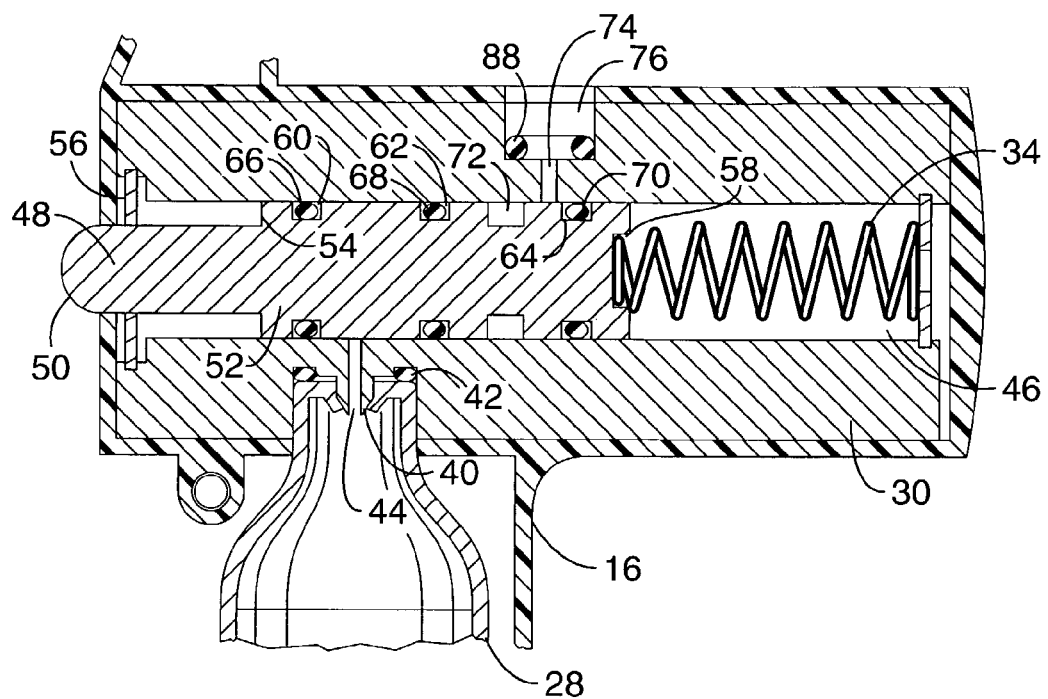
FIG. 6 is a detail side view in cross-section showing the valve portion of the actuator of FIG. 4 in the actuated state.

Turning now to FIG. 4, FIG. 5 and more specifically FIG. 6, actuator 12 is shown without the aerosol generator 14 in place. It will be seen that the actuator 12 is a source of gas supply that can be regulated by the actions of poppet 32 actuated by trigger 18. A metered volume of gas is produced to the aerosol generator 14 from the source of supply by the linear movement of poppet 32.

When cap 22 is removed from handle 16, a carbon dioxide canister 28 can be placed into cap 22 and then inserted into the internal space of handle 16. With the tightening of cap 22, carbon dioxide canister 28 is caused to be punctured by hollow prong 40, which is part of valve body 30, and thereafter the canister is sealed against canister o-ring 42.

Once punctured and sealed, carbon dioxide canister 28 is in fluid communication with valve poppet 32 disposed within valve poppet chamber 46 through canister conduit 44 within hollow prong 40 and the wall of valve body 30.

Valve poppet 32 comprises a trigger head 48 with an actuating cam surface 50 that smoothly engages trigger 18 through the full range of motion of the trigger pull. The poppet 32 is biased to the far left or "rest" position, as shown, by spring 34, such that shoulder 54 is caused to rest against stop plate 56. Spring 34 preferably fits within a spring indent 58 at the distal end of poppet 32.

The valve poppet in the activated position is shown in FIG. 6. It will be seen that valve poppet 32 is caused to move to the right, or "actuated" position, when trigger 18 is squeezed, resulting in force being applied to actuating cam surface 50 of trigger head 48 of poppet 32 in opposition to the force of valve spring 34.

The body 52 of poppet 32 preferably has a first o-ring groove 60, a second o-ring groove 62, and a third o-ring groove 64 that are mated with first o-ring 66, second o-ring 68, and third o-ring 70 respectively. The poppet body 52 also has a charging volume groove 72, preferably positioned between the second o-ring groove 62 and the third o-ring groove 64. First o-ring groove 60, second o-ring groove 62, third o-ring groove 64, and charging volume 72 all consist of geometry which is circumferential to valve poppet 32, which is generally cylindrical in shape. O-rings 66, 68 and 70 are all made preferably of urethane, which is compatible with high-pressure carbon dioxide or other delivery gas or combination of gases.

Although o-rings are preferred, it will be understood that other alternative sealing means known in the art may also be used to eliminate leakage of gas from the canister conduit 44 into poppet chamber 46 and out of the apparatus.

Referring more particularly to FIG. 5, it can be seen that when valve poppet 32 is in the rest position, as shown, the internal gas pressure of carbon dioxide canister 28 is in fluid communication with charging volume 72 and the space between poppet 32 and the walls of poppet chamber 46, between o-rings 68 and 70 through canister conduit 44, resulting in charging volume 72 being filled with carbon dioxide to the same pressure that is in carbon dioxide canister 28. The contents of carbon dioxide canister 28, and charging volume 72, is prevented from escaping around the valve poppet 32 into the ambient environment primarily by second o-ring 68 and third o-ring 70 that seal the sections of the chamber 46 between the o-rings.

As valve poppet 32 is moved into the actuated position, as shown in FIG. 6, second o-ring 68 passes over canister conduit 44, preventing further fluid communication between carbon dioxide canister 28 and charging volume 72, and third o-ring 70 is caused to pass over valve exit conduit 74, thus releasing the pressurized gas in charging volume 72 through valve exit conduit 74 to valve exit port 76. Second o-ring groove 62 and third o-ring groove 64 are preferably spaced apart from charging volume 72 so that the second o-ring 68 terminates fluid communication between carbon dioxide canister 28 and charging volume 72 prior to the third o-ring 70 passing over valve exit conduit 74, thus preventing the contents of carbon dioxide canister 28 from ever being in fluid communication with valve exit conduit 74 and valve exit port 76, and creating a burst of pressurized gas to be released from charging volume 72.

Obviously, charging volume 72 may be sized for different volumes allowing for different amounts of gas such as carbon dioxide to be released with each actuation. It will also be seen that first o-ring 66 prevents escape of contents of carbon dioxide canister 28 around valve poppet 32 into the ambient environment when valve poppet 32 is in the actuated position.

Figure 7:
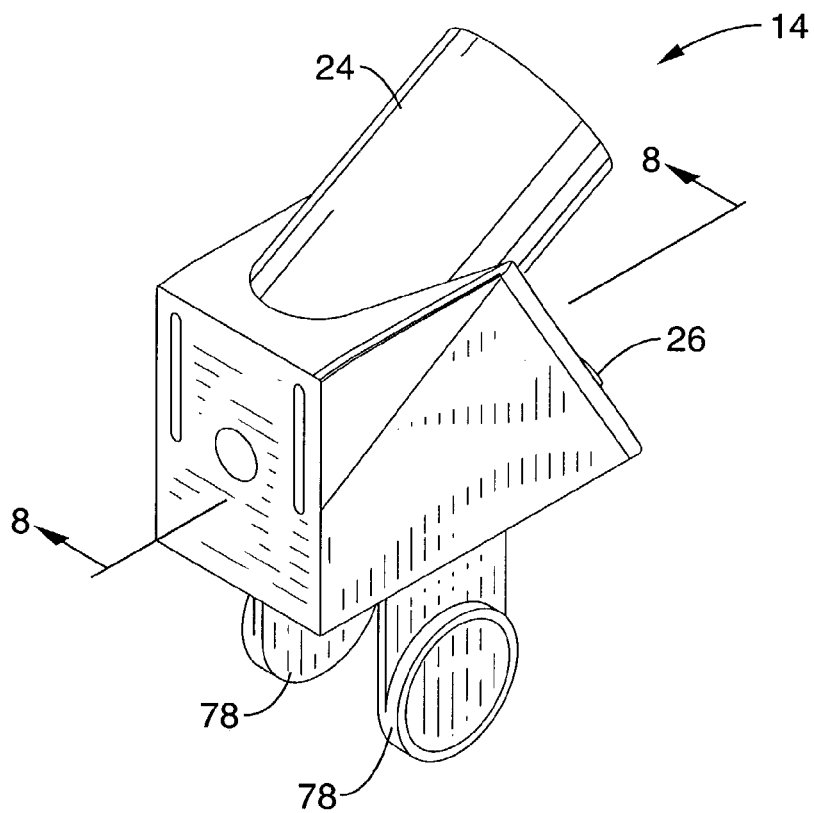
FIG. 7 is a perspective view of the aerosol generator portion of the inhaler of FIG. 1.
Figure 8:
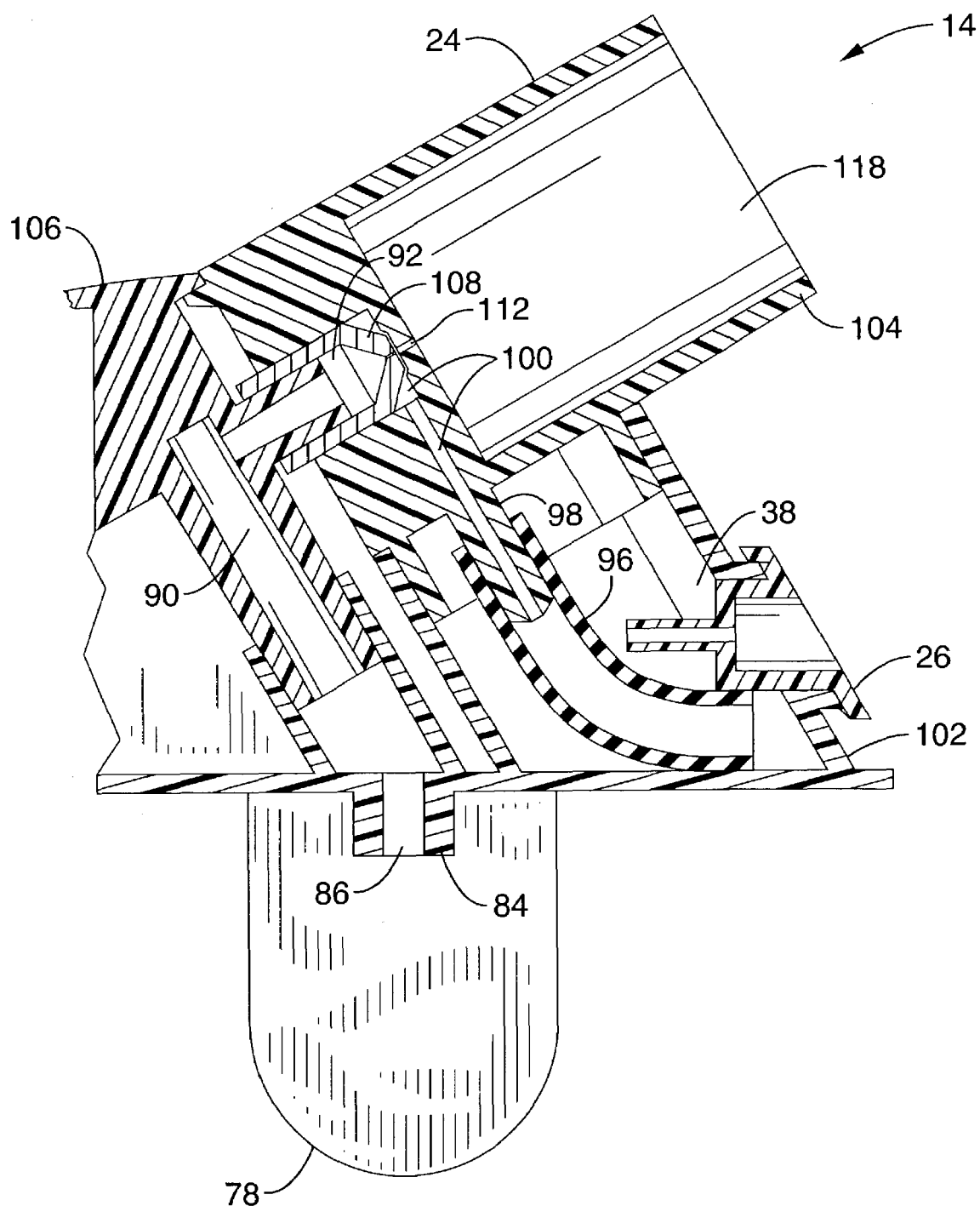
FIG. 8 is a detail side view in cross-section of the aerosol generator of FIG. 7 taken along the lines 8—8 of FIG. 7.

As shown in FIG. 1, FIG. 2, and FIG. 3, aerosol generator 14 is caused to mate with actuator handle 12. As seen in FIG. 7 and FIG. 8, aerosol generator 14 has a pair of locking tabs 78 that pass through corresponding tab slots 80 and snap into tab receptacles 82, as shown in FIG. 4. When locking tabs 78 on aerosol generator 14 are fitted into tab receptacles 82 of actuator 12, inlet stem 84 of FIG. 8 is configured to fit to valve exit port 76 of actuator 12 as seen in FIG. 4, FIG. 5, and FIG. 6. Inlet stem 84 is mated with valve exit port 76 of actuator 12 such that sealing is established between the base of inlet stem 84 and actuator outlet o-ring 88 of FIG. 6. This allows for fluid communication between valve exit port 76 of actuator 12 and inlet stem 84 of aerosol generator 14 via valve exit conduit 74 of FIG. 6 and supply inlet 86 of FIG. 8.

Figure 9:
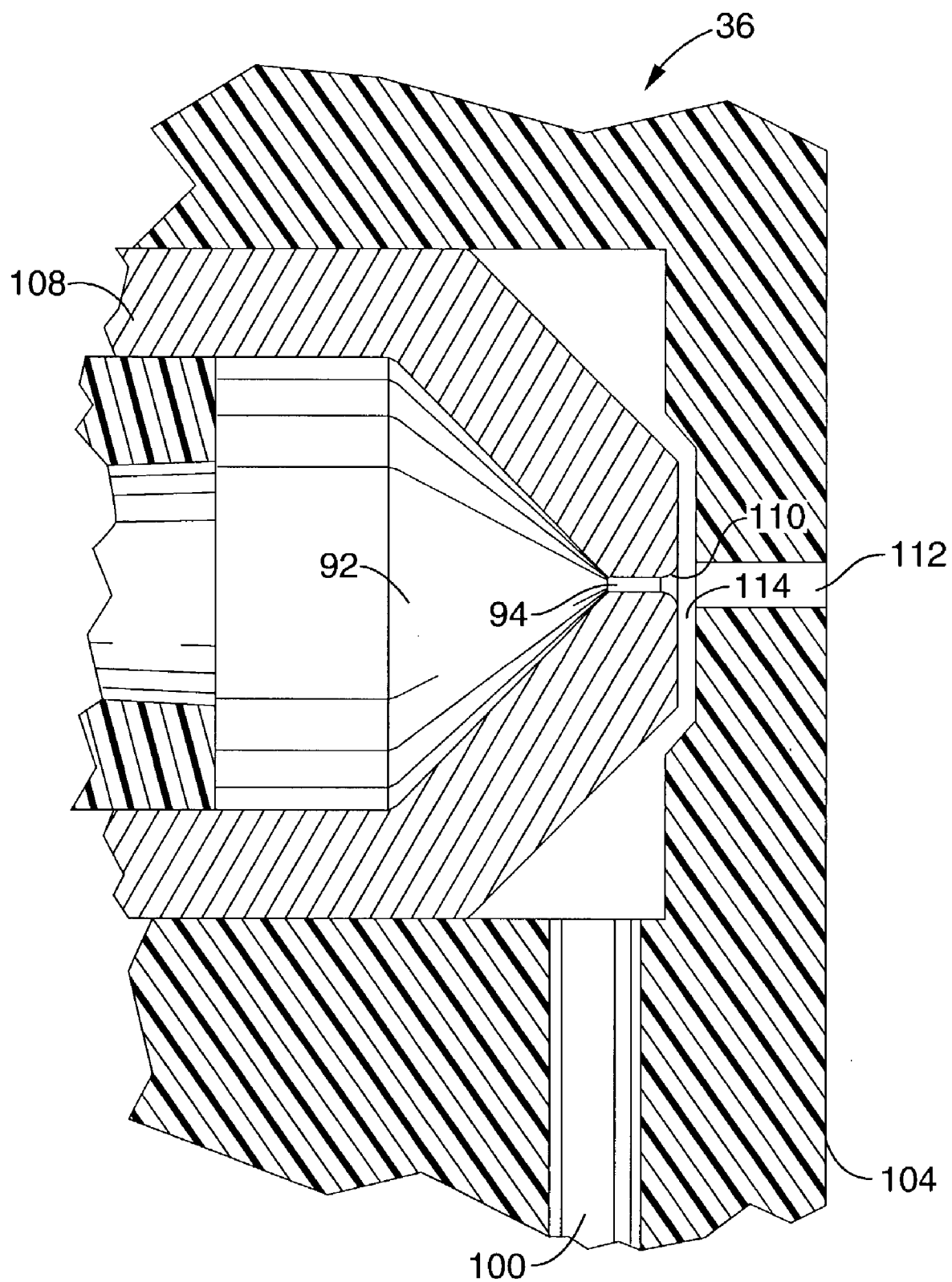
FIG. 9 is a detail side view in cross-section of the nozzle portion of the aerosol generator of FIG. 7 and FIG. 8.

Referring now to FIG. 8 and FIG. 9, it can be seen that the metered volume of compressed gas received from the actuator 12 through supply inlet 86 of inlet stem 84, passes into supply channel 90 and proceeds into insert supply cavity 92 and out of the aerosolization nozzle through jet orifice 94 and shock chamber 112.

In the embodiment shown, reservoir 38 of aerosol generator 14 preferably has a liquid feed tube 96 mounted to liquid feed stem 98 that has a medicine channel 100 that is in fluid communication with the aerosolization assembly 36 as seen in FIG. 8 and FIG. 9. Thus, liquid entrained for aerosolization from reservoir 38 is caused to travel up liquid feed tube 98, through medicine channel 100 of liquid feed stem 98 and directly to the nozzle section of the aerosolization nozzle assembly 36, which is shown in the enlarged detailed view of FIG. 9.

In one embodiment, the channel 100 may be sized or have an orifice that will restrict the flow of material through channel 100 traveling to the nozzle assembly 36. This regulation of the volume of material or the rate of material introduced has been shown to increase the efficiency of the aerosol process. Any restriction between the reservoir and the shock chamber would potentially serve the same purpose.

In the embodiment shown in FIG. 8, aerosol generator 14 is made of reservoir base 102, mouthpiece 104, elbow 106 and nozzle insert 108 components. In this embodiment, the aerosol generator 14 is assembled by placing liquid feed tube 96 on liquid feed stem 98 of mouthpiece component 104. Insert 108 is placed into the back of mouthpiece 104 creating the critical nozzle geometry shown in FIG. 9 where aerosolization occurs. Elbow 106 is placed into backside of insert 108 and then the assembly consisting of mouthpiece 104, insert 108 and elbow 106 are coupled with reservoir base 102. Plug 26 is then placed into reservoir component 102. Bonding between mating pieces may be established using press fits, adhesive techniques, or ultrasonic welding, except for mating between plug 26 and reservoir base 102, which is intended to be a sliding fit.

Liquid medication intended for aerosolization is placed in reservoir 38 by removing plug 26 and placing the medication directly into the liquid storage cavity of reservoir 38. Various liquid medications may be placed in the reservoir, as desired. In one embodiment, the liquid storage cavity of reservoir 38 contains a total volume of at least twice the intended liquid volume to be dispensed. This allows for the prevention of spilling of the contents of the liquid storage cavity of reservoir 38 and for different orientations of the aerosol generator 14.

An alternative to having a reservoir 38 for storing of medication for multiple doses, as above described, is to have means by which one dose may be made available to the aerosolization nozzle 36 at a given time. This would be the preferred embodiment of the current invention for medication requiring very strict output control or which requires special handling and storing, such as refrigeration. Strict output control would be realized because the aerosolization assembly 36 is designed so that it always attempts to entrain more liquid than there is present in the single dose reservoir. In this way, output is controlled solely by what is in the reservoir and not the critical dimensions of the aerosolization nozzle assembly 36 or the contents of carbon dioxide canister 28.

There exists many ways to have single dose reservoirs, including a very small version of the previously described liquid storage cavity 38, single ampules, or blister packs. A single dose may also include multiple puffs until the medication in the reservoir or ampule is depleted. In the case of ampules or blister pack cells, the liquid feed tube 96 would preferably be made from stiff plastic and would puncture the ampule or blister pack cell when entrainment was desired. After actuation, the empty ampule would be discarded, or, in the case of the blister pack, the liquid feed tube 96 would be advanced to the next blister pack cell when another dose of aerosol was required.

Still referring to FIG. 8, carbon dioxide gas supplied to supply inlet 86, is caused to pass up supply conduit 90 and into insert supply cavity 92. Referring also to FIG. 9, pressurized carbon dioxide gas that is provided to insert supply cavity 92 is then caused to pass into jet orifice 94 with exit plane radius 110. In the preferred embodiment, jet orifice 94 has a diameter ranging from approximately 0.008 inches to approximately 0.016 inches, and exit plane radius 110 preferably has a diameter ranging from approximately 0.010 inches to approximately 0.020 inches. Although the exit plane radius with these dimensions is preferred, any exit plane radius providing a characteristic jet can be used.

Because the supply pressure of the carbon dioxide canister is normally approximately 750 psig, the jet formed in the jet orifice 94 will go supersonic. The jet will remain supersonic until such time that the cross sectional area of the exit area, due to exit plane radius 110, becomes too large, at which point the jet will be over expanded and reflected shock waves will form in the jet as shown graphically in FIG. 10 and schematically in FIG. 11. The diamond-shaped patterns of FIG. 10 and FIG. 11 show the shock wave patterns in the supersonic jet.

In the preferred embodiment of the present invention, exit plane radius 110 is large enough to insure that the supersonic jet formed from jet orifice 94 is over expanded. This will cause the first series of reflected shock waves to be compression shock waves rather than expansion shock waves. Although expansion shock waves are capable of aerosolization, compression shock waves have been shown to be more effective than expansion shock waves at aerosolization.

In an alternative configuration in which reflected expansion waves are desired initially, exit plane radius 110 would be made small enough, removed, or replaced with an appropriate taper, so that the exiting supersonic jet from jet orifice 94 was under expanded.

The supersonic jet exiting the jet orifice 94 and associated exit plane radius 110 will travel linearly down the central axis of shock chamber 112 and into the confines of mouthpiece 24. In the preferred embodiment, shock chamber 112 has a diameter ranging from approximately 0.020 inches to approximately 0.030 inches, or two to three times the diameter of the jet orifice 94. The resulting reflecting shock waves will continue along with the jet well outside the exit plane of shock chamber 112. Optimally, interstitial space 114 has a gap distance between the exit plane and jet orifice 94 and the inlet of shock chamber 112 of between approximately 0.007 inches and 0.016 inches.

In general, the minimum pressure required to achieve supersonic flow in a nozzle with jet orifice 94 is dependant upon the ambient discharge pressure and the supply pressure such that the ratio of the two should preferably be at least 0.5283 for air or oxygen and at least 0.5457 for carbon dioxide. Since all known inhalers have always discharged into roughly atmospheric conditions (14.7 psi), the resulting minimum supply pressure can be determined as being approximately equal to 27.8 psi or 13.1 psig for air or oxygen and approximately 26.9 psi or 12.2 psig for carbon dioxide. In theory, these minimum gas supply pressures are sufficient to produce a flow of gas through the throat of a nozzle 94 with a velocity equal to the speed of sound. In practice, to produce shock waves with sufficient strength to cause aerosolization higher pressures are required, other factors which make higher supply pressures more practical include pressure losses and the expansion of gas into the internal volume of the device between the supply canister 28 containing the stored gas and the cavity 92 of the nozzle assembly 36. Although lower gas pressures will produce a degree of aerosolization, superior results are achieved with even higher gas pressures or continual increases in output for higher pressures. The increase in output for higher pressures is due to the increasing speed of the supersonic jet and the resulting increase in strength of the resulting shock waves.

Supersonic jets produce shock waves in part because the jets do not expand gradually to the diameter of the shock chamber. Due to the nature of the fluid dynamics involved, and conservation of momentum, supersonic jets expand by producing shock waves, thus producing an extreme change in pressure from one side of a shock wave to the other. Unlike other exiting flow patterns, supersonic jets, through the dynamics of the shock waves, maintain roughly the same diameter that the jets had as they exited from the nozzle from which the jets were produced. Similarly, vacuum and entrainment of liquid is not primarily due to the Bernoulli principle, but more to boundary layer friction between the exiting jet and the surrounding gas in the shock chamber 112.

It will be seen that any nozzle which supplies a compressed gas to the nozzle orifice at pressures above the calculated minimums will have a supersonic jet exiting from it which is either over, under, or perfectly expanded, provided that there is nothing present to disturb the jet, such as too much liquid material introduced to the jet. A nozzle may achieve a jet with a velocity that is greater than the speed of sound if it is supplied with sufficient supply pressure and has a gradually increasing cross-sectional area downstream of the throat or choke. The potential increase in jet velocity with increasing cross-sectional area is dependant on the total supply pressure.

For the perfectly expanded supersonic jet, the cross-sectional area of the jet is increased to the maximum that is possible for the given gas supply pressure, resulting in a supersonic jet with a shock wave entirely enveloping the jet. Although this is ideal for the production of aerosol, it is often impractical in practice because of variances in the gas supply pressure and the dimensional tolerances that are required in the nozzle assembly.

An under expanded supersonic jet has a maximum cross-sectional area which is less than the perfectly expanded supersonic jet. The extreme example of an under expanded jet is a simple orifice 94 with no increasing cross sectional area. The result of a under expanded supersonic jet is a series of expansion and compression reflected shock waves, with the first shock waves immediately after the exit of the jet being expansion waves.

An over expanded supersonic jet has a maximum cross sectional area which is greater than the maximum cross sectional area of the perfectly expanded supersonic jet. The result is also a series of reflected compression and expansion shock waves. In one embodiment, an over expanded supersonic jet is instigated by placing a large radius on the exit edge of the nozzle. Upon the jet traveling through the throat and then subsequently along the radius, the initial response is for the jet to increase to a speed greater than the speed of sound followed by an over expansion of the jet, which will produce reflected shock waves.

Referring back to FIG. 8 and FIG. 9, upon the initial formation of the supersonic jet, a vacuum will be created in interstitial space 114, which is in fluid communication with the medicine channel 100, thus causing liquid medication to be entrained from reservoir 38 through liquid feed tube 96, stem 98, channel 100 and introduced into shock chamber 112. Liquid stripped from interstitial space 114 initially forms droplets, that are too large to be classified as aerosol. Upon entrainment into the jet, droplets become exposed to the large differentials in pressure and velocity that exist across a shock wave. These large differential pressures and velocities cause significant stretching of the droplet, thus increasing it's surface area. Due to the surface tension of liquid, droplets resist having their surface area increased and, when stretched sufficiently, will break apart to form multiple other smaller particles. The aerosol burst is carried out of the shock chamber 112 along with the expelled gas to mouthpiece 24. Subsequent to the initial fluid being introduced to shock chamber 112, the integrity of supersonic jet and resulting shock waves are destroyed due to the ongoing entrainment of more liquid, although shock waves are still present immediately proximal to the exit plane of jet orifice 94 and exit plane radius 110. The duration of the shock waves can be affected by restricting the flow of liquid such that the Accordingly, the charging volume 72 is preferably made large enough so as to deliver enough carbon dioxide gas to give the jet time to form, entrain liquid, and create the desired burst of aerosol. Once the carbon dioxide that is delivered from charging volume 72 to the jet orifice 94 is depleted, the jet ceases to exist all together, and no more liquid is entrained.

Figure 12:
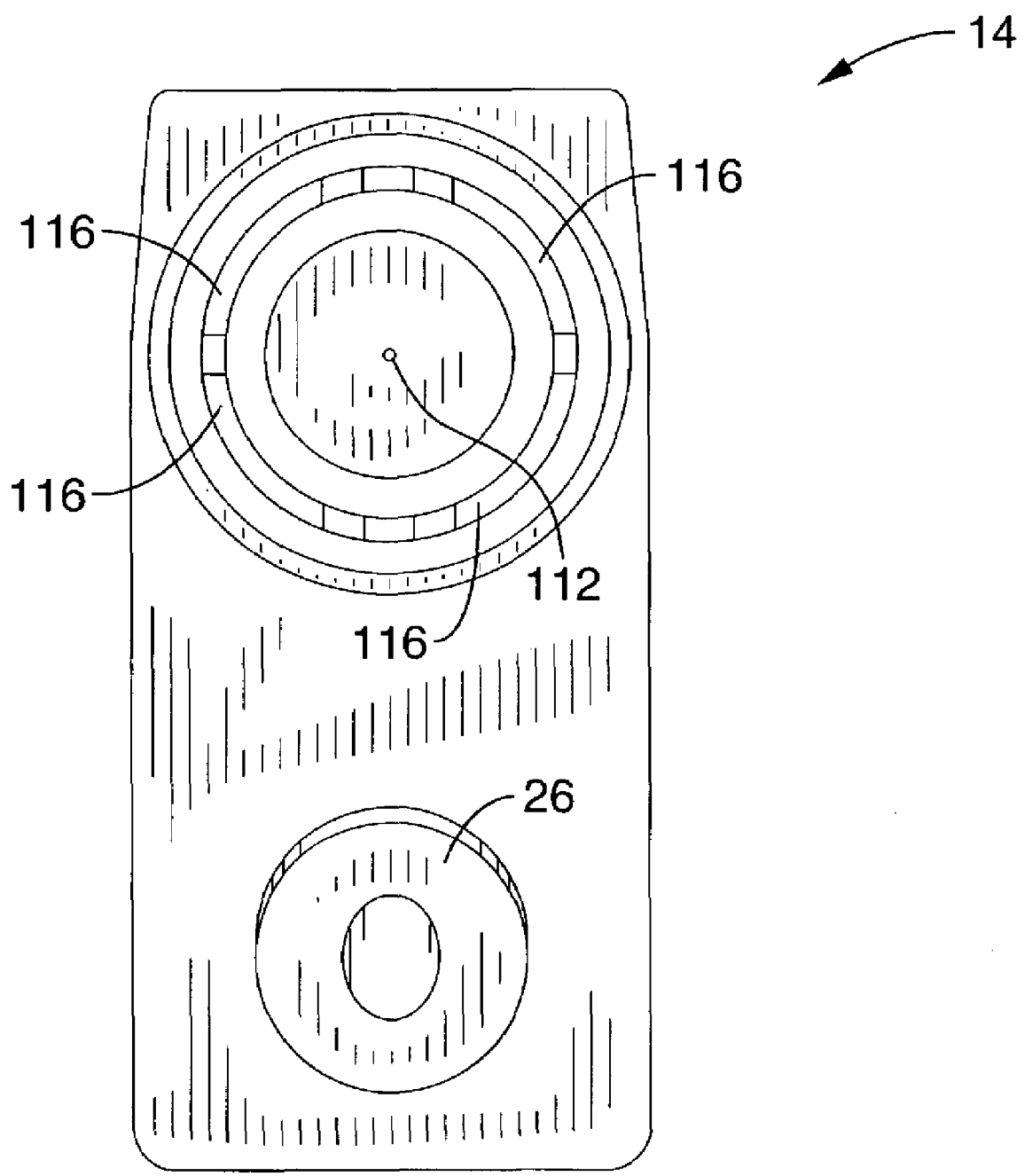
FIG. 12 is a front view of aerosol generator of FIG. 7 showing the mouthpiece and plug.

Referring also to FIG. 12, the aerosol exiting shock chamber 112 is carried into the internal cavity 118 of mouthpiece 24 where it is available for immediate inhalation by the patient. FIG. 12 is a view of the aerosol generator 14 looking directly down the internal cavity 118 of mouthpiece 24, the backside of the internal cavity 118 of mouthpiece 24 is preferably equipped with four entrainment ducts 116, which allow ambient air to be entrained when the patient inhales. The diameter of the mouthpiece internal cavity 118 and the cross-sectional area of the four entrainment ports 116 are the primary means of controlling the geometry and speed of escaping aerosol 120 from shock chamber 112 shown in FIG. 10.

The length of the mouthpiece 24 and its internal cavity 118 also plays a role in the speed of escaping aerosol. Accordingly, the length of mouthpiece 24 is reduced to a minimum to prevent as much waste of aerosolized medication 120 as possible. In the current preferred embodiment, the mouthpiece internal cavity 118 has a diameter of approximately 0.775 inches and the preferred cross-sectional area of the four-entrainment ducts 116 is approximately 0.08 inches squared or 0.02 inches square for each duct 116. Reducing the cross-sectional area of the four-entrainment ducts 116 has been shown to reduce the exit velocity of the resulting aerosol if desired. Additionally, in an alternative embodiment, spacers and valve holding chambers are well known in the industry and can be connected directly to the outer diameter of mouthpiece 24.

Referring now to FIG. 13 through FIG. 30, an alternative embodiment of the invention is shown. As seen in FIG. 13, this embodiment comprises three principal parts: a reusable actuator handle 200, a disposable aerosol generator 202 and a disposable carbon dioxide cartridge assembly 204.

Figure 20:
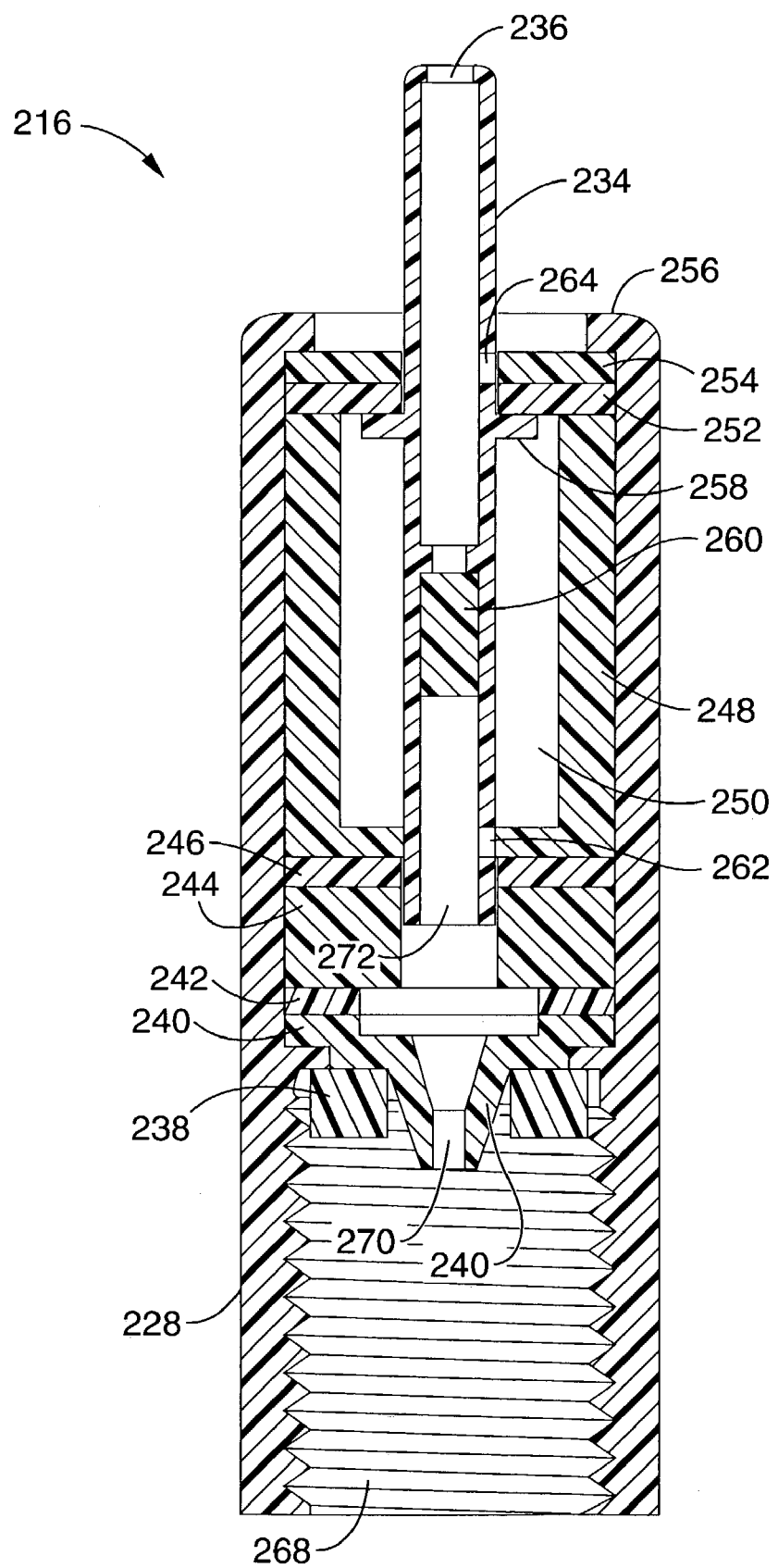
FIG. 20 is a side view in cross-section view of the valve of FIG. 18.
Figure 21:
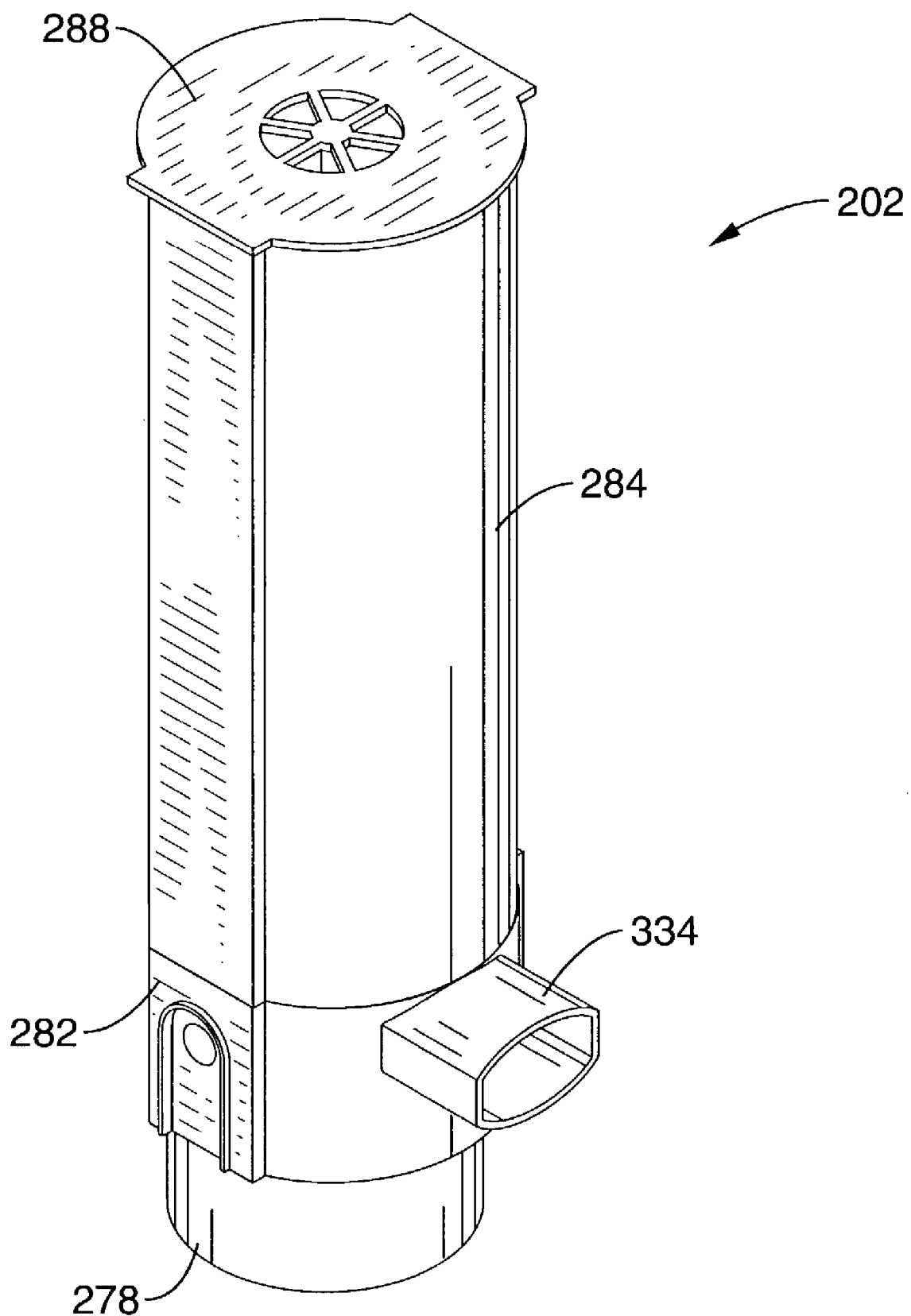
FIG. 21 is a perspective view of the disposable inhaler aerosol generator portion of the inhaler embodiment of FIG. 13.

Turning now to FIG. 14 and FIG. 15 the gas supply (carbon dioxide) cartridge assembly 204 can be seen. The cartridge assembly 204 comprises a gas canister 206 and gas canister cap 208. The carbon dioxide gas canister 206 preferably includes a top 210 with threads 268 that is configured to engage with corresponding threads 266 within a valve assembly contained in actuator handle 200 as seen in FIG. 14 and FIG. 20. Although a gas canister 206 is preferred and used for illustration, it will be understood that other sourced of gas supply known in the art such as compressors or pumps and the like may be used as a source of compressed gas.

Carbon dioxide gas represents only one of many different types of gases that may be used to power the current invention. Although carbon dioxide gas is preferred, it will be understood that any appropriate pressurized gas or combinations of gasses can be used. In one embodiment, gas canister 206 is bonded to the gas canister cap 208 with an adhesive and is designed with a large diameter to allow for sufficient torque during insertion of the carbon dioxide cartridge 206 into actuator handle 200. Carbon dioxide cartridge 206 preferably fits longitudinally into the underside of actuator handle 200 through cartridge port 212.

Turning now to FIG. 16 through FIG. 19, the components of the actuator handle 200 of the embodiment of FIG. 13 are shown. Actuator handle 200 has an elongate actuator body 214 with cartridge port 212 at the bottom end. The actuator handle also includes a valve assembly 216, valve stem cover 218, trigger 220, and trigger pivot pin 222 as seen in the exploded view of FIG. 17.

Valve stem cover 218 has a pair of valve stem cover bosses 224 that engage angled edges 226 of trigger 220 such that when trigger 220 pivots about pin 222 the valve stem cover 218 moves longitudinally within handle body 214. Accordingly, when assembled, valve stem cover 218 mates with valve assembly 216 and the bosses 224 engage with trigger 220 such that when trigger 220 is squeezed, trigger cam surface 226 engages with valve stem bosses 224 such that valve stem cover 218 is forced to move downward causing valve assembly 216 to become actuated as described herein.

Figure 17:
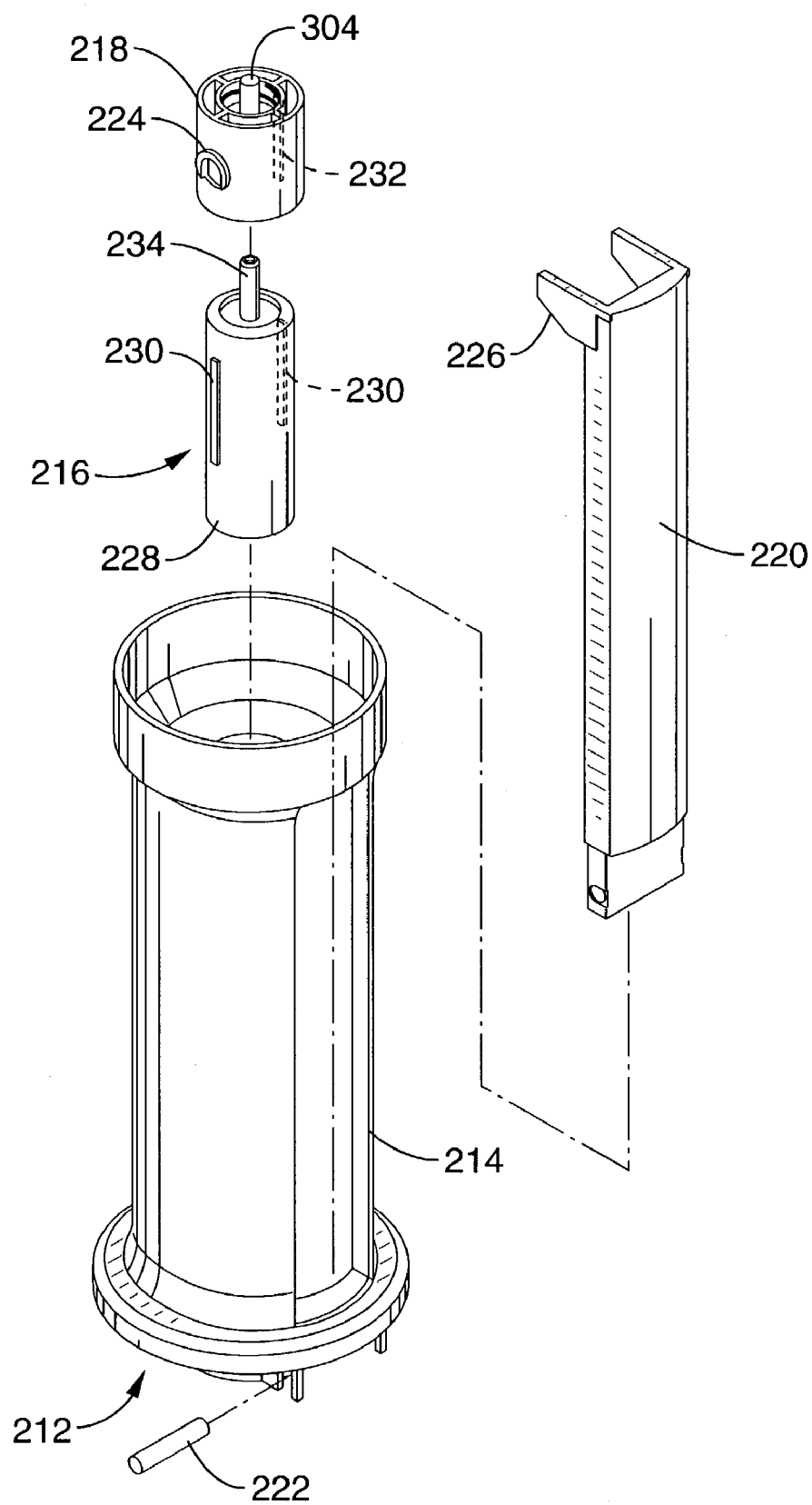
FIG. 17 is an exploded view of the reusable actuator of FIG. 16.
Figure 18:
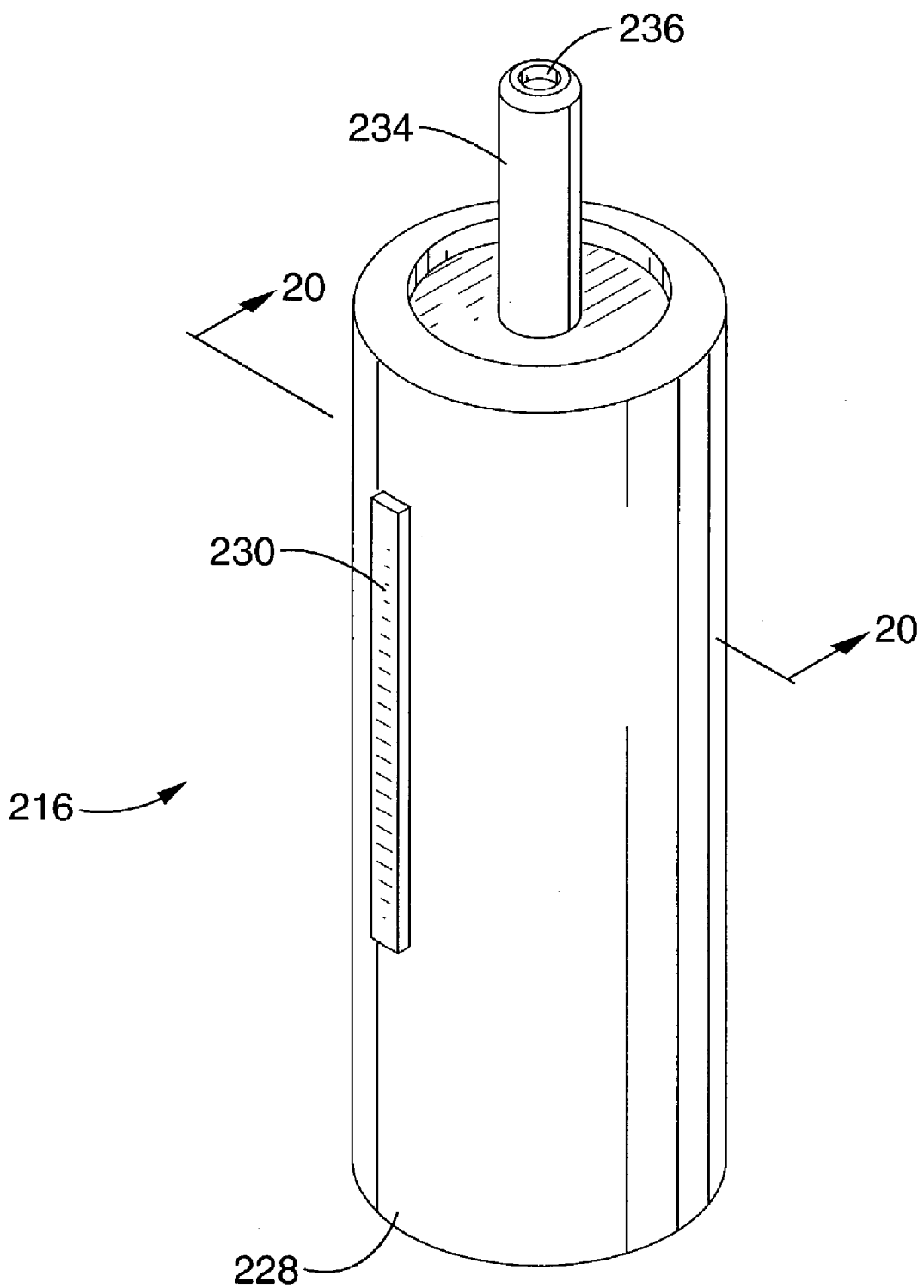
FIG. 18 is a perspective view of the valve portion of the inhaler of FIG. 13 and FIG. 17.
Figure 19:
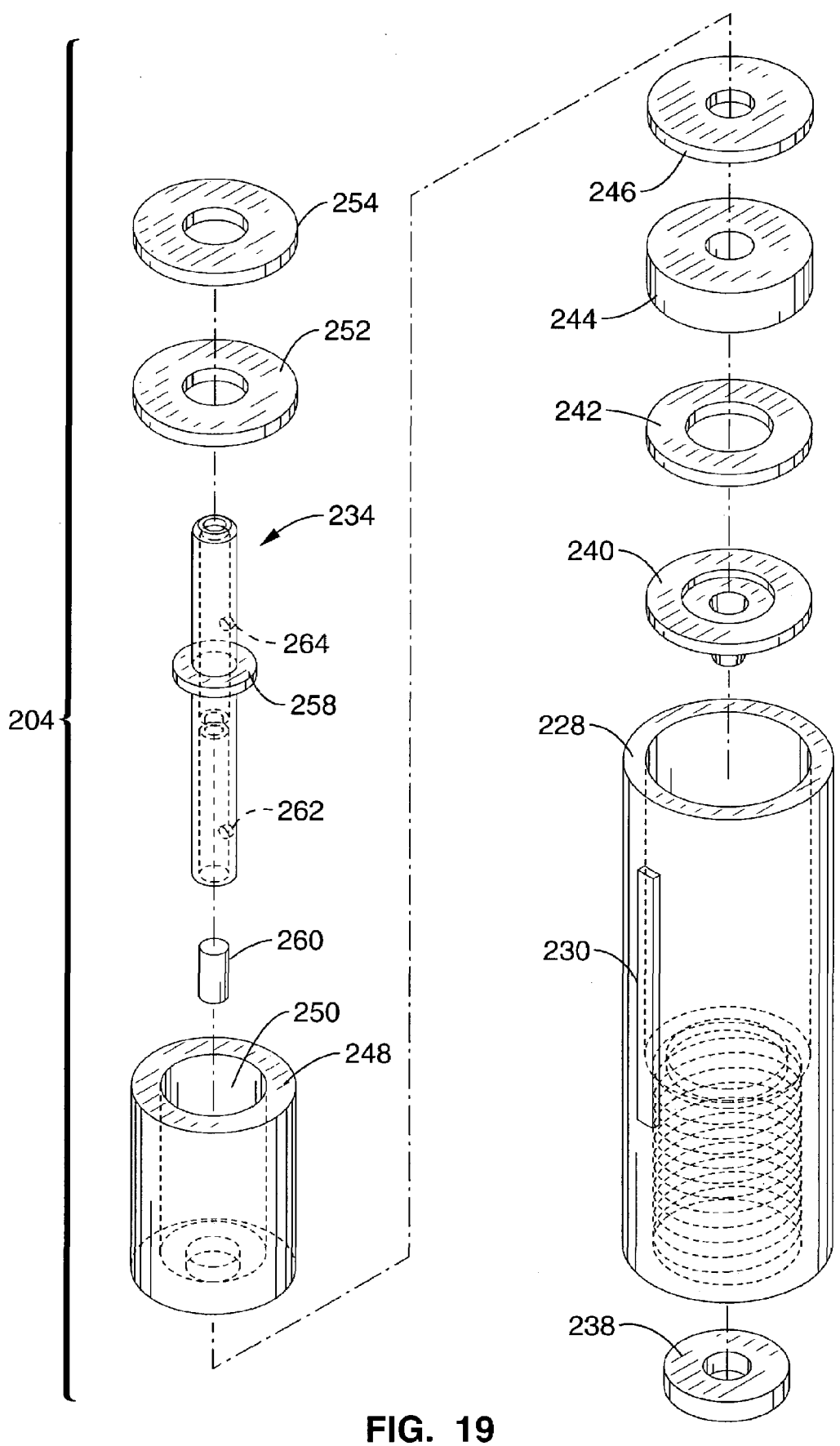
FIG. 19 is an exploded view of the valve of FIG. 18.

Referring also to FIG. 18, FIG. 19 and FIG. 20, the components of one embodiment a valve assembly 216 are shown. Valve assembly 216 has a generally cylindrical body 228 that is configured to fit within actuator handle 200 as seen in FIG. 17 and FIG. 18. In this embodiment, valve assembly body 216 has one or more raised rails 230 on the outer surface that slide within corresponding slots in the interior of the handle 200 (not shown) as well as slots 232 in valve stem cover 218. The raised rail 230 and slot configuration securely positions the valve assembly and eliminates any rotational motion of the valve assembly 216 when the threads 268 of the top 210 of gas canister 206 are screwed into the threads 268 of the valve assembly. Rails 230 also facilitate the linear movement of the valve stem cover 218 with respect to the valve assembly 216 when the trigger 220 is pressed.

Referring now to the exploded view of the valve assembly 216 in FIG. 19 and the cross sectional view of FIG. 20, the regulation of the flow of gas from the canister 206 through the stem exit port 236 can be seen. In the embodiment shown in FIG. 19, the valve assembly 216 has a canister seal 238, valve body 228, hollow canister puncture pin 240, puncture pin valve seal 242, valve spacer 244, central valve seal 246, cylinder 248 with chamber 250, stem plug 260, valve stem 234, top valve seal 252, and end plate 254. The exploded view in FIG. 19 shows the relative position of each of these components. The cross sectional schematic view in FIG. 20 shows the relative position of the components when assembled.

Seals 238, 242, 246 and 252 as well as stem plug 260 are preferably made of urethane, due to the resistance of this material to react with compressed carbon dioxide. Valve spacer 244 and cylinder 248 are preferably made of injected molded nylon. Valve body 228, canister puncture pin 240, valve stem 234, and end plate 234 are preferably made of machined aluminum but may also be made of glass-reinforced nylon. In the embodiment shown, the parts are assembled as shown in FIG. 19 and then valve body end 256 is rolled over in a machining operation to keep the parts in place.

Referring now to FIG. 20, the regulation of the gas flow and the movements of the valve components of one embodiment of the valve assembly can be seen. Valve stem 234 can move axially within chamber 250 of cylinder 248. A circumferential flange 258 on stem 234 stops the outward movement of stem 234 by engaging the interior side of the top valve seal 252. Valve stem 234 is tubular and has a plug 260 in the approximate center of the stem. In addition, stem 234 has a valve stem inlet orifice 262 and a valve stem exit orifice 264 that communicate from the interior of the stem 234 to the exterior.

When the top 210 of carbon dioxide canister 206, for example, is advanced on threads 266 of the valve assembly body 228, the top of canister 206 will engage hollow puncture pin 240, which pierces the top 206. The top 210 of carbon dioxide canister 206 is caused to seat against canister seal 238 as the threads 269 of canister 206 are advanced along the threads 266 of the valve body.

Once seated, carbon dioxide becomes available to valve assembly 216 through canister puncture pin channel 270. The valve assembly 216 in the normally closed position is shown in FIG. 20. In this position, valve stem 234 is pushed by the pressure of the compressed carbon dioxide gas so that valve stem flange 258 is caused to seal against the upper valve seal 252.

In the closed position, carbon dioxide is allowed to pass from the canister 206 through pin channel 270, valve seal 242 and valve spacer 244 to valve stem inlet port 272 located at the proximal end of stem 234. Gas within stem 234 must exit the stem through inlet orifice 262 because of plug 252 to fill the chamber 250 of cylinder 248 that exists between the outer diameter of valve stem 234 and the inner diameter of valve cylinder 248. Valve seals 246 and 252 are sized on the internal diameters to fit and seal against the outer diameter of valve stem 234. In the closed position, chamber 250 ultimately becomes filled with carbon dioxide gas to the same pressure as that of canister 206.

In the open position, valve stem 234 is moved linearly, against the force of the internal pressure, toward the canister 206. It will be seen that when stem 234 is moved downwardly, valve stem inlet orifice 262 is caused to pass by central valve seal 246 thereby disconnecting fluid communication between the carbon dioxide pressure provided by the carbon dioxide cartridge 206 and interstitial space of chamber 250. Further motion of valve stem 234 causes valve stem exit orifice 264 to pass through top valve seal 252 allowing the compressed gas in chamber 250 to exit the chamber through stem exit orifice 264 to the interior of valve stem 234 and out through valve stem exit port 236. In the preferred embodiment, the volume of gas that is discharged through stem exit port 236 is predictable and consistent for each actuation event and is determined by the relative internal volumes of jet 274 and the volume of chamber 248. When the stem 234 is returned to the normally closed position, the chamber 250 refills and becomes ready for the next actuation.

Turning now to FIG. 21 through FIGS. 28, 31 and 32, the preferred aerosol generator component of the present invention is described. As seen in the exploded view of FIG. 22, the preferred aerosol generator 202 comprises a jet 274, secondary 276, reservoir cup 278, cap 280, column base 282, column 284, flapper valve 286, and column end 288.

Figure 16:
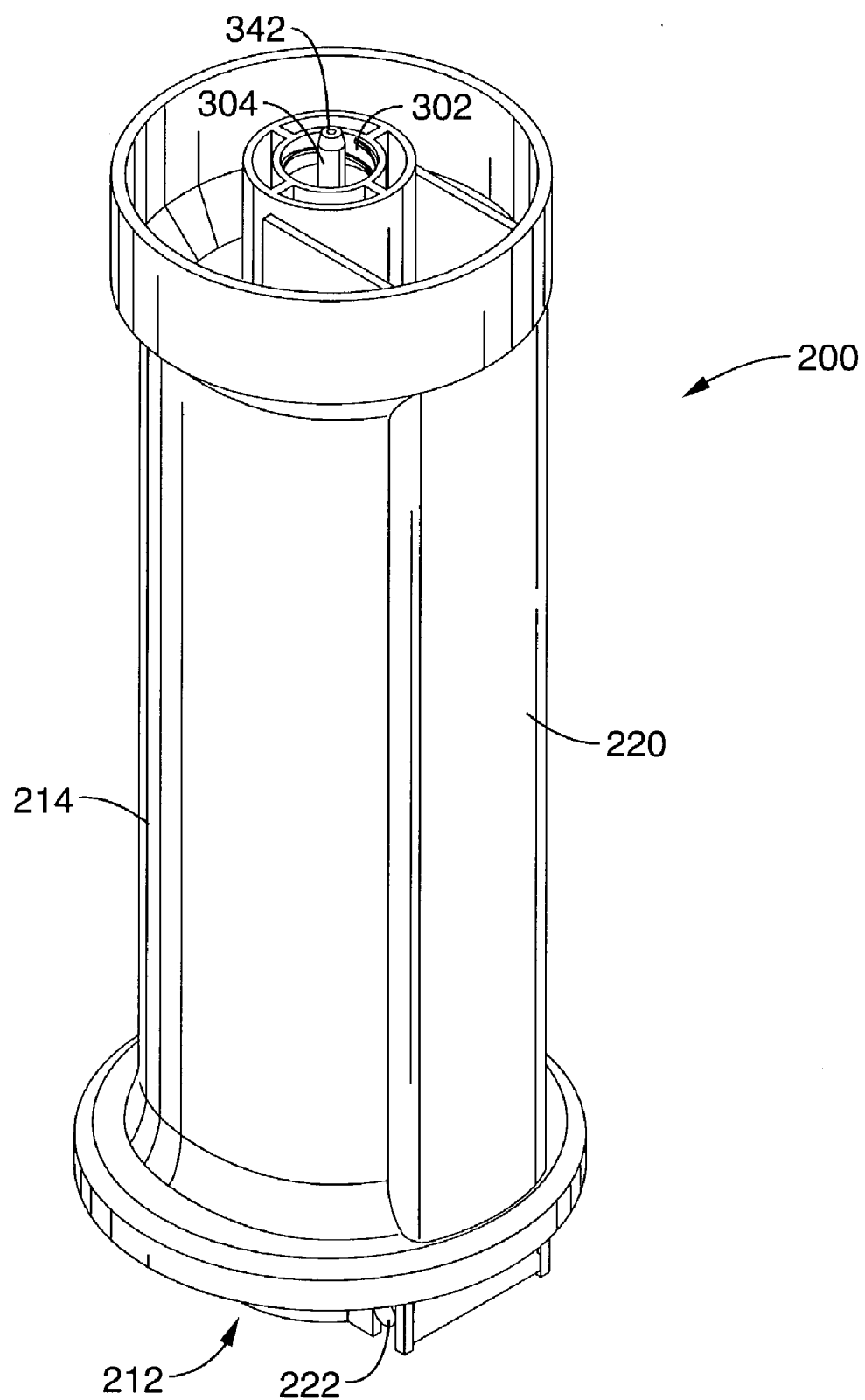
FIG. 16 is a perspective view of the reusable inhaler actuator portion of the inhaler of FIG. 13.
Figure 23:
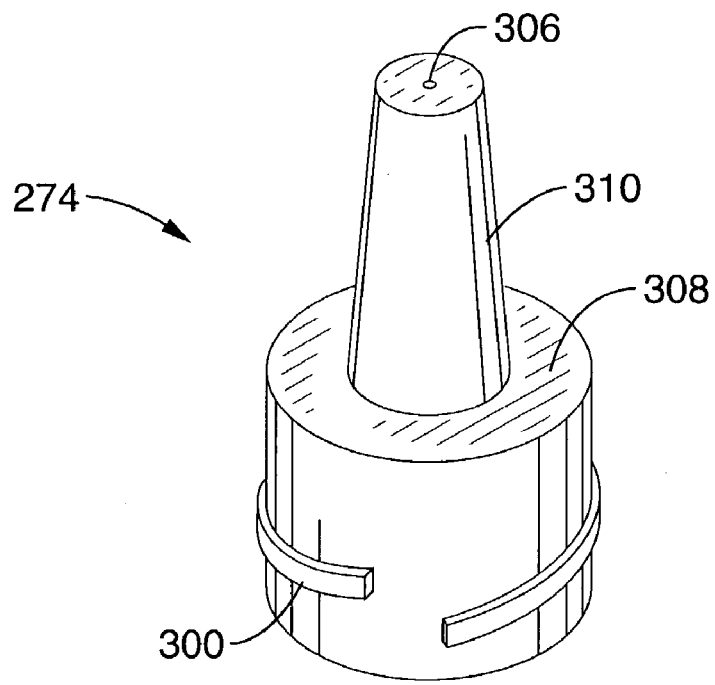
FIG. 23 is a perspective view of the jet employed in the inhaler of FIG. 13 and FIG. 22.

The jet 274, shown in FIG. 23, has a set of external threads 300 that allow the aerosol generator 202 to fit onto actuator handle 200 through the engagement of threads 300 with the corresponding threads 302 of valve stem cover 218 as shown in FIG. 16. The distal end of valve stem 234 mates with the inside diameter of valve stem cover 218 to provide an adequate seal. The interior of jet 273 is configured to receive valve stem cover exit port 304 when the external threads 300 of jet 274 are coupled with the valve stem cover 218. Jet 274 also has a jet orifice 306 that allows the flow of gas received from exit port 236 from valve stem 234 through valve stem cover exit port 304.

Figure 24:
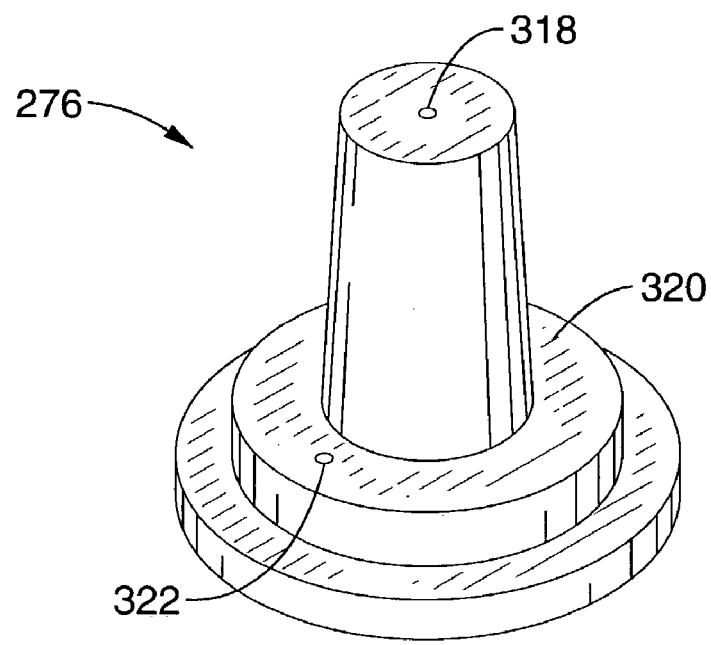
FIG. 24 is a perspective view of the top side of the secondary employed in the inhaler of FIG. 13 and FIG. 22.
Figure 25:
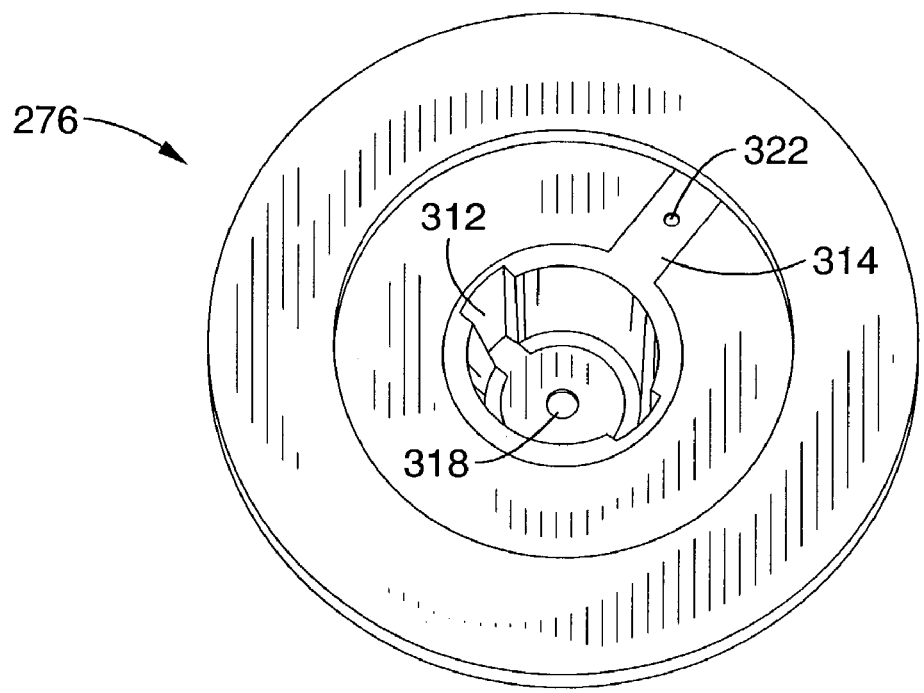
FIG. 25 is a perspective view of the bottom side of the secondary shown in FIG. 24.
Figure 31:
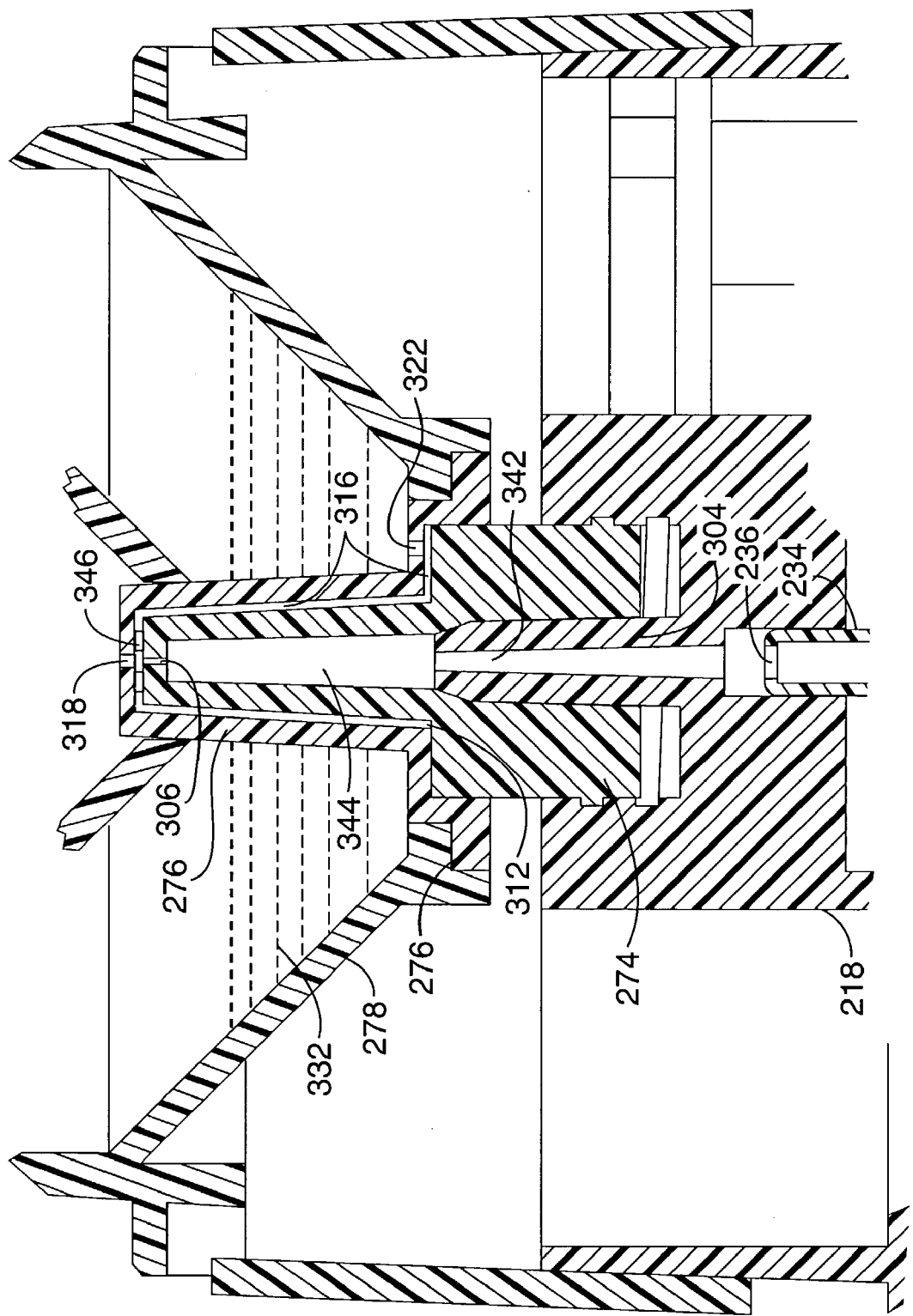
FIG. 31 is a detail side view in cross-section of the supersonic nozzle assembly portion of the inhaler of FIG. 13.

Jet 274 and the secondary 276 shown in FIG. 24 interlock together such that the external surfaces 308, 310 of jet 274 and the internal surfaces of secondary channels 312, 314 of secondary 276, seen in FIG. 25, to form interstitial fluid passages 316 seen in FIG. 31.

Secondary 276, shown in FIG. 24 and FIG. 25 also has an opening 318 that operates as a shock chamber. As in the previously described embodiment, jet orifice 306 mates with secondary 276 such that the shock chamber 318 and jet orifice 306 are aligned to form the shock wave aerosolization nozzle, and preferably have the same nozzle dimensions as described in the first embodiment.

Secondary 276 fits into the bottom of reservoir cup 278 to form a reservoir for the holding of liquid medication such that secondary surface 320, shown in FIG. 24, preferably becomes the lowest point of the liquid reservoir. Penetrating through surface 320 through to secondary channel 314 is liquid choke orifice 322. Liquid choke orifice 322 provides further means, through the resistance of the flow of liquid, for limiting the rate and amount of liquid entrained by the shock wave aerosolization nozzle. The preferred optimum size range for liquid choke orifice 322 is less than approximately 0.050 inches. By further choking the flow of liquid down, it is possible to better control the volume and rate of introduction of fluid into the supersonic jet produced in the shock chamber, thus allowing for better aerosolization and an increase in the duration of the aerosol burst.

Figure 22:
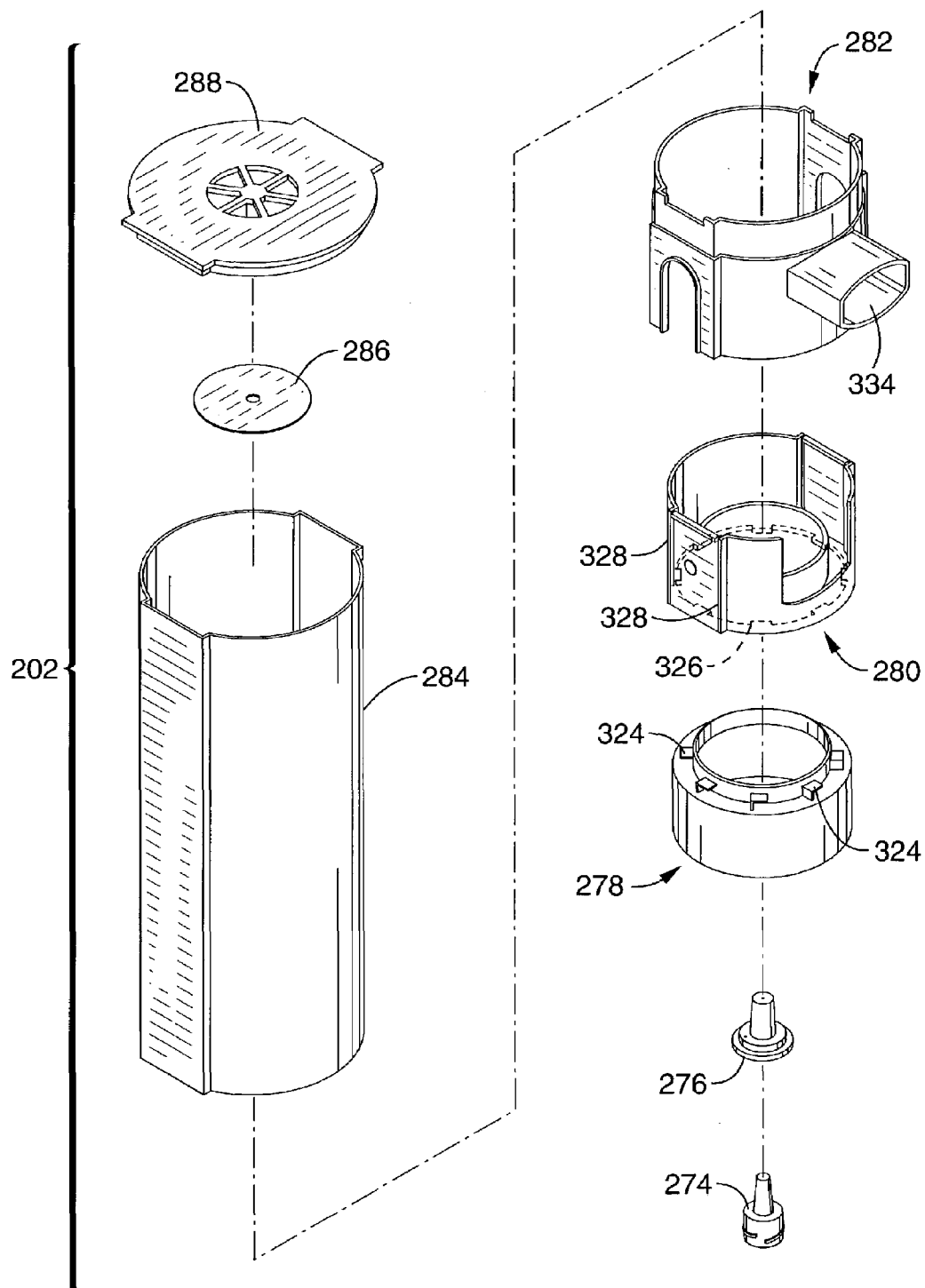
FIG. 22 is an exploded view of the aerosol generator of FIG. 21.
Figure 26:
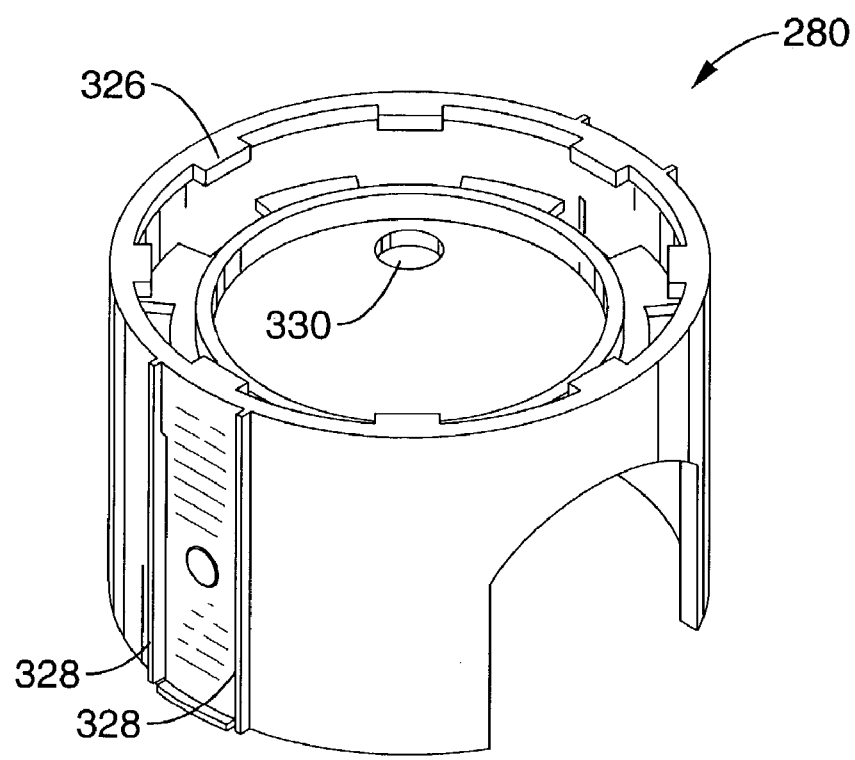
FIG. 26 is a perspective view of the cap employed in the inhaler of FIG. 13.

Reservoir cup 278 mates with cap 280 through the engagement of locking clips 324 on reservoir cup 278 shown in FIG. 22 with locking members 326 as shown in FIG. 26. Reservoir cup 278 and cap 280 are designed to allow the exit plane of secondary 276 to protrude through a bore 330 in cap 280 allowing for aerosol entry directly into aerosol chamber 340, while creating at the same time anti-spill ability for reservoir 332 as shown in FIG. 30. Anti-spill reservoir volume 332, shown in FIG. 30 is designed such that when invention is tipped sideways or upside down, liquid in reservoir does not spill out.

As seen in FIG. 26, cap 280 is preferably equipped with two pairs of protruding ribs 328 located on opposite sides of the cap which allow for column base 282 and spacer column 284 to slide over cap 280 without rotating.

Figure 27:
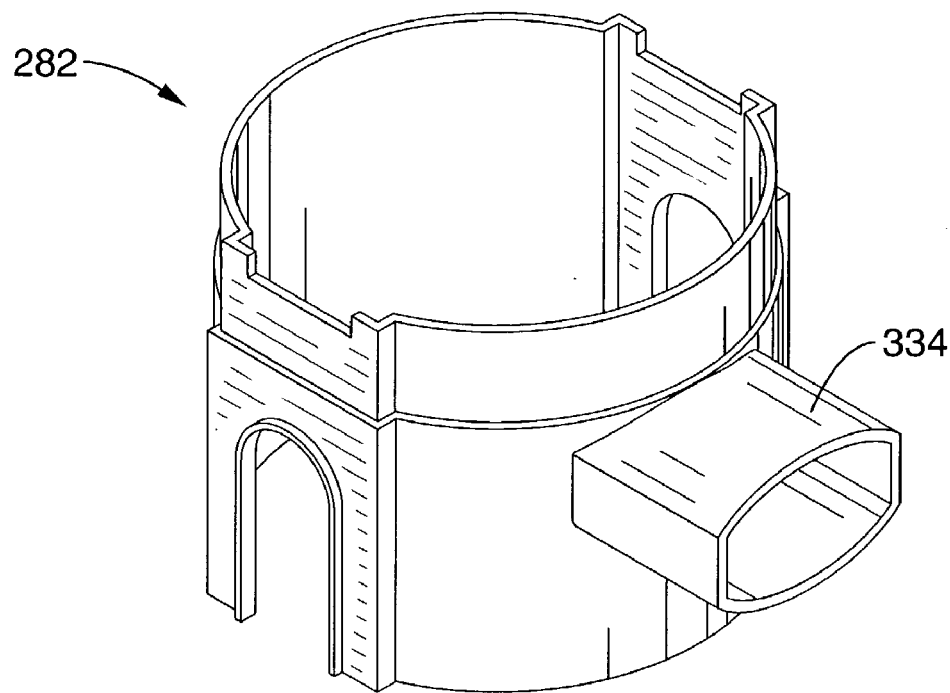
FIG. 27 is a perspective view of the column base employed in the inhaler of FIG. 13 and FIG. 22.

Column base 282, shown in FIG. 27, is equipped with mouthpiece 334 to allow for patient inhalation. Column 284 is preferably tubular and configured to fit onto column base 282. Optionally, column base 282, column 284, and column end 288 may be made of anti-static plastic material to prevent the loss of charged aerosol particles due to the attraction of the particles to oppositely charged aerosol chamber surfaces. Alternatively clear polycarbonate may also be used.

Figure 28:
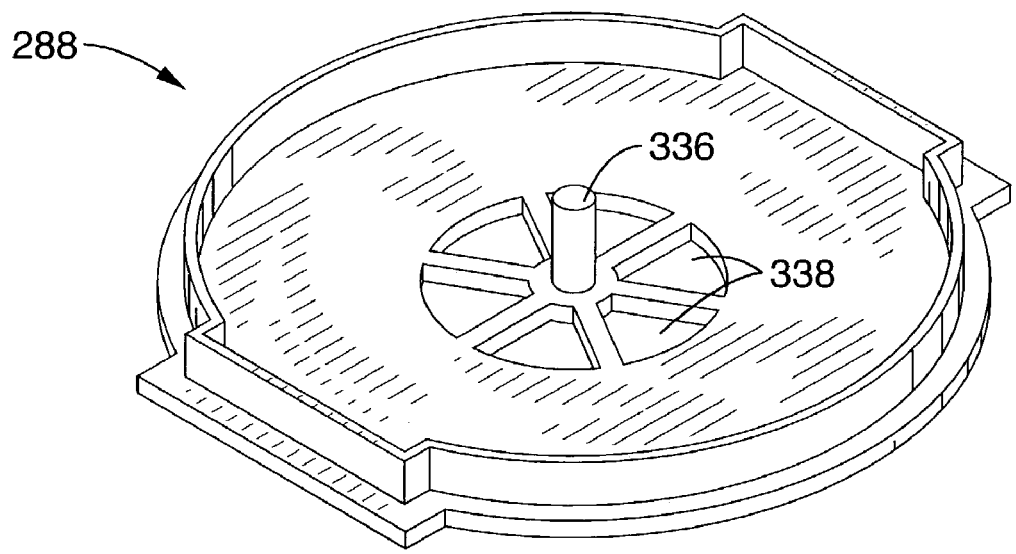
FIG. 28 is a perspective view of the end of the column of FIG. 22.

Referring now to FIG. 22 and FIG. 28, flapper valve 286 is preferably a thin planar rubber circular piece that has a center hole which fits over flapper valve post 336 of column end 288. Flapper valve 286 preferably has a large enough outer diameter to encircle inhalation ports 338. Column end 288 fits onto column 284 to form an aerosolization chamber 340.

Once aerosol is produced from the jet 274 and shock chamber 318, it enters into the aerosolization chamber 340 of column 284 where it is stored until patient inhales on mouthpiece 334. Flapper valve 286 prevents the patient from forcing stored aerosol out of chamber with an accidental exhalation. Upon inhalation, flapper valve 286 allows room air to be entrained into chamber 340.

Referring now to FIG. 29 and FIG. 30, the completed coupling of the aerosol generator 202, the actuator handle 200 and the gas canister assembly 204 can be seen. The apparatus can be conveniently stored in two pieces that are coupled prior to use. The full structure of the alternative embodiment of the apparatus of FIG. 13 can be seen in FIG. 29 and FIG. 30.

Figure 32:
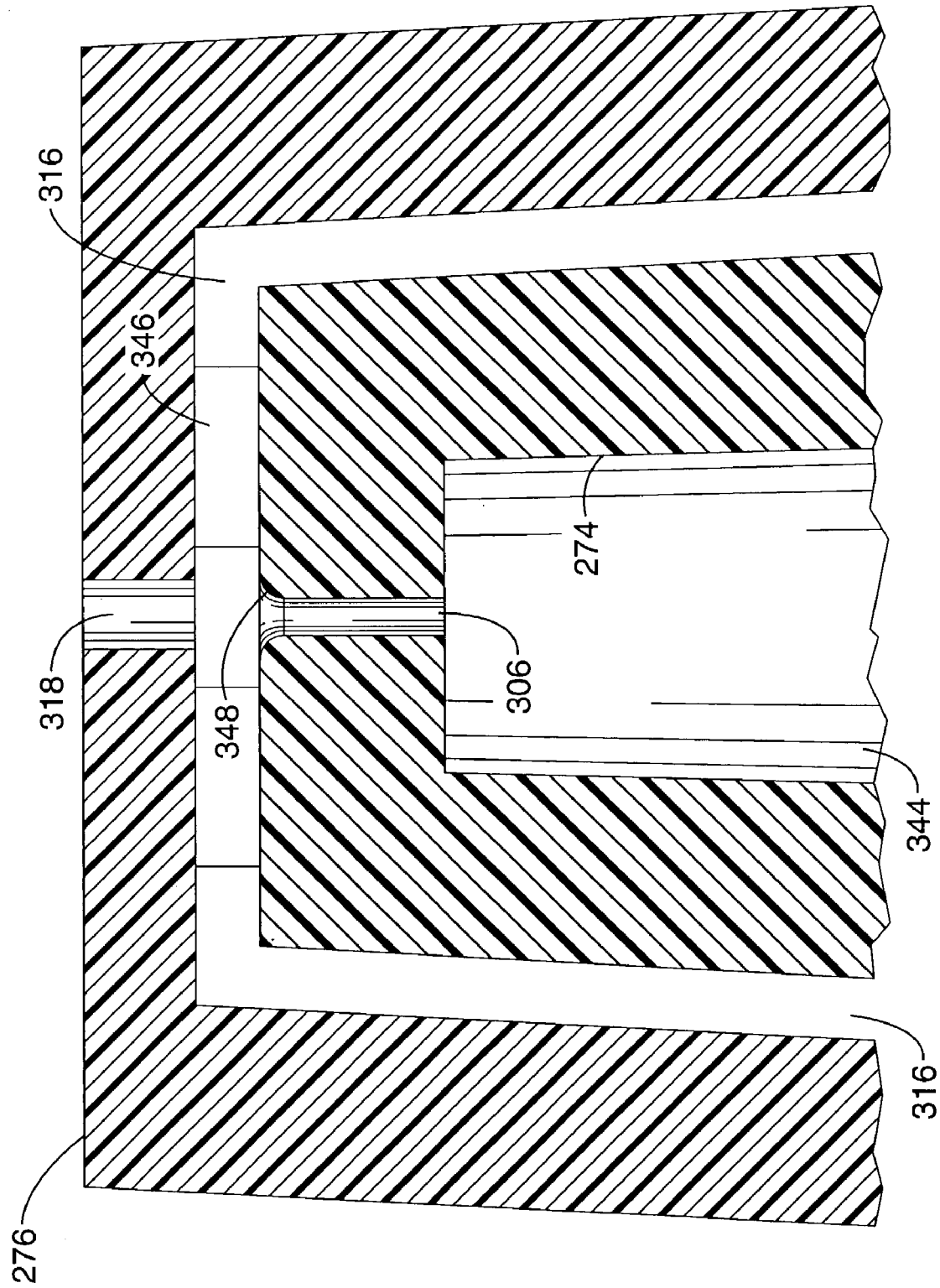
FIG. 32 is a detail side view in cross-section of the jet and shock chamber portion of the nozzle assembly of FIG. 31.

Referring also to FIG. 31 and FIG. 32, in use gas from canister 206 that has been previously seated on canister seal 238, enters the valve assembly 216 through pin orifice 270. Gas enters chamber 250 through valve stem inlet port 272 and valve stem inlet orifice 262 until the pressure of the gas in chamber 250 is equal to the pressure of the gas in canister 206. Upon actuation of trigger 220 as previously described, the contents of chamber 250 exits through valve stem outlet orifice 264 and valve stem outlet port 236 as a burst of gas. The burst of gas travels through the internal conduit 342 of the valve stem cover 218, and into the interior 344 of jet 274. Jet orifice 306 is dimensioned so that the jet formed in the jet orifice 306 will be supersonic producing the aerosolization process as described in the first embodiment. Additionally, jet orifice 306, and shock chamber 318 preferably have the same dimensions and performance characteristics as the first embodiment described herein.

Medicine held in reservoir 332 enters choke port 322 and channels 312 and is drawn to interstitial space 346 between the jet 274 and secondary 276 and aerosolized when brought in contact with the supersonic jet. The aerosolized medication is then contained in the interior chamber 340 of column 284 for inhalation by the patient.

Turning now to FIG. 33 and FIG. 34, an alternative embodiment of the invention is shown with reusable actuator handle assembly 350, gas cartridge assembly 352, an aerosol generator 354, and an aerosol holding chamber 356. In the embodiment shown, the aerosol generator 354 includes a shock wave amplification chamber 358 that extends into the aerosol holding chamber 356. An alternative embodiment of a shock wave amplification chamber is shown in FIG. 35. The aerosol generator 354 is preferably composed of an aerosol generator head member 360 that is configured to receive an interlocking cap 362. In use, liquid medicine is placed in reservoir 364 in head 360 and then head 360 and cap 284 are coupled together to form an enclosure. The chambers shown in FIG. 34 and FIG. 35 increase the volume of relatively small aerosol particles and generally separate and restrict larger aerosol particles from the aerosol storage column.

As shown in FIG. 33, the aerosol generator 354 connects to the actuator handle 350 by the engagement of threads 366 of the generator head 360. Upon actuation of the actuator, a small burst of $CO_2$ gas is caused to exit the actuator 350 and travel into the inlet 368 of the aerosol generator head 360. The compressed $CO_2$ gas continues to travel up from inlet 368 into jet orifice 370. Due to the pressure built up by the compressed $CO_2$ gas behind jet orifice 370, a sonic velocity jet is caused to be formed in the orifice and a supersonic expansion is caused to occur in shock chamber 372 and liquid from reservoir 364 is entrained by supersonic expansion jet into shock chamber 372 as described previously. The resulting aerosol jet exiting from shock chamber 372 is caused to pass down shock wave amplification chamber 358 in FIG. 34.

The shock wave amplification chamber 358 has a dual function that generally increases the output and efficiency of suitably sizes aerosol particles into aerosol holding chamber 356. One of the purposes of shock wave amplification chamber 358 is to capture the resulting spray and separate large particles emitted by the aerosol jet from the generator head 360 that are too large for effective inhalation. Typically, these large particles were not entrained into the shock waves and thus were never reduced down to a smaller particle size. This separation function is primarily realized by the impacts and coalescing of these large aerosol particles. Particles appropriately sized for inhalation (<10 microns) are able to aerodynamically maneuver so as to avoid collision with the walls of the shock wave amplification chamber 358. Particles of aerosol that are deposited on the walls of shock wave amplification chamber 358 preferably accumulate and drip back into the reservoir 364 to be aerosolized upon subsequent actuations.

A second function of the shock wave amplification chamber 358 is to reflect the acoustic energy generated by the supersonic expansion of the aerosol jet so as to generate more comparatively smaller aerosol particles from the larger particles contained within the aerosol jet. Testing has shown that significantly more aerosol particles that are suitably sized for respiration are generated with the shock wave amplification chamber 358 in place than generated without it, while the liquid entrained by the supersonic expansion of the jet remains the same. This means that both the output and efficiency (i.e. the amount of aerosol produced per the medication consumed) both increase. These improvements in output and efficiency are very beneficial, especially for delivery of expensive medications. The walls of the shock wave amplification chamber preferably are oriented at angles that reflect acoustic energy from the supersonic jet back on to the flow of aerosol particles that are emitted from the nozzle and reduce the size of the larger aerosol particles to smaller particles suitable for use.

In the embodiment shown in FIG. 33 and FIG. 34, the inner diameter of the shock wave amplification chamber 358 is approximately 0.375 inches and has a length of approximately 1.00 inch. Depending on the desired output and efficiency, these dimensions may be varied accordingly.

Turning now to FIG. 35, an additional embodiment of the shock wave amplification chamber is shown. As in the previous embodiment, the cap 374 is attached to the aerosol generator head 360. Carbon dioxide or other gas is caused to pass up inlet 368 and into jet orifice 370, and out shock chamber 372, causing entrainment of liquid from reservoir 364. The aerosol jet exiting shock chamber 372 is induced into forming additional small particles within the aerosol stream by the reflection of acoustic energy within the cavity formed by reservoir 364 and upper cap walls 376. The resulting aerosol exits from the aerosol outlet 378 and into the aerosol holding chamber. The embodiments of FIG. 34 and FIG. 35 work similarly, although the embodiment of FIG. 34 is more effective at reducing residual liquid left in the device that is unavailable for further aerosolization with subsequent uses.

Referring specifically to FIG. 33, an alternative trigger mechanism is shown that provides improved mechanical advantage and reduces the force necessary to actuate the apparatus. Upon squeezing of trigger 380, it is caused to rotate about pivot point 382, thus providing downward force on valve stem 384 and causing actuation of valve 386.

Figure 36:
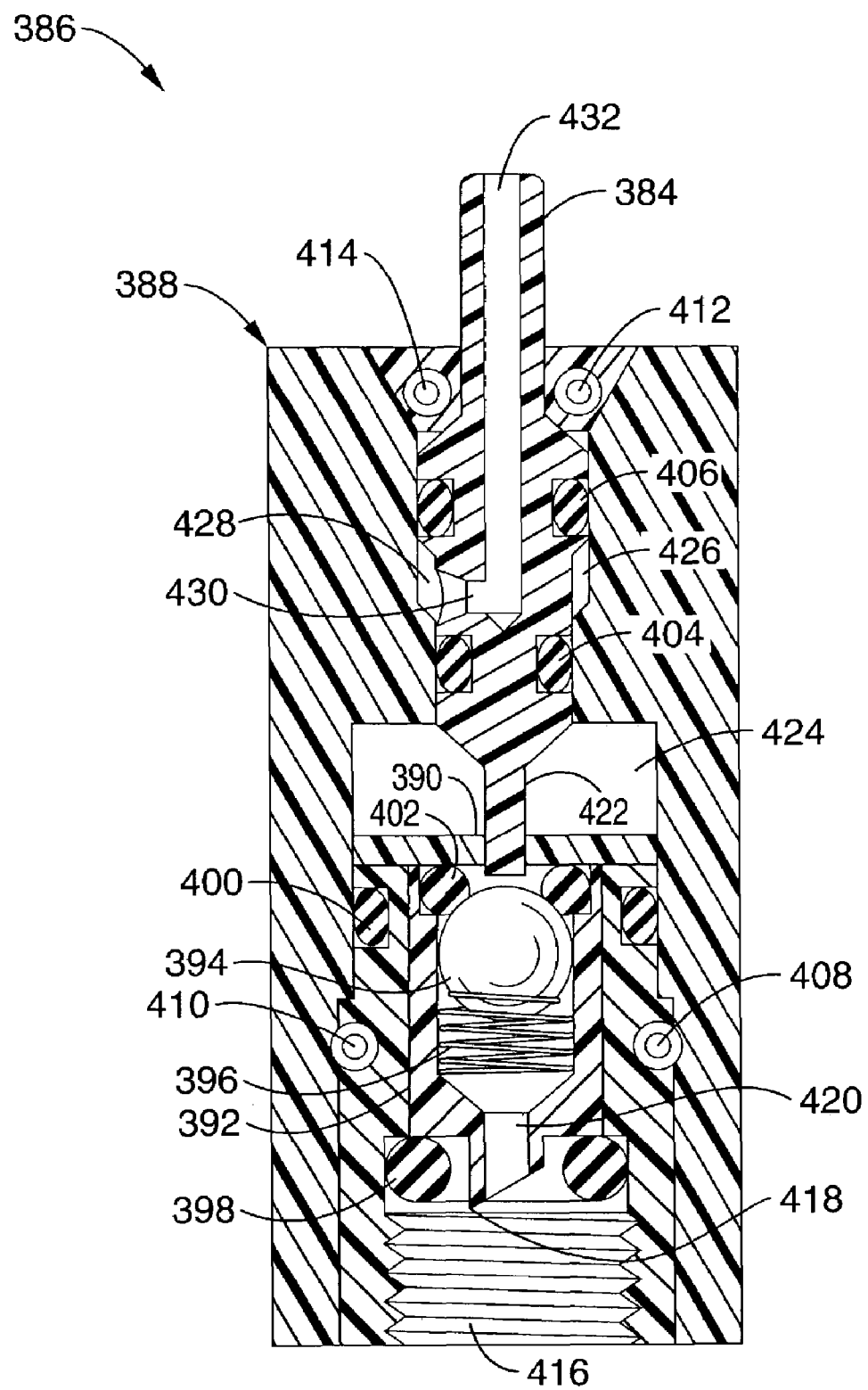
FIG. 36 is a cross sectional view of an alternative embodiment of the $CO_2$ burst valve according to the present invention.
Figure 37:
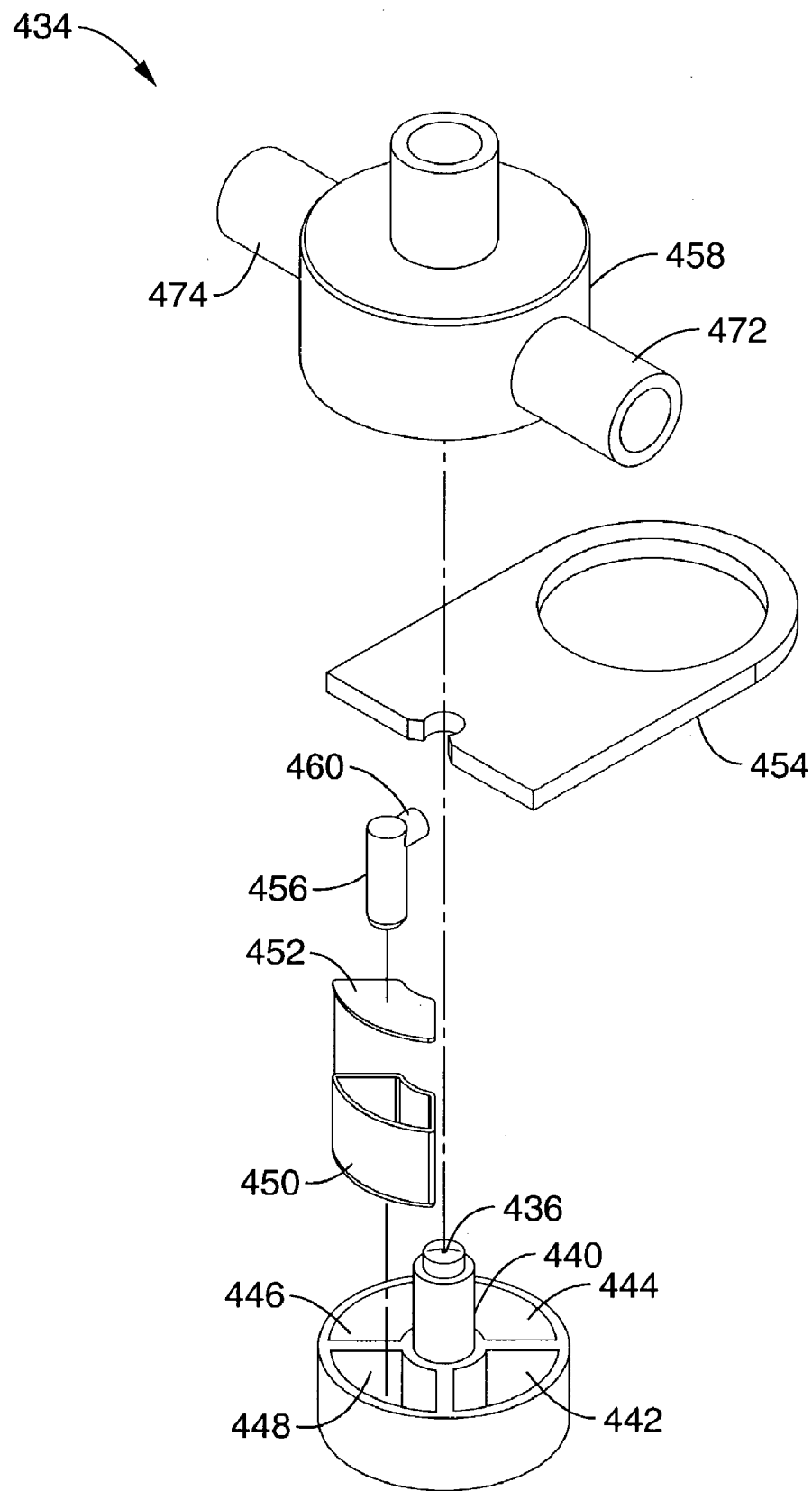
FIG. 37 is an exploded view of an embodiment of a blister pack aerosol generator according to the present invention.

Referring also to FIG. 36, one embodiment of valve 386 is shown in cross-section. The principle parts of valve 386 are the valve body 388, valve stem 384, valve insert 390, puncture pin 392, ball seal 394, and spring 396. Valve 386 also consists of O-rings 398, 400, 402, 404, and 406 as well as stop pins 408, 410, 412, and 414.

During assembly, the spring 396, ball seal 394, and o-ring 402 are placed in puncture pin 392, which are then placed into valve insert 390 and are held in place by an interference fit between puncture pin 392 and valve insert 390. O-ring 398 is placed into valve insert 390, and o-ring 400 is placed in an o-ring groove that runs circumferentially around valve insert 390. Valve insert 390 is then placed in valve body 388 and held in place by cylindrical stop pins 408 and 410. Stop pins 408 and 410 mate with valve body 388 and valve insert 390 by two through holes that pass through valve body 388 and two external grooves in valve insert 390. O-rings 404 and 406 are then placed in o-ring grooves running circumferentially around valve stem 384. Valve stem 384 is then placed in valve body 388 as shown and prevented from escaping by placement of cylindrical stop pins 412 and 414, which fit into holes passing through valve body 388.

Carbon dioxide or other gas canisters are engaged with valve 386 by threads 416, which ultimately causes the end of the gas canister to be sealed against o-ring 398 and punctured by piercing point 418 of puncture pin 392 as the canister is advanced along the threads 416. Upon puncture of the gas canister, compressed $CO_2$ gas is can travel through puncture pin gas passage 420, providing pressure against ball seal 394 in conjunction with the force of spring 396 causing a seal between ball seal 394 and o-ring 402. This configuration represents the resting state of valve 386.

Upon actuation of valve 386, valve stem 384 is caused to be pushed into valve 386 such that valve stem nose 422 is pushed against ball seal 394 resulting in the escape of gas around the ball seal 394 into holding volume 424. Gas moving into holding volume 424 is prevented from escaping by o-ring 404 while the valve stem is in the actuated position allowing for the pressure of gas in holding volume 424 to reach the same pressure as in the gas canister.

Upon release of the actuation force on valve stem 384, the pressure of the compressed $CO_2$ gas causes valve stem 384 to disengage with ball seal 394, thus resealing the gas canister. Upon further disengagement of valve stem 384, continued to be caused by compressed $CO_2$ gas in holding volume 424, o-ring 404 is caused to pass over longitudinal gas escape grooves 426 and 428, releasing compressed gas held in holding chamber 424 through valve stem gas inlet 430 and out valve stem gas outlet 432 for delivery to the gas inlet of the aerosol generator as previously described and shown in FIG. 33.

Turning now to FIG. 37 through FIG. 41, one embodiment of a blister pack aerosol generator 434 according to the invention is shown. The jet orifice 436 is integral to the blister base 438 in this embodiment. Positioned radially around jet orifice stem 440 are blister holding cavities 442, 444, 446, and 448. In the embodiment shown, there are four blister pack holding cavities. However, it will be understood that the number of blister pack cavities may be varied as desired.

It is preferred that the blister pack 450 be made of a low density polyethylene, or some other material that is stable with long term contact with the medication, and sealed by a foil cover 452 which is also preferably coated with polyethylene or similar inert plastic material. During assembly of one embodiment of the blister pack aerosol generator 434, medication is placed in blister 450 and sealed by foil cover 452, preferably by heat stamping. The sealed blister pack 450 containing the medication is then placed in a blister cavity. Blister pack 450 is preferably sized to be as high as the walls of the blister cavity 442 so that tops of each are congruent when assembled. After sealed blister 450 has been placed in blister holding cavity 442, for example, safety strip 454 is inserted over jet orifice stem 440 to protect the foil covers 452 of the blister packs from damage and to restrict use of the device.

Figure 38:
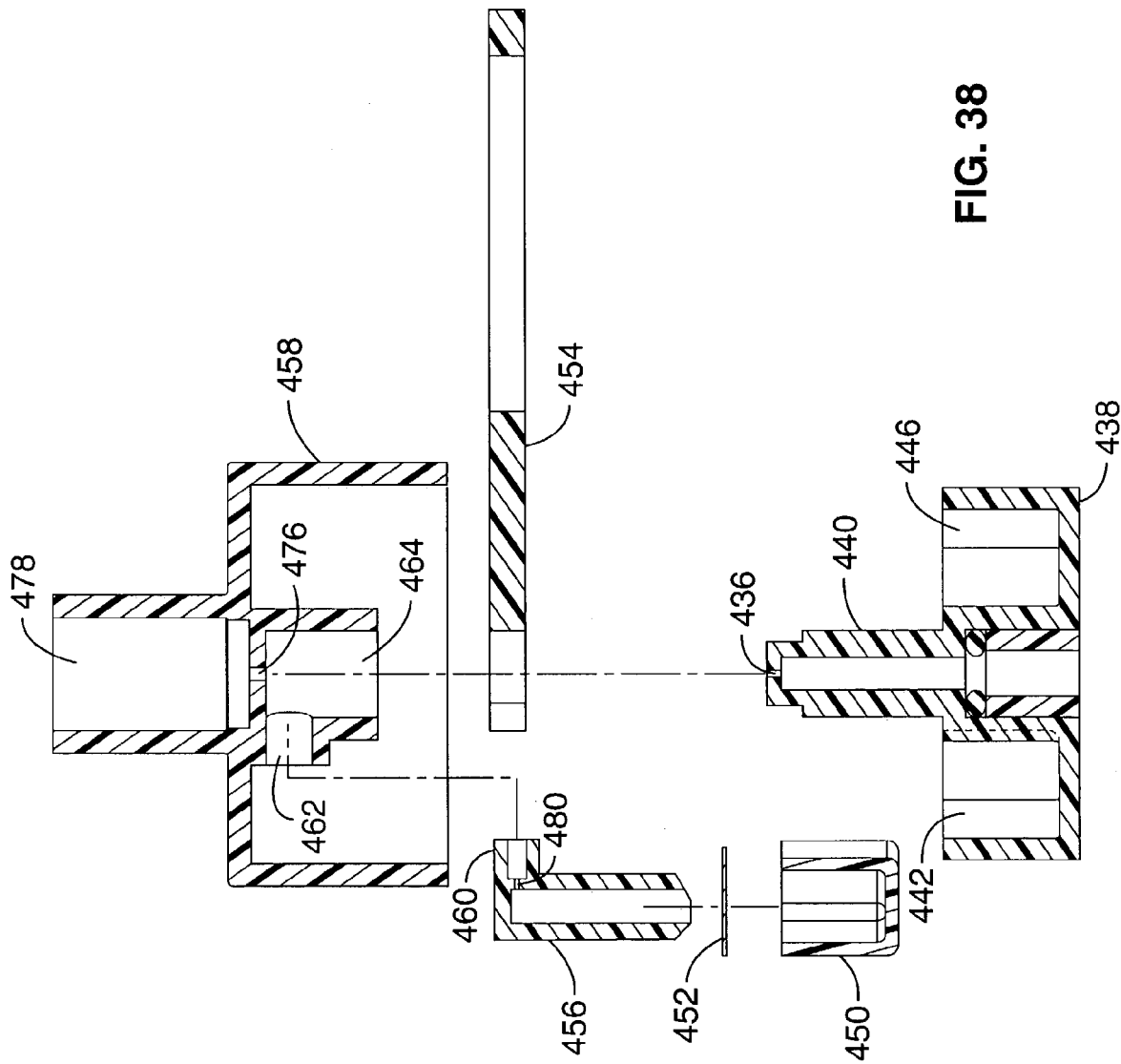
FIG. 38 is an exploded cross-sectional view of a blister pack aerosol generator shown in FIG. 37.
Figure 39A:
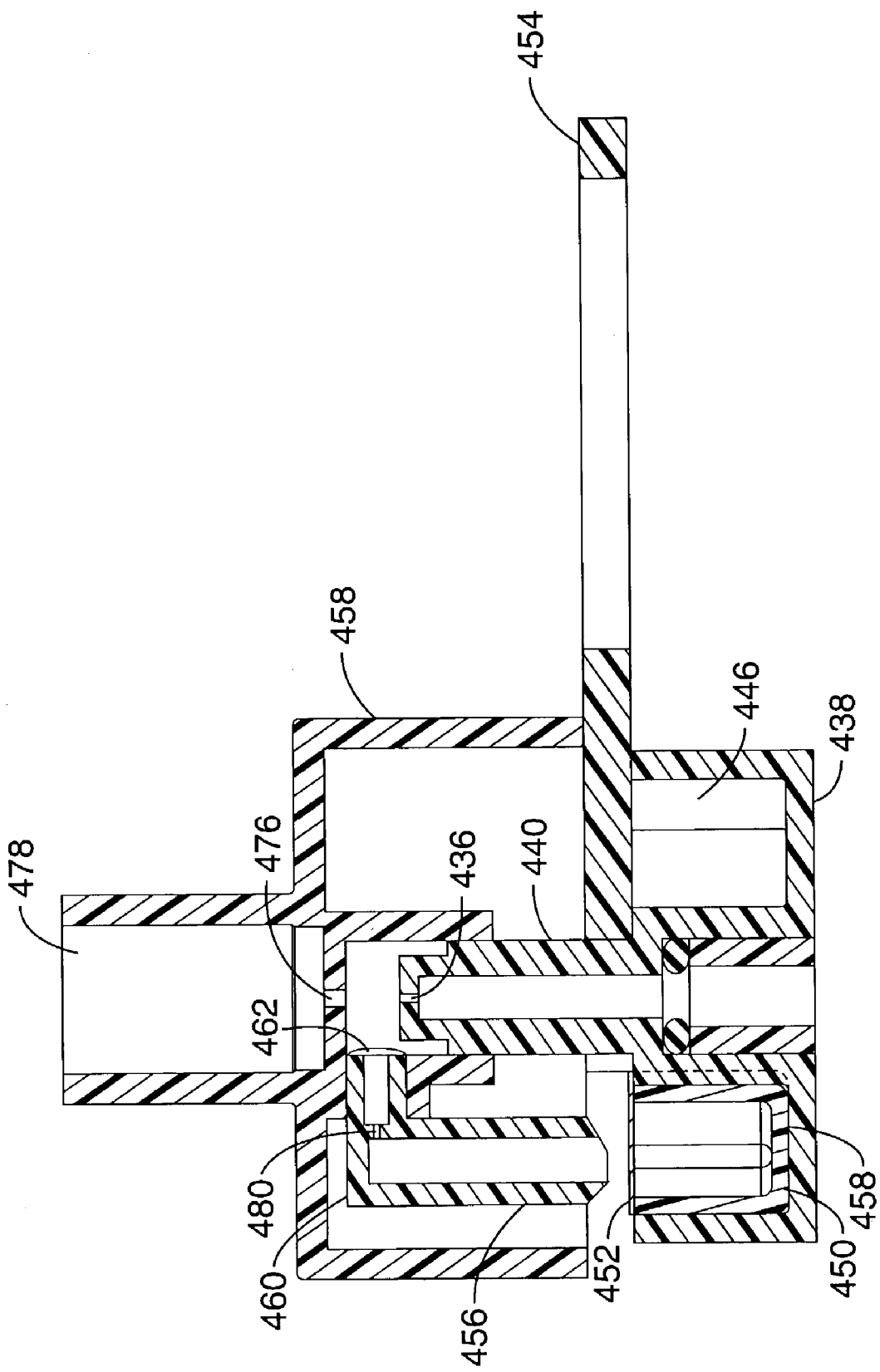
FIG. 39A is a cross-sectional view of a blister pack aerosol generator of FIG. 38 with the safety strip in place.
Figure 39B:
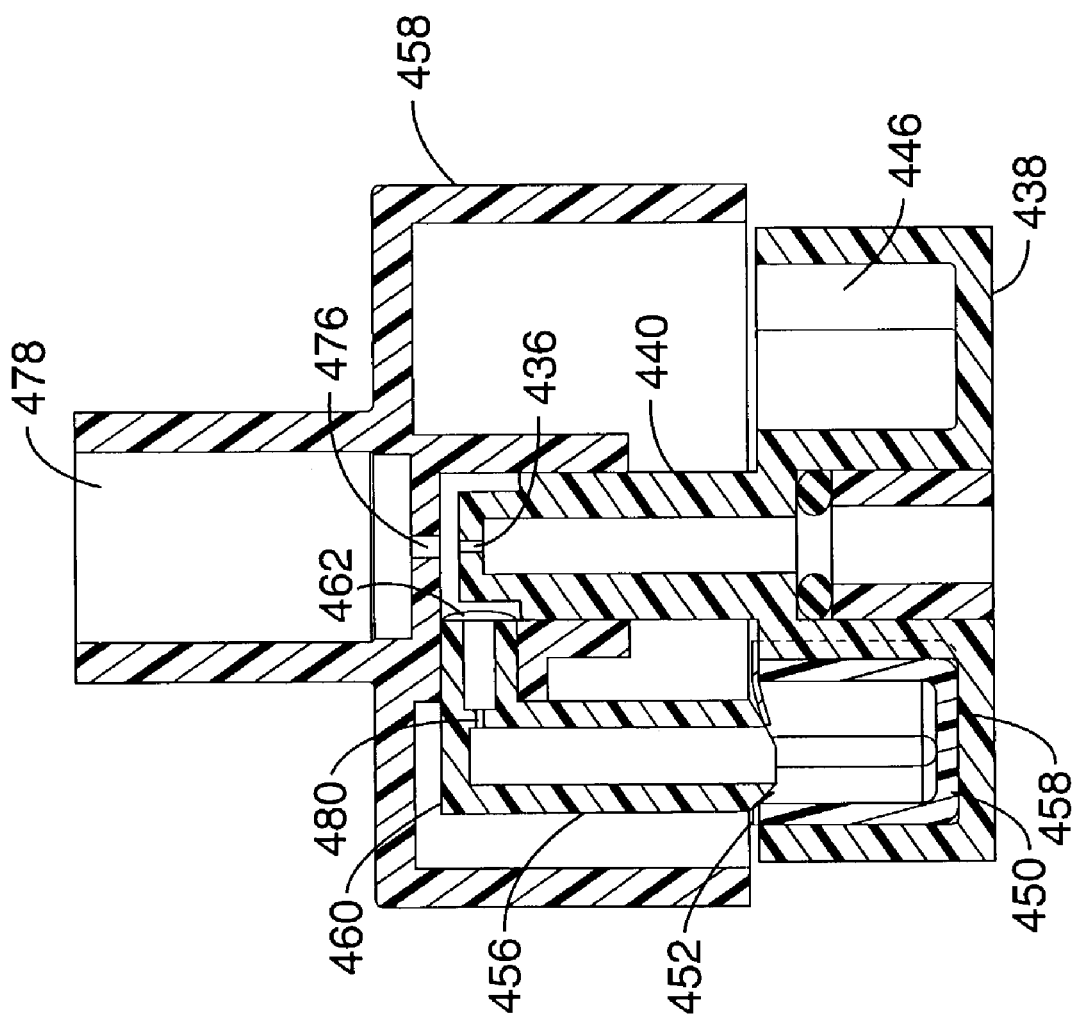
FIG. 39B is a cross-sectional view of a blister pack aerosol generator of FIG. 38 with the safety strip removed and the blister pack punctured.
Figure 40:
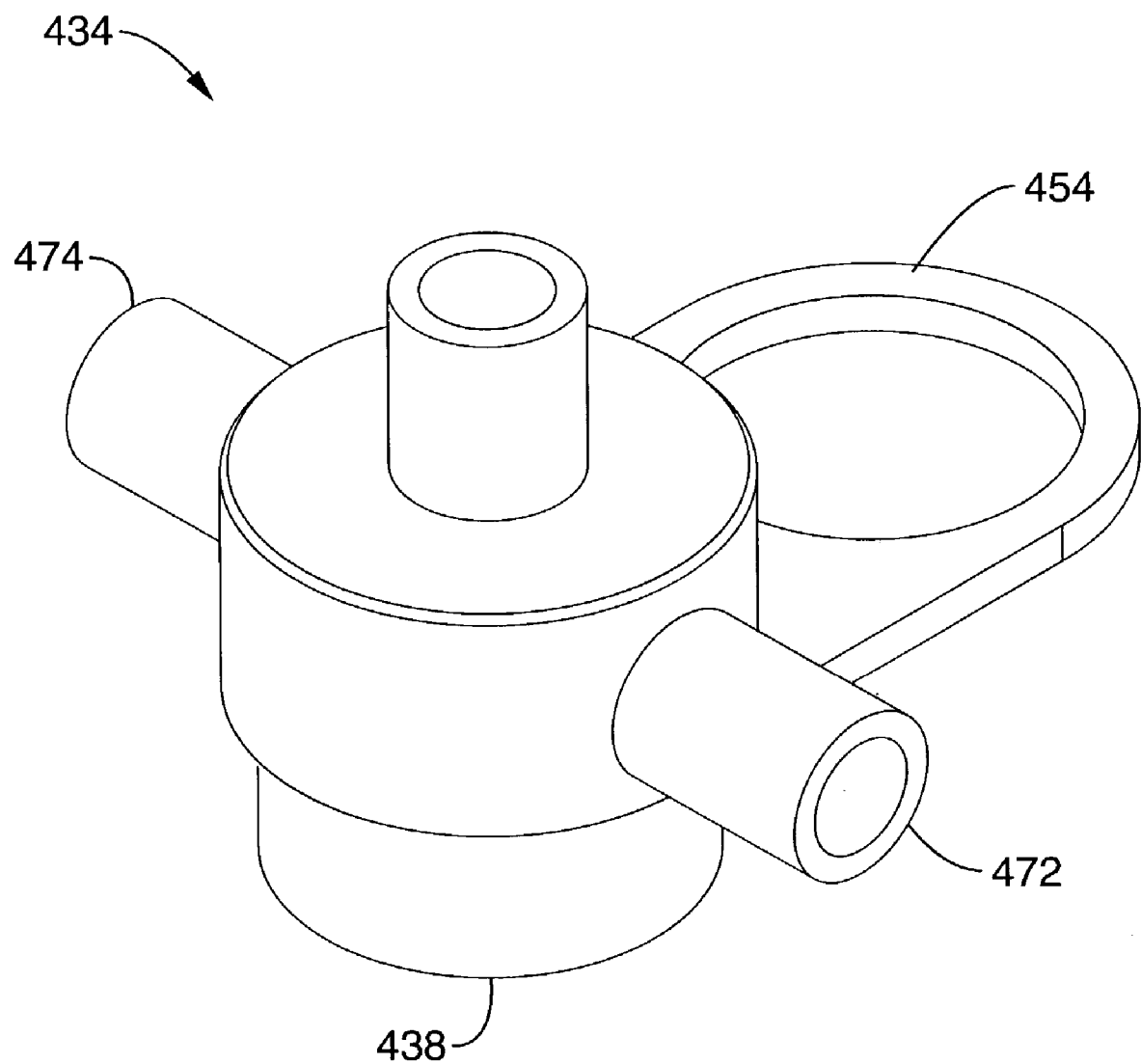
FIG. 40 is a perspective view of a blister pack aerosol generator of FIG. 37.

Feed rod 456 is then placed in cap 458. As most readily shown in FIG. 38, FIG. 39A and FIG. 39B, feed rod 456 is equipped with a cylindrical member with feed rod outlet 460 that fits into cap liquid inlet 462 located in cap 458. Once feed rod 456 is placed in cap 458, cap 458 is placed onto blister base 438 by engagement of jet orifice stem 440 and jet receptacle 464 as shown in FIG. 38. The fit between jet orifice stem 440 and jet receptacle 464 is preferably sufficient to prevent accidental disengagement of the two parts. Safety strip 454 prevents cap 458 from traveling to far down jet orifice stem 440 and feed rod 456 from puncturing blister until ready for use. FIG. 39A shows the aerosol generator with the safety strip 454 in position and FIG. 39B shows the safety strip 454 removed and the blister base 438 and cap 458 in the proper position for use.

Figure 41:
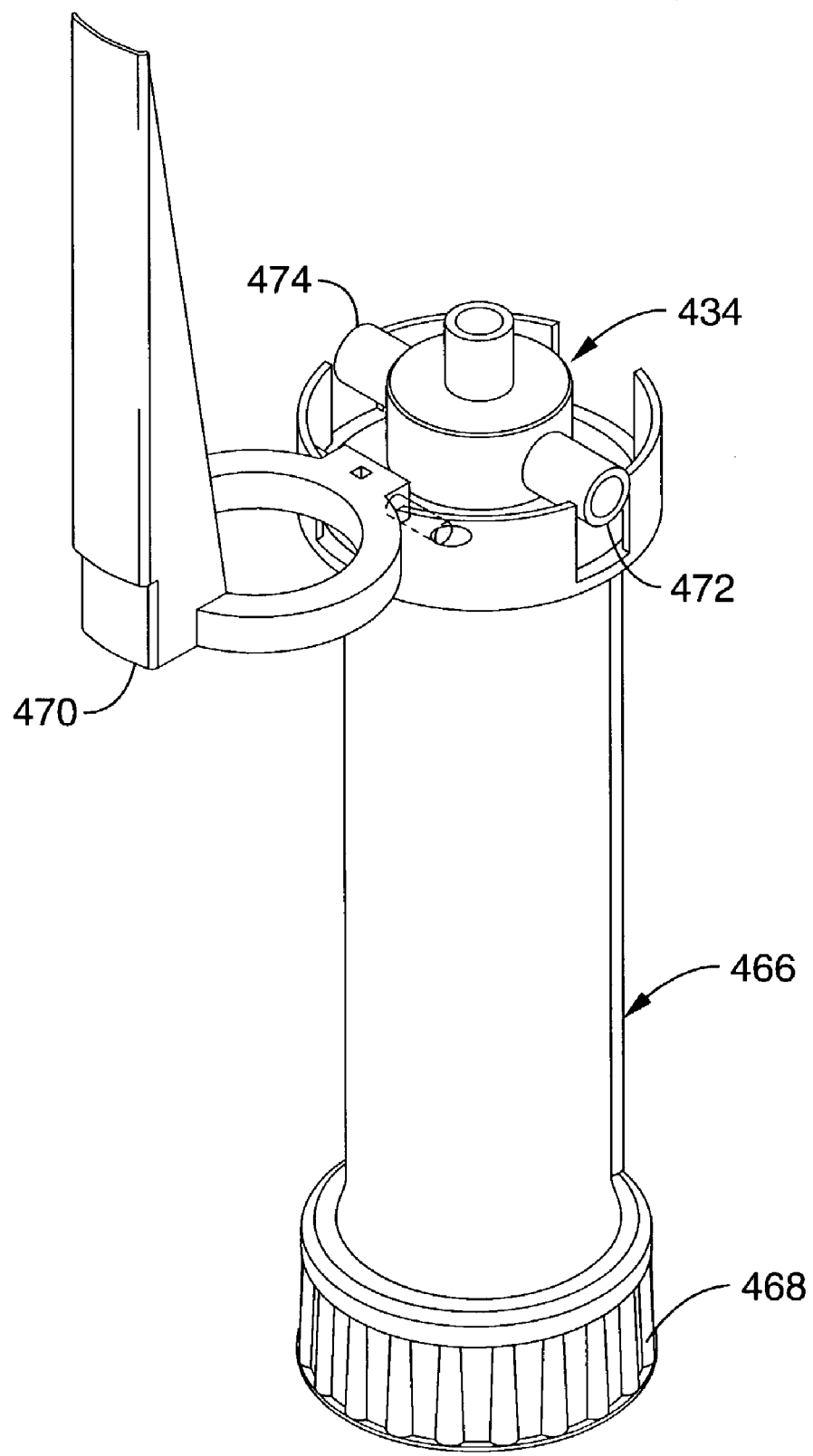
FIG. 41 is a perspective view of an actuator containing a blister pack aerosol generator with the trigger in the open position.

Referring to FIG. 41, when a patient is ready for a treatment the blister pack aerosol generator 434 is fitted to the top of actuator 466, which as with the previous embodiment, is outfitted with a disposable gas cartridge 468, a trigger 470, and a aerosol holding chamber (not shown) which fits around the top of the actuator providing sufficient volume for holding aerosol. Unlike the actuator of the other embodiments, the actuator 466 of the blister design preferably has a trigger 470 that rotates up, allowing for the placement of the blister pack aerosol generator 434 to be placed on top of the actuator. After placement of aerosol generator 434, safety strip 454 is removed from aerosol generator 434 by pulling out and away from the generator. Trigger 470 is then rotated back down approximately 180 degrees, and the aerosol holding chamber (not shown) is placed on the actuator as seen in FIG. 41.

With safety strip 454 removed, the squeezing of the trigger 470 will force cap 458 downward by the engagement of trigger bosses 472 and 474 with trigger 470. The downward movement of cap 458 causes feed rod 456 to puncture foil cover 452 of the blister pack 450 and come in contact with the medication stored within blister 450. The apparatus is now ready for aerosolization of the medication in the blister 450 through one or more bursts of gas.

In one embodiment using the valve shown in FIG. 36, compressed $CO_2$ gas is not released through the jet orifice 436 until trigger 470 has been released. With the release of trigger 470, carbon dioxide is caused to pass through jet orifice 436 and into shock chamber 476 and through shock wave amplification chamber 478. Jet orifice 436, shock chamber 476, and shock wave amplification chamber 478 function as in previously described embodiments. The vacuum generated by the supersonic jet emitting from jet orifice 436 causes liquid to be entrained from blister 450, through feed rod 456, through liquid choke orifice 480 and into the shock chamber 476 for aerosol production. The liquid choke orifice 480 functions as described in previous embodiments to control aerosol production and increase efficiency by limiting the volume or rate of liquid exposed to the supersonic jet over time. Once aerosol has been produced and deposited in aerosol holding chamber (not shown), the patient simply inhales on the mouthpiece and draws the aerosolized medication into the lungs.

Preferably, the aerosol chamber is made transparent so as to provide the patient with visual feedback on the production of aerosol and the subsequent inhalation of the aerosol. Blister pack aerosol generators 434 are intended for one treatment, which may consist of one or many bursts and inhalations. After the treatment, blister pack aerosol generator 434 may be disposed of in a refuse receptacle. The current embodiment has the advantage of being able to have multiple blisters packaged within a blister aerosol generator 434 for delivery of combinations of medication with each inhalation. This is particularly useful for components of medication that are not able to be stored together for long periods of time.

Likewise, the shock wave aerosolization process can be efficiently used with micronized powder in blister packs. Blister packs, containing one or more cells, may be used to store a pre-determined amount of powder. Prior to aerosolization, a feed tube, which is in fluid communication with the shock wave aerosolization nozzle assembly, is inserted into the blister pack cell. Subsequent to the insertion of the feed tube in the blister pack, the gas valve is actuated, creating a set burst of gas. As previously described, the carbon dioxide exits the throat of the jet, causing a vacuum, which entrains the micronized powder through the feed tube and into the shock chamber. As with liquid medication, when medicinal powder is entrained it becomes efficiently aerosolized with the reflected shock waves and carried out to the mouthpiece or valve chamber for inhalation by the user.

Figure 42:
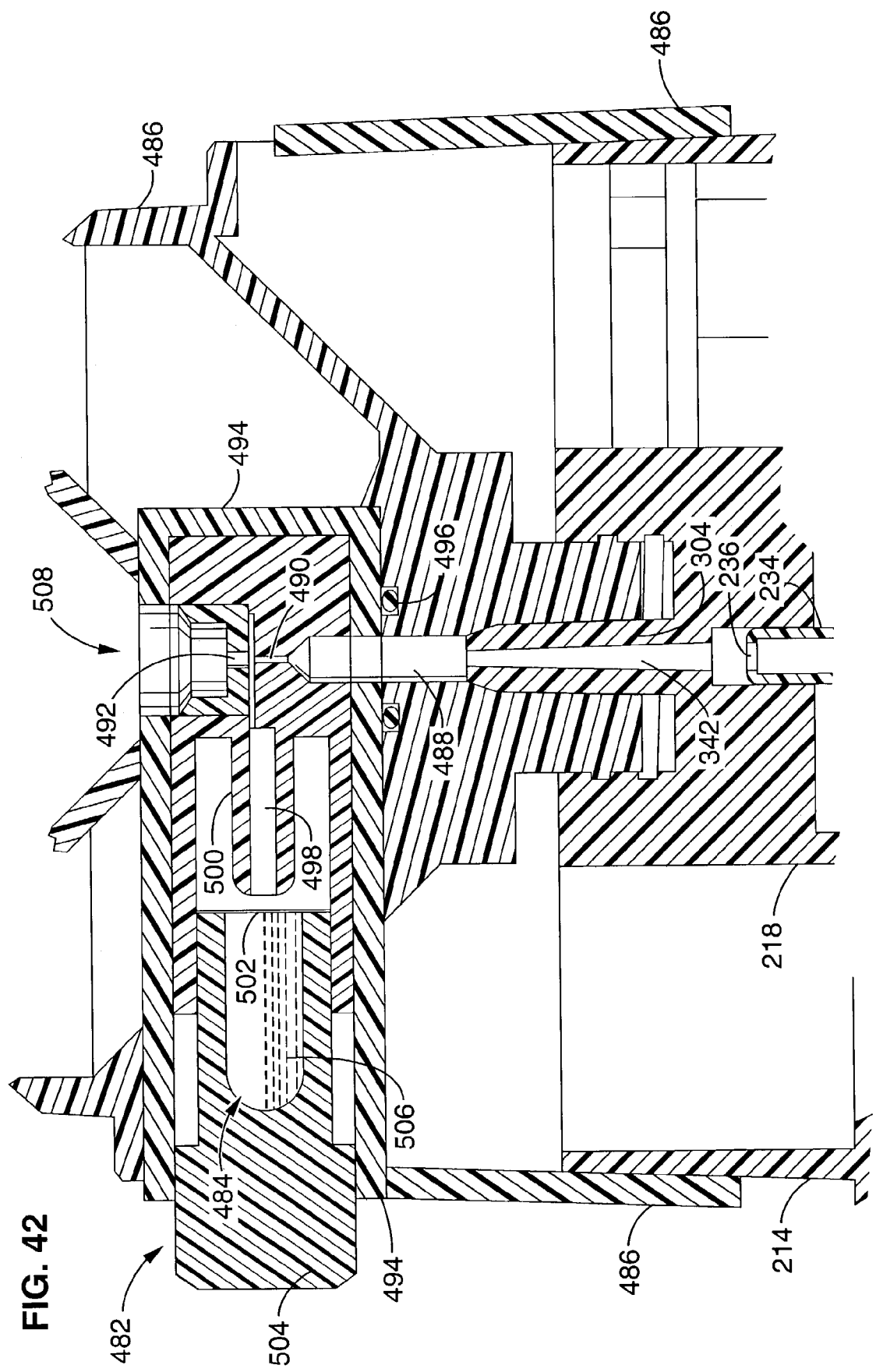
FIG. 42 is a side view in cross-section of an alternative embodiment of an inhaler according to the present invention employing a disposable cartridge containing both the nozzle and a blister pack of medication.

In accordance with an alternative embodiment of the invention, a single blister pack cartridge is shown in FIG. 42. The aerosol generating assembly including the jet and supersonic shock chamber is provided in a small cartridge 482 along with a single blister pack 484 containing sufficient medication for one aerosol treatment. In this single use embodiment, the cartridge 482 is to be inserted into the base of the aerosol generator housing 486, which is coupled to the body 214 of actuator handle 200 so as to cause the duct 488, jet 490 and supersonic shock nozzle 492 to become oriented above the channel 342 of valve cover port 304. Cartridge 482 has an exterior housing that is configured to be disposed in a slot 494 within the base 486 by the patient or care provider. After insertion into the base, cartridge 482 is sealed to the outlet passage of carbon dioxide with o-ring 496.

The shock nozzle assembly portion of cartridge 482 has a jet orifice 490 as well as a shock chamber 492 that are preferably configured and function as described in the previous embodiments. Adjacent to jet orifice 490 is liquid feed line 498 that is in fluid communication with prong 500.

Once cartridge 482 is inserted, aligned and seated in base 486, the apparatus is ready for use. The foil barrier 502 of blister pack 484 is preferably punctured by the prong 500 by the user pressing the back wall 504 of cartridge 482 and sliding the foil barrier 502 of blister pack 484 on to the prong 500. It can be seen that the medicine 506 within blister pack 484 is now capable of being entrained from the blister pack 484 through liquid feed tube 498 and through to the supersonic shock nozzle assembly.

Accordingly, when the trigger is depressed, gas is released through the bore 236 of the valve and out port 304 through channel 342 into duct 488. The gas then passes through jet 490 and shock chamber 492. As gas is caused to pass through the jet orifice 490 and shock chamber 492, the medicine 506 in the blister pack 484 is entrained and aerosolized by the supersonic shock nozzle as described with previous embodiments. Aerosol is directed to chamber 508 from the supersonic shock nozzle for inhalation by the patient.

Upon completion of the aerosol treatment, the supersonic shock nozzle/blister cartridge 482 may be removed and discarded by the user. This single use embodiment may work with or without an aerosol storage chamber and has the advantage of reducing possible contamination of the supersonic shock nozzle between treatments.

It can be seen, therefore, that the present invention provides an inhaler device that can deliver a burst of aerosol from an aqueous solution. In this way a number of advantages are realized which include, less expense on the part of the patient, less cost in formulation development, better aftertaste, portability, and convenience.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for producing shock wave aerosolization, comprising:

a nozzle;

means associated with said nozzle for generating a supersonic jet of gas from a source of compressed gas;

means for introducing a volume of liquid within said supersonic jet of gas;

means for regulating the introduction of said volume of liquid within said supersonic jet of gas, wherein a quantity of aerosol is and produced; and an aerosol separator for separating large aerosol particles from small aerosol particles, said aerosol separator comprising a separator body with a central chamber and an aerosol outlet.

2. An apparatus as recited in claim 1, further comprising a sonic shock chamber configured for receiving said supersonic jet of gas.

3. An apparatus as recited in claim 2, further comprising:
a user actuated valve; and
means for releasing a volume of compressed gas in bursts by said valve and delivering said supersonic jet of gas to said shock chamber.

4. An apparatus as recited in claim 3, further comprising:
means for delivering a burst of compressed gas to said nozzle and forming said supersonic jet prior to a material being entrained and mixed with said jet.

5. An apparatus as recited in claim 1, further comprising:
means for regulating a rate of introduction of said volume of liquid that is entrained with said supersonic jet of gas.

6. An apparatus as recited in claim 5, wherein said means for regulating the rate of introduction of a liquid into said supersonic jet comprises a liquid feed choke.

7. An apparatus as recited in claim 1, wherein said means for regulating the volume of a liquid introduced into said supersonic jet comprises a lumen associated with said nozzle configured to entrain a desired volume within a burst of gas.

8. An apparatus for producing shock wave aerosolization, comprising:
a nozzle;
a user actuated valve associated with said nozzle adapted to generate a supersonic jet of gas;
a material feed associated with said nozzle configured to introduce a volume of material within said supersonic jet of gas, wherein a quantity of aerosol is produced;
a material feed choke; and
an aerosol separator for separating large aerosol particles from small aerosol particles, said aerosol separator comprising a separator body with a central chamber and an aerosol outlet.

9. An apparatus as recited in claim 8, further comprising a sonic shock chamber configured for receiving said supersonic jet of gas.

10. An apparatus as recited in claim 8, further comprising:
means for releasing a volume of compressed gas in discrete bursts by said user actuated valve.

11. An apparatus as recited in claim 10, further comprising:
means for delivering a burst of compressed gas to said nozzle and forming said supersonic jet prior to a material being entrained and mixed with said jet.

12. An apparatus as recited in claim 8, wherein said aerosol separator further comprises:
a tubular body continuous with said aerosol outlet and said central chamber of said separator body.

13. An apparatus as recited in claim 8, wherein said aerosol separator further comprises:
means for reflecting acoustic energy from said supersonic jet within said central chamber of said separator body.

14. An apparatus for producing shock wave aerosolization, comprising:
a source of compressed gas;
a supersonic shock nozzle;
a user actuated valve configured to release said compressed gas in bursts for delivery through said supersonic shock nozzle;
an aerosol separator, wherein for separating large aerosol particles can be separated from small aerosol particles;
wherein said supersonic shock nozzle comprises:
a jet orifice configured to receive compressed gas from said source of compressed gas; and
a sonic shock chamber configured to receive compressed gas discharged from said jet orifice;
wherein said jet orifice is configured to produce a supersonic jet from said compressed gas; and
wherein said shock chamber is configured to receive said supersonic jet and produce shock waves.

15. An apparatus as recited in claim 14, wherein said supersonic jet is configured to establish a series of reflected compression and expansion shock waves in said shock chamber when said supersonic jet is over expanded or under expanded.

16. An apparatus as recited in claim 15, wherein said supersonic jet will be approximately the diameter of the jet orifice and travel down the axis of the shock chamber.

17. An apparatus as recited in claim 15, wherein a cylindrical shock wave will be generated in said shock chamber that envelopes the entire jet when said supersonic jet is perfectly expanded.

18. An apparatus as recited in claim 15, wherein upon formation of said supersonic jet and resulting shock waves in said shock chamber, a vacuum is generated which causes a liquid from a liquid reservoir to be entrained through a liquid feed into said shock chamber.

19. An apparatus as recited in claim 18, wherein upon entrainment of liquid into the shock chamber, the initial liquid entrained comes in contact with shock waves, producing aerosol particles suitable for inhalation.

20. An apparatus for producing shock wave aerosolization, comprising:
a source of compressed gas;
a supersonic shock nozzle;
a user actuated valve configured to release said compressed gas in bursts for delivery through said supersonic shock nozzle; and
an aerosol separator, wherein large aerosol particles can be separated from small aerosol particles;
wherein said aerosol separator comprises a separator body with a central chamber and an aerosol outlet.

21. An apparatus as recited in claim 20, wherein said aerosol separator further comprises:
a tubular body continuous with said aerosol outlet and said central chamber of said separator body.

22. An apparatus for producing shock wave aerosolization, comprising:
a source of compressed gas;
a supersonic shock nozzle;
a user actuated valve configured to release said compressed gas in bursts for delivery through said supersonic shock nozzle; and
an aerosol separator, wherein large aerosol particles can be separated from small aerosol particles;
wherein said aerosol separator further comprises:
means for reflecting acoustic energy from said supersonic jet within said central chamber of said separator body.

23. An apparatus as recited in claim 22, wherein said means for reflecting acoustic energy comprises angular walls, wherein larger aerosol particles can be divided into smaller aerosol particles.

24. An apparatus for producing aerosol, comprising:
a source of compressed gas;
means for generating a supersonic jet of gas from said source of compressed gas;
means for introducing material into said supersonic jet of gas to produce aerosol particles; and
an aerosol separator for separating large aerosol particles from small aerosol particles, said aerosol separator comprising a separator body with a central chamber and an aerosol outlet.

25. An apparatus as recited in claim 24, wherein said means for generating said supersonic jet of gas comprises a nozzle.

26. An apparatus as recited in claim 25, wherein said means for introducing particulates into said supersonic jet of gas comprises:
a material reservoir; and
ducts associated with said nozzle, said ducts communicating with said reservoir, wherein said material is introduced into said jet of gas.

27. An apparatus as recited in claim 24, further comprising:
means for regulating the introduction of material into said jet of gas.

28. An apparatus as recited in claim 27, wherein said means for regulating the introduction of material into said jet of gas comprises an orifice.

29. An apparatus as recited in claim 27, wherein said means for regulating the introduction of material into said jet of gas comprises a liquid choke.

30. An apparatus as recited in claim 24, further comprising:
means for regulating the total volume of material introduced into said jet of gas.

31. An apparatus as recited in claim 24, wherein said material introduced into said supersonic jet of gas comprises a liquid.

32. An apparatus as recited in claim 24, further comprising:
means for delivering a discrete volume of compressed gas to said nozzle.

33. An apparatus as recited in claim 32, wherein said means for delivering a discrete volume of compressed gas to said nozzle comprises a metered valve.

34. An apparatus as recited in claim 24, further comprising a sonic shock chamber configured for receiving said supersonic jet of gas.

35. An apparatus for producing aerosol, comprising:
a source of pressurized gas;
a supersonic shock nozzle;
a reservoir of liquid in fluid communication with said nozzle;
a metered valve configured to release said pressurized gas in bursts for delivery through said supersonic shock nozzle; and
an aerosol separator coupled to said shock nozzle, wherein large aerosol particles are separated from small aerosol particles;
wherein said aerosol separator comprises a separator body with a central chamber and an aerosol outlet.

36. An apparatus as recited in claim 35, wherein said supersonic shock nozzle comprises:
a jet orifice configured to receive compressed gas from said source of pressurized gas;
a lumen in fluid communication with said reservoir of liquid; and
a sonic shock chamber configured to receive entrained liquid mixed with a jet of compressed gas discharged from said jet orifice.

37. An apparatus as recited in claim 36:
wherein said jet orifice is configured to produce a supersonic jet from said compressed gas; and
wherein said shock chamber is configured to receive said supersonic jet and produce shock waves.

38. An apparatus as recited in claim 37, further comprising:
means for regulating the introduction of liquid into said supersonic jet of gas.

39. An apparatus as recited in claim 37, wherein said means for regulating the introduction of liquid into said jet of gas comprises an orifice.

40. An apparatus as recited in claim 35, wherein said aerosol separator further comprises:
a tubular body continuous with said aerosol outlet and said central chamber of said separator body.

41. An apparatus as recited in claim 35, wherein said aerosol separator further comprises:
means for reflecting acoustic energy from said supersonic jet within said central chamber of said separator body.

42. An apparatus as recited in claim 41, wherein said means for reflecting acoustic energy comprises angular walls, wherein larger aerosol particles can be divided into smaller aerosol particles.

43. An apparatus as recited in claim 35, further comprising:
means for storing produced aerosol.

44. An apparatus as recited in claim 43, wherein said means for storing produced aerosol comprises an enclosure.

45. An apparatus as recited in claim 44, said enclosure further comprising:
an ambient air intake port; and
a mouthpiece, wherein the aerosol contents of said enclosure can be inhaled by the user.

46. An apparatus as recited in claim 45, said intake port further comprising:
a directional valve, wherein the movement of the contents to and from said enclosure can be regulated.

47. An apparatus for producing aerosol, comprising:
a source of pressurized gas;
a supersonic shock nozzle;
a reservoir of liquid in fluid communication with said nozzle;
a metered valve configured to release said pressurized gas in bursts for delivery through said supersonic shock nozzle; and
an aerosol separator coupled to said shock nozzle, wherein large aerosol particles are separated from small aerosol particles;
wherein said supersonic shock nozzle comprises:
a jet orifice configured to receive compressed gas from said source of pressurized gas;
a lumen in fluid communication with said reservoir of liquid; and
a sonic shock chamber configured to receive entrained liquid mixed with a jet of compressed gas discharged from said jet orifice;
wherein said jet orifice is configured to produce a supersonic jet from said compressed gas;
wherein said shock chamber is configured to receive said supersonic jet and produce shock waves; and
wherein said supersonic jet is configured to establish a series of reflected compression and expansion shook waves in said shock chamber when said supersonic jet is over expanded or under expanded.

48. An apparatus as recited in claim 47, wherein said supersonic jet is configured to be approximately the diameter of the jet orifice and travel down the axis of the shock chamber.

49. An apparatus for producing aerosol, comprising:
a source of pressurized gas;
a supersonic shock nozzle;
a reservoir of liquid in fluid communication with said nozzle;
a metered valve configured to release said pressurized gas in bursts for delivery through said supersonic shock nozzle; and
an aerosol separator coupled to said shock nozzle, wherein large aerosol particles are separated from small aerosol particles;
wherein said supersonic shock nozzle comprises:
a jet orifice configured to receive compressed gas from said source of pressurized gas;
a lumen in fluid communication with said reservoir of liquid; and
a sonic shock chamber configured to receive entrained liquid mixed with a jet of compressed gas discharged from said jet orifice;
wherein said jet orifice is configured to produce a supersonic jet from said compressed gas;
wherein said shock chamber is configured to receive said supersonic jet and produce shock waves; and
wherein a cylindrical shock wave is generated in said shock chamber that envelopes the entire jet when said supersonic jet is perfectly expanded.

50. An apparatus for producing aerosol, comprising:
a source of pressurized gas;
a supersonic shock nozzle;
a reservoir of liquid in fluid communication with said nozzle;
a metered valve configured to release said pressurized gas in bursts for delivery through said supersonic shock nozzle; and
an aerosol separator coupled to said shock nozzle, wherein large aerosol particles are separated from small aerosol particles;
wherein said supersonic shock nozzle comprises:
a jet orifice configured to receive compressed gas from said source of pressurized gas;
a lumen in fluid communication with said reservoir of liquid; and
a sonic shock chamber configured to receive entrained liquid mixed with a jet of compressed gas discharged from said jet orifice;
wherein said jet orifice is configured to produce a supersonic jet from said compressed gas;
wherein said shock chamber is configured to receive said supersonic jet and produce shock waves; and
wherein upon formation of said supersonic jet and resulting shock waves in said shock chamber, liquid from said liquid reservoir is entrained through a liquid feed into said shock chamber.

51. An apparatus as recited in claim 50, wherein upon entrainment of liquid into the shock chamber, the initial liquid entrained comes in contact with shock waves, producing aerosol particles suitable for inhalation.

52. An apparatus for producing aerosol, comprising:
a source of pressurized gas;
a supersonic shock nozzle;
a reservoir of liquid in fluid communication with said nozzle;
a metered valve configured to release said pressurized gas in bursts for delivery through said supersonic shock nozzle;
an aerosol separator coupled to said shock nozzle, wherein large aerosol particles are separated from small aerosol particles;
an actuator handle, said actuator valve coupled to said handle; and
a trigger operably coupled to said actuator valve;
wherein said actuator handle is configured to receive a cartridge.

53. An apparatus as recited in claim 60, further comprising:
a cartridge containing said nozzle and a reservoir containing liquid for aerosolization dimensioned for insertion into said handle.

54. An apparatus as recited in claim 53, wherein said reservoir containing liquid comprises a blister pack.

55. An apparatus as recited in claim 54, wherein insertion of said cartridge into said actuator handle causes said blister pack to be punctured.

56. An apparatus as recited in claim 53, wherein said cartridge is disposable.

57. An apparatus as recited in claim 53, wherein insertion of said cartridge into said actuator handle causes said nozzle to be sealed with an outlet passage of said compressed gas source upon actuation of the actuator valve.

58. A method for producing an aerosol suspension comprising:
directing a flow of gas through a nozzle to form a supersonic jet of gas;
introducing material into the supersonic jet of gas to produce an aerosol suspension; and
reflecting acoustic energy through produced aerosol particles, wherein the size of said produced aerosol particles is reduced.

59. A method for producing an aerosol suspension as recited in claim 58, further comprising:
controlling said flow of gas through said nozzle.

60. A method for producing an aerosol suspension as recited in claim 59, wherein said controlling of said flow of gas comprises:
directing said flow of gas through said nozzle in bursts.

61. A method for producing an aerosol suspension as recited in claim 59, wherein said supersonic jet of gas is over expanded.

62. A method for producing an aerosol suspension as recited in claim 59, wherein said supersonic jet of gas is under expanded.

63. A method for producing an aerosol suspension as recited in claim 59, wherein said supersonic jet of gas is perfectly expanded.

64. A method for producing an aerosol suspension as recited in claim 58, further comprising:
directing said supersonic jet of gas through a sonic shock chamber.

65. A method for producing an aerosol suspension as recited in claim 64, further comprising:
establishing a series of reflected compression and expansion shock waves in said shock chamber when said supersonic jet of gas is directed through said sonic shock chamber.

66. A method for producing an aerosol suspension as recited in claim 58, further comprising:

regulating the volume of material introduced into said supersonic jet of gas.

67. A method for producing an aerosol suspension as recited in claim 58, further comprising:

regulating the rate of introduction of material that is introduced into said supersonic jet of gas.

68. A method for producing an aerosol suspension as recited in claim 58, further comprising:

separating small aerosol particles from large aerosol particles produced by said supersonic jet of gas.

69. A method for producing an aerosol suspension as recited in claim 68, further comprising:

storing separated small aerosol particles.

* * * * *